United States Patent [19]

Barton

[11] Patent Number: 5,157,032
[45] Date of Patent: * Oct. 20, 1992

[54] MIXED LIGAND COMPLEXES AND USES THEREOF AS BINDING AGENTS AND PROBES TO DNA

[75] Inventor: Jacqueline K. Barton, San Marino, Calif.

[73] Assignee: The Trustees of Columbia University In The City of New York, New York, N.Y.

[*] Notice: The portion of the term of this patent subsequent to May 12, 2009 has been disclaimed.

[21] Appl. No.: 539,930

[22] Filed: Jun. 18, 1990

Related U.S. Application Data

[63] Continuation-in-part of Ser. No. 268,247, Nov. 7, 1988, Pat. No. 5,112,974, which is a continuation-in-part of Ser. No. 905,295, Sep. 8, 1986, abandoned, which is a continuation-in-part of Ser. No. 693,023, Jan. 18, 1985, Pat. No. 4,721,669.

[51] Int. Cl.$^5$ .................. A61K 31/555; C07F 0/00
[52] U.S. Cl. .................... 514/185; 514/288; 514/885; 546/2; 546/10; 546/88; 536/27; 204/157.72; 424/9; 435/6
[58] Field of Search ............ 546/10, 2, 88; 514/185, 514/288, 885

[56] References Cited

U.S. PATENT DOCUMENTS 4,699,978. 10/1987 Barton .................... 536/27
4,721,669  1/1988 Barton .................... 435/6
4,980,473 12/1990 Barton .................... 546/10

OTHER PUBLICATIONS

Belser, et al., *Inorg. Chem.* vol. 20, pp. 3098-3103 (1981).
Barton, J. K., *J. Biomol. Struct. Dyn.* vol. 1, pp. 621-632 (1983).
Ackerman, M. N. and Interrante, L. V., *Inorg. Chem.* vol. 23, pp. 3904-3911 (1984).
Barton, J. K. and Raphael, A. L., *Proc. Natl. Acad. Sci. USA* vol. 82, pp. 6460-6464 (1985).
Barton, J. K. and Lolis, E., *J. Am. Chem. Soc.* vol. 107, pp. 708-709 (1985).
Barton, J. K., et al., *J. Am. Chem. Soc.* vol. 108, pp. 2081-2088 (1986).
Barton, J. K., *Science* vol. 233, pp. 727-734 (1986).
Goldstein, B. M. et al., *Inorg. Chem.* vol. 25, pp. 842-847 (1986).
Kumar, C. V. et al., *Inorg. Chem.* vol. 26, pp. 1455-1457 (1987).
Pyle, A. M. and Barton, J. K., *Inorg. Chem.* vol. 26, pp. 3820-3823 (1987).
Kirshenbaum, M. R. et al., *Nucleic Acids Research* vol. 16, 7943-7960 (1988).
Mei, H-Y and Barton, J. K., *Proc. Natl. Acad. Sci. USA* vol. 85, pp. 1339-1343 (1988).
Baum, R. M., *C& EN*, pp. 22-25, Jun. 12, 1989.
Friedman, A. E. et al., *J. Am. Chem. Soc.*, vol. 112, pp. 4960-4962 (1990).
Friedman, A. E. et al., *Nucleic Acids Res.*, vol. 19, pp. 2595-2601 (1991).

*Primary Examiner*—Cecilia Tsang
*Attorney, Agent, or Firm*—John P. White; Craig J. Arnold

[57] ABSTRACT

This invention concerns a coordination complex or salt thereof which is spectroscopically or photoactively determinable when bound to DNA having the formula

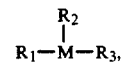

wherein M is a suitable transition metal and each of $R_1$, $R_2$ and $R_3$ is ethylenediamine, bipyridine, phenanthroline, diazafluorene-9-one or a substituted derivative thereof, or phenanthrenequinonediimine or a substituted derivative thereof, dypyridophenazine or a substituted derivative thereof; wherein $R_1$, $R_2$ and $R_3$ are bound to M by coordination bonds; provided that at least one of R1, R2 or R3 is dypyridophenazine or a substituted derivative thereof. The invention also concerns a labeled DNA probe which comprises the complex covalently bound to the DNA probe. Further the invention concerns a method of detecting the presence in a sample a target DNA of interest which comprises contacting the sample containing the target DNA with a complementary labeled DNA probe under hybridizing conditions and measuring the resulting luminescense emitted from the labeled DNA probe, a change in the luminescense as compared with the luminescense in the absence of the sample indicating the presence of the target DNA.

18 Claims, 59 Drawing Sheets

Ru(phi)$_3^{2+}$

Δ Ru(DIP)$_2$(phen)$^{2+}$

Δ Ru (phen)$_3^{2+}$

Figure 6C
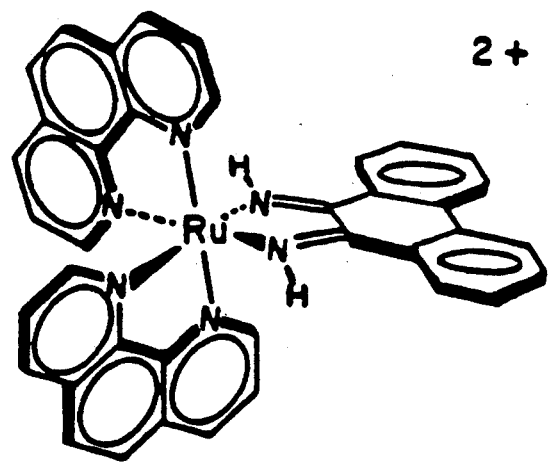

Δ Ru(bpy)$_2$(phen)$^{2+}$ 1,10-phenanthroline
(phen)

2,2'-bipyridyl
(bpy)

9,10-phenanthrene-
quinonediimine
(phi)

4,7-diphenylphenanthroline
(DIP)

5-nitrophenanthroline
(5-NO$_2$-phen)

4,5-diazafluorene-9-one
(flone)

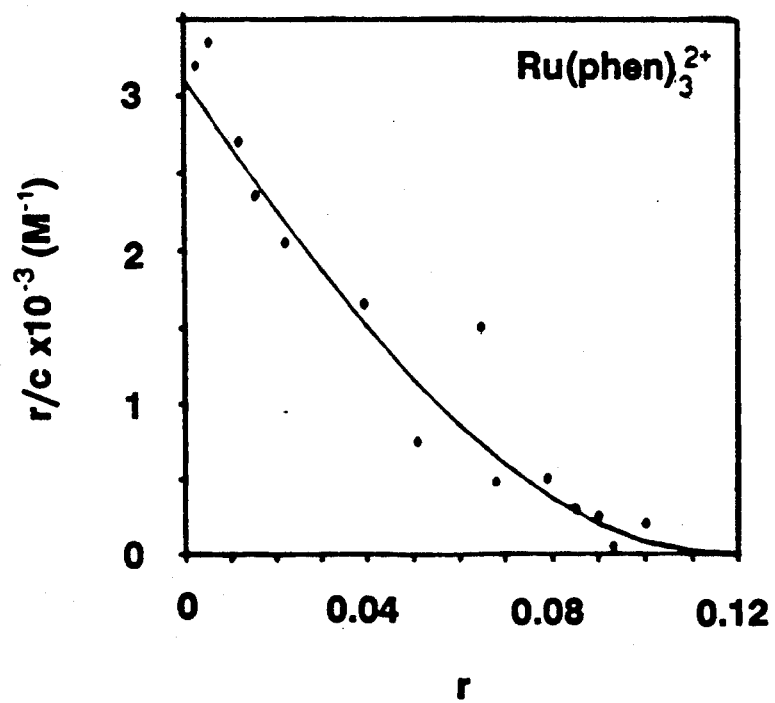
Figure 8A₁

Figure 8A$_2$
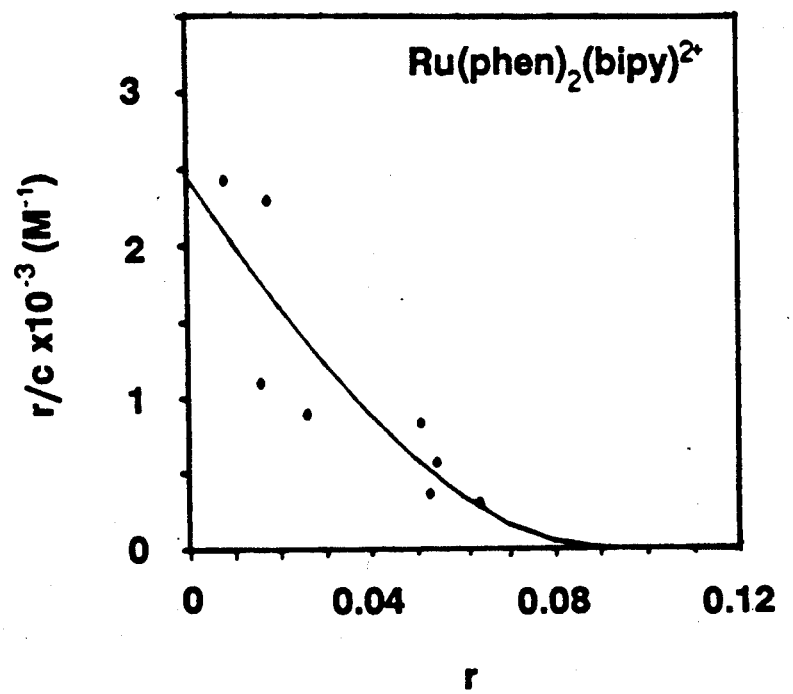

Figure 8A₃
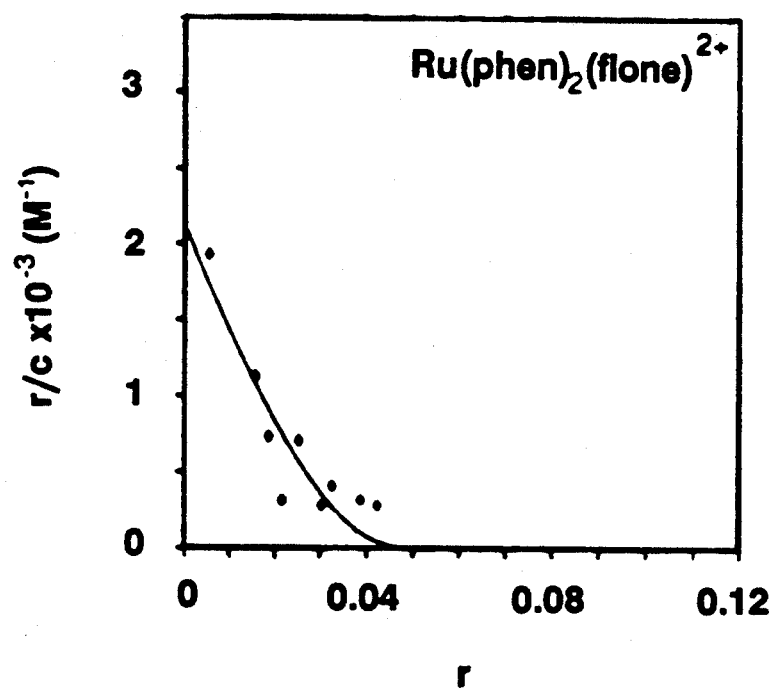

Figure 8A$_4$
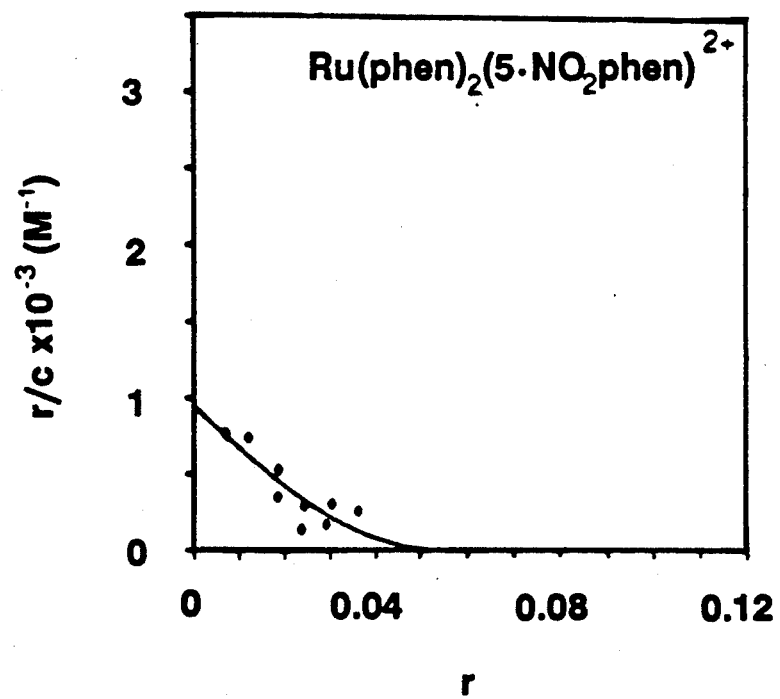

Figure 8A$_5$
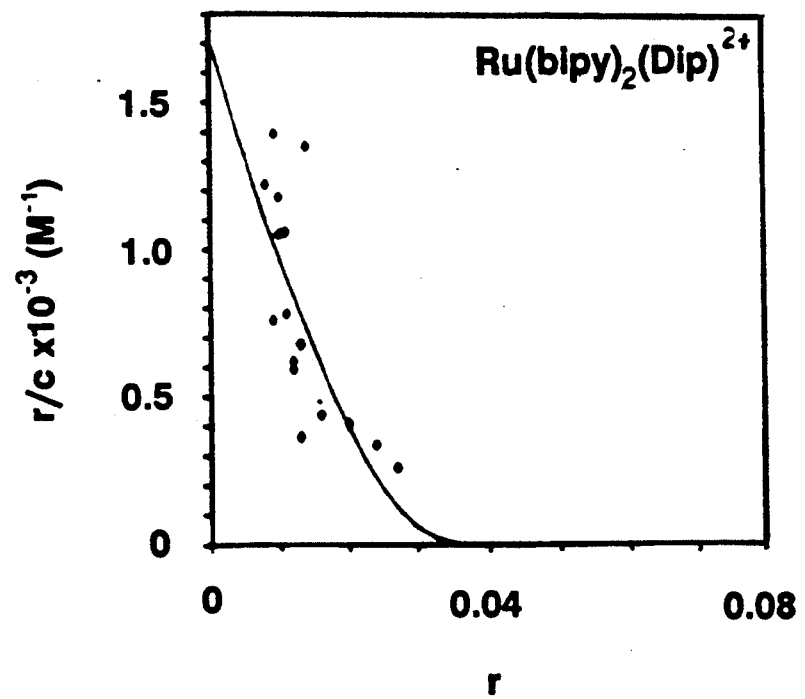

Figure 8A$_6$
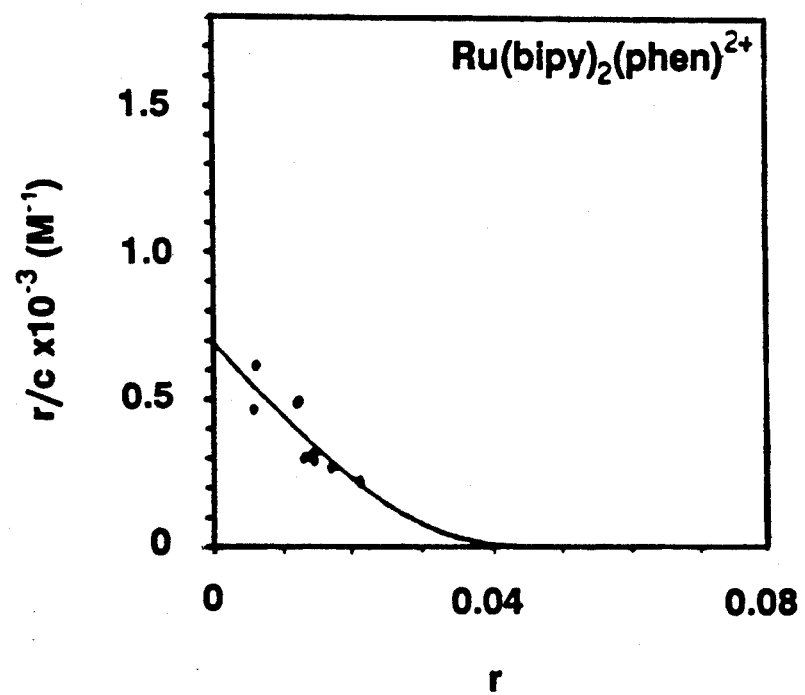

Figure 8A$_7$
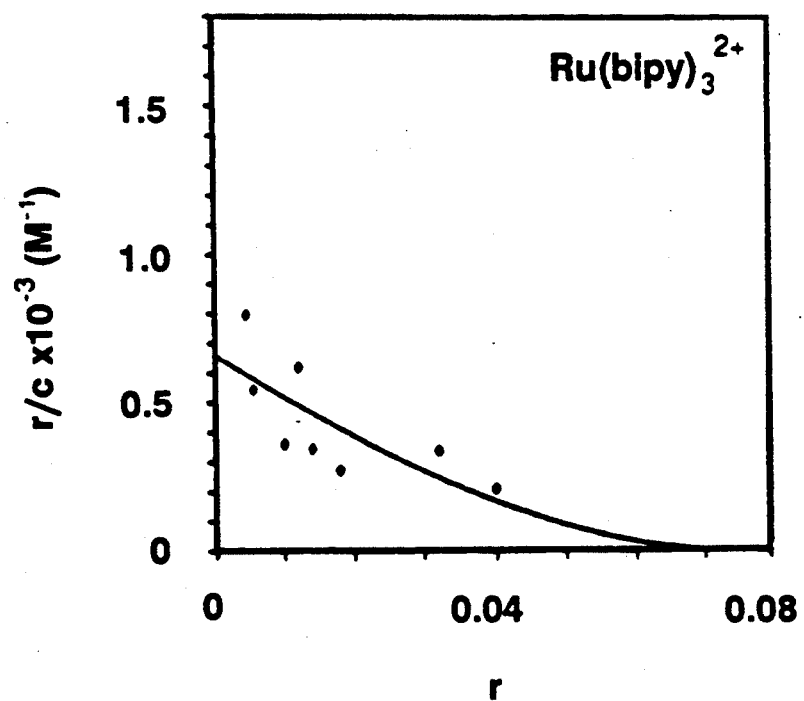

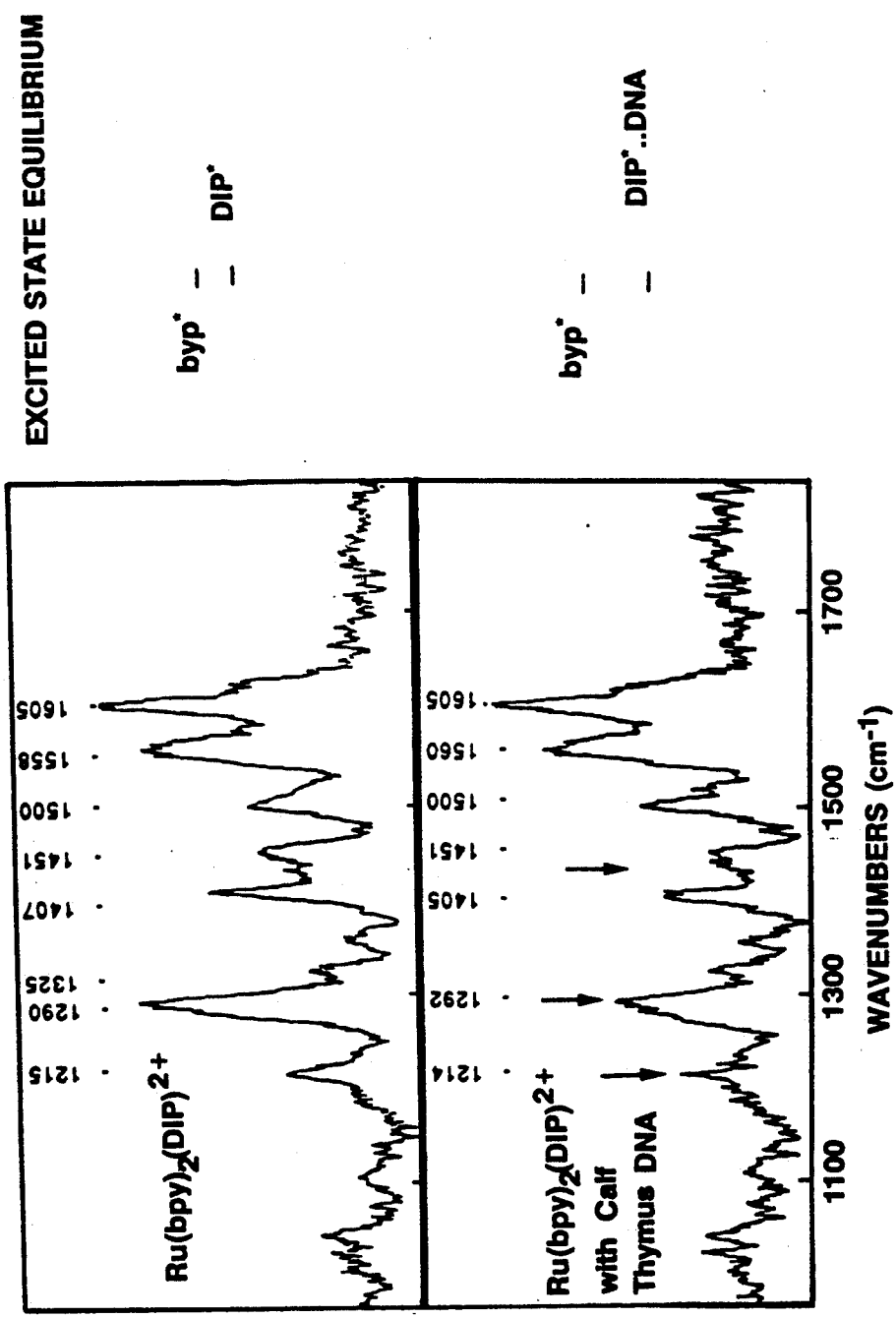

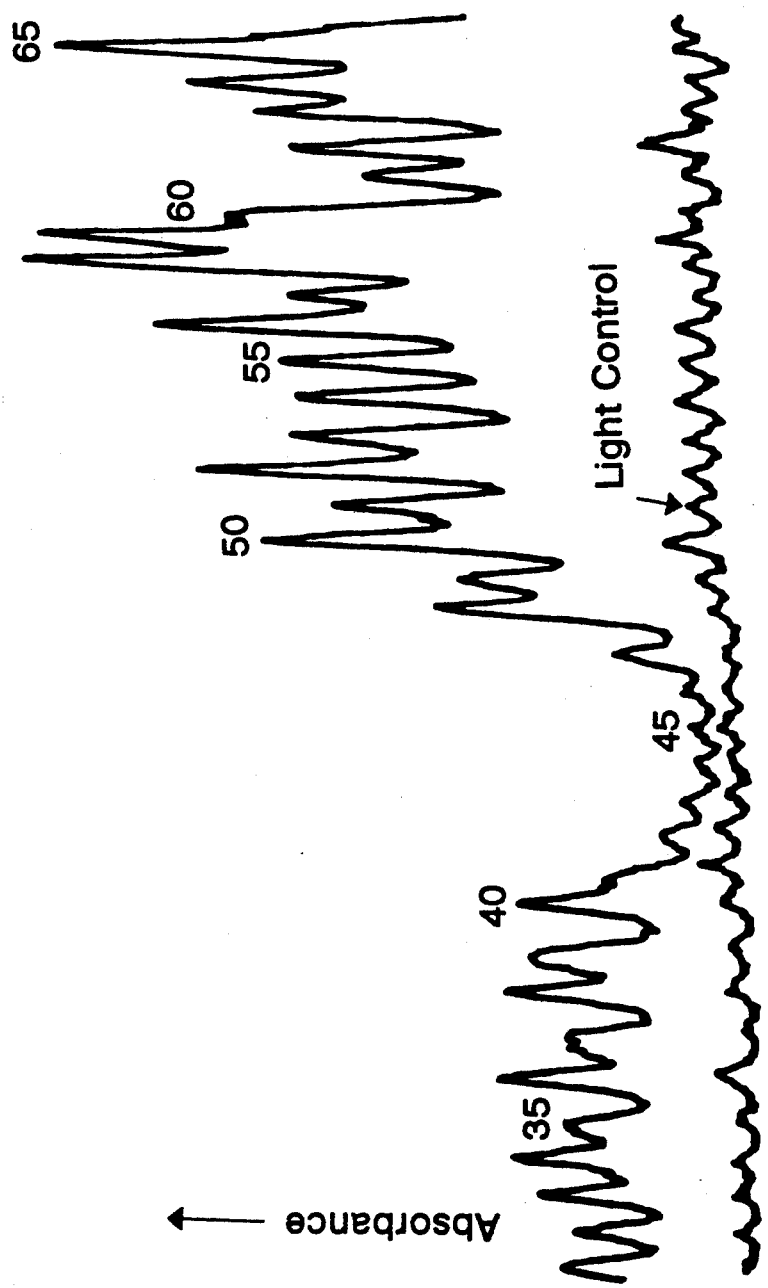
Figure 13B₁

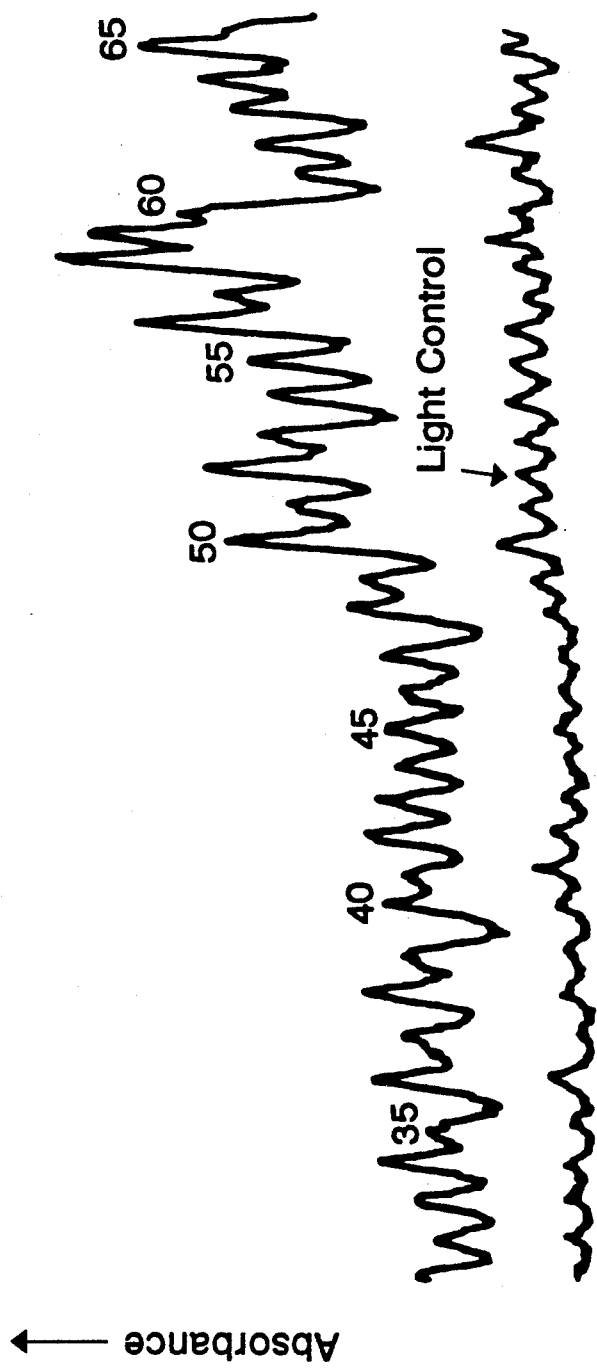
Figure 13B₂

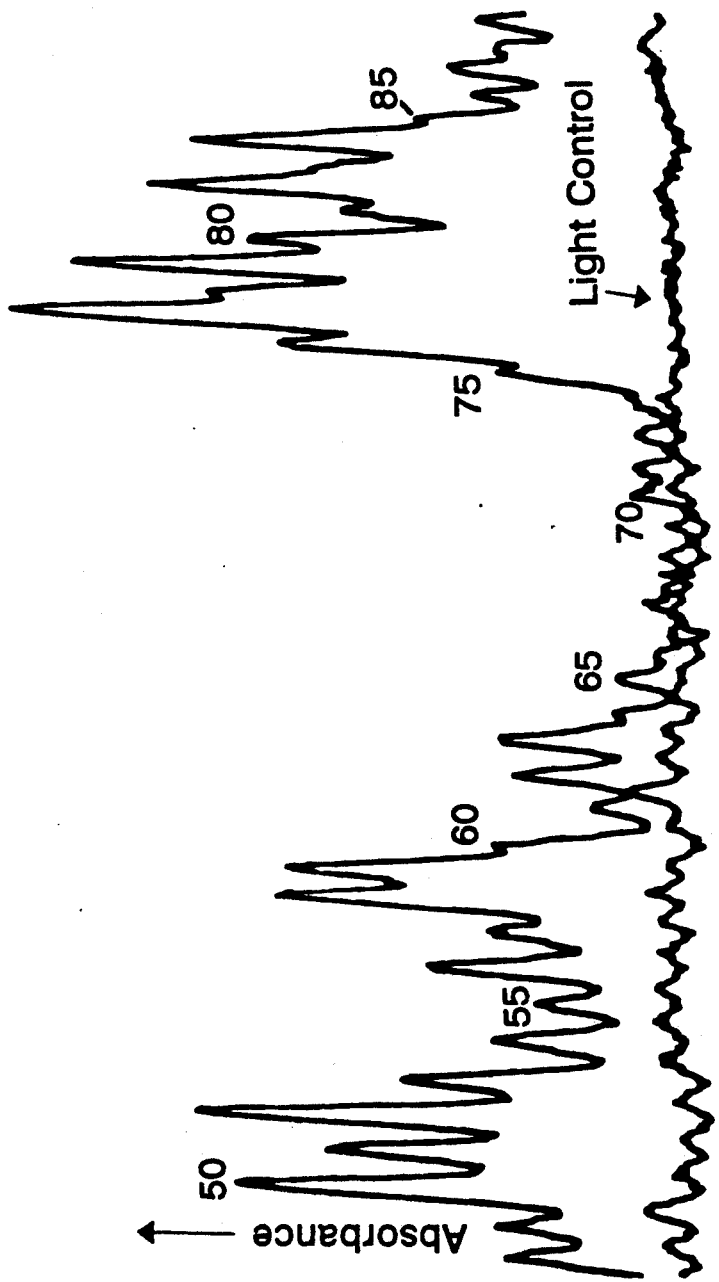
Figure 14B₁

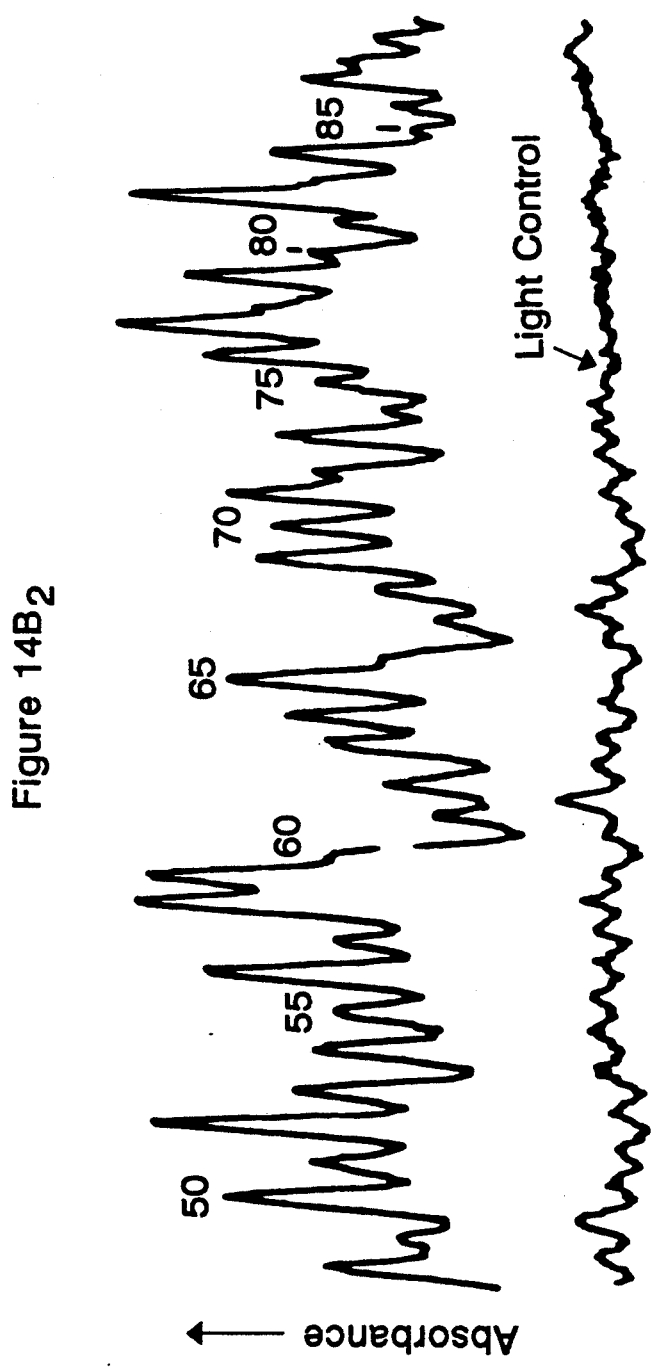
Figure 14B₂

Figure 18A

```
        35        40        45        50        55
         |         |         |         |         |
5'  CCCCATATGCAAAAAAGCATATGGG
3'  GGGGTATACGTTTTTTCGTATACCC
```

Figure 18B

```
        50        55        60        65        70        75        80
         |         |         |         |         |         |         |
5'  ATATGGGTACCGAGCTCGAATTCGTAATCATG
3'  TATACCCATGGCTCGAGCTTAAGCATTAGTAC
```

Rh(phi)2(bpy)3+

MPE-Fe(II)

DNase I

Cu(phen)$_2^+$

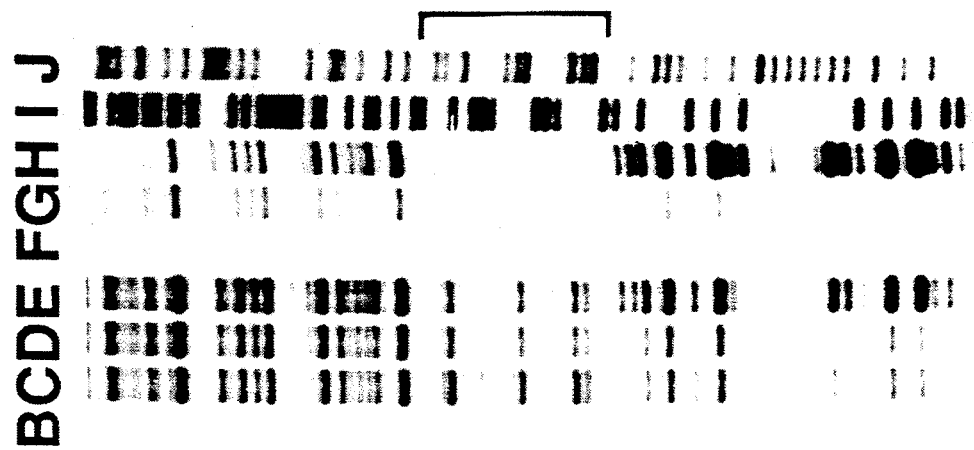
Figure 20C DNase I
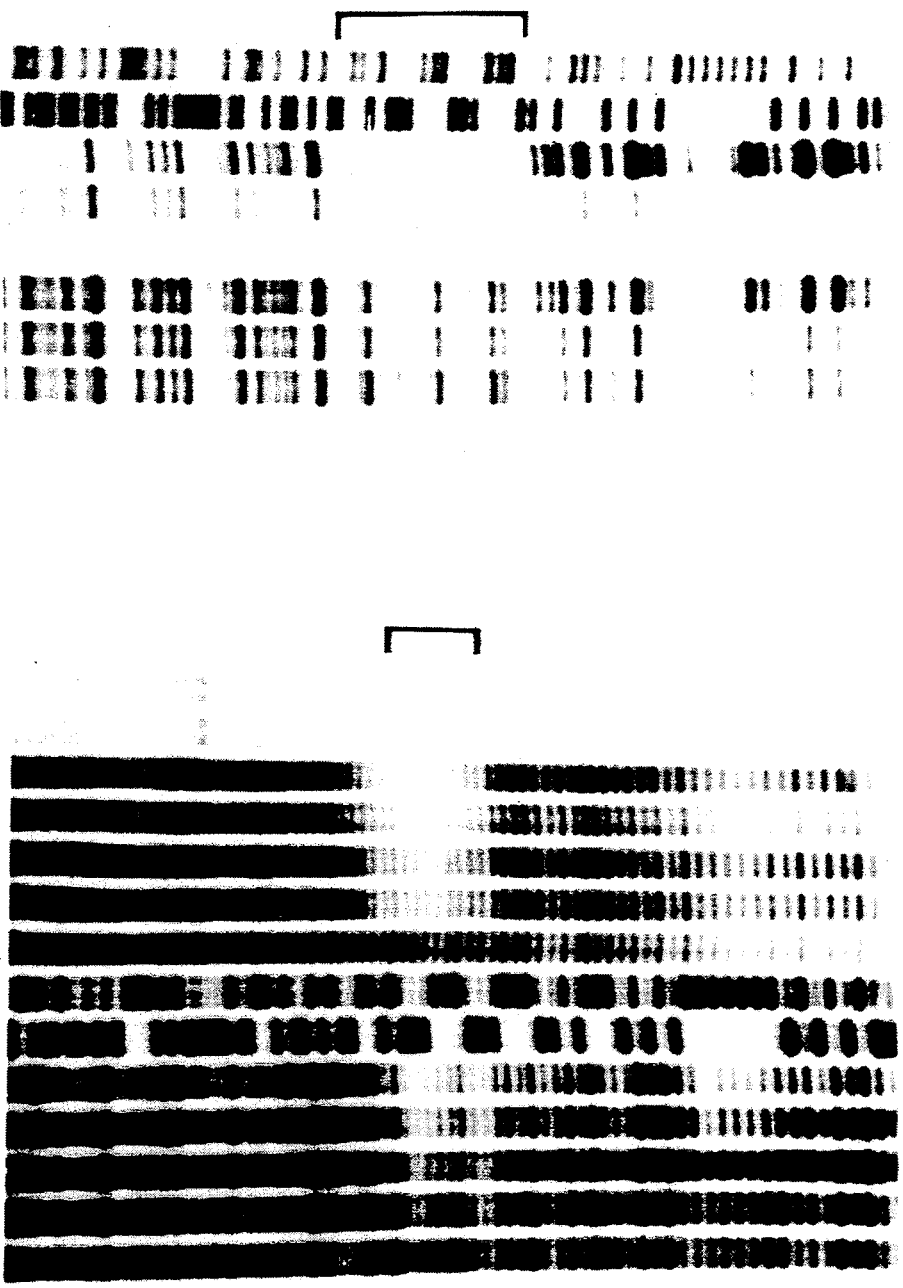
Figure 20B MPE-Fe(II)
Figure 20A Rh(phi)$_2$(bpy)$^{3+}$

IN VITRO ANTI-HIV DRUG SCREENING RESULTS

Log of Sample Concentration (µg/mL)

MIXED LIGAND COMPLEXES AND USES THEREOF AS BINDING AGENTS AND PROBES TO DNA

The invention was made with government support under grant number CG 33309 from the National Institutes of General Medical Science, the U.S. Department of Health and Human Services and with the support from the National Science Foundation.

This application is a continuation-in-part of Ser. No. 268,247, filed Nov. 7, 1988, now U.S. Pat. No. 5,112,974 which is a continuation in part of U.S. Ser. No. 905,295 now abandoned filed Sept. 8, 1986, which in turn is a continuation-in-part of U.S. Ser. No. 693,023, filed Jan. 18, 1985, now U.S. Pat. No. 4,721,669, issued Jan. 26, 1988, the contents of which are hereby incorporated by reference into the present application.

BACKGROUND OF THE INVENTION

Some of the information set forth herein has been published. See Pyle, A. M. and Barton, J. K., Mixed Ligand Complexes and Uses Thereof as Binding Agents to DNA, Inorganic Chemistry, 1987, 26:3820-3823, which was distributed by the published on Nov. 6, 1987.

Throughout this application various publications are referenced by arabic numerals within parentheses. Full citations for these publications may be found at the end of the specification immediately preceding the claims. The disclosures of these publications in their entireties are hereby incorporated by reference into this application in order to more fully describe the state of the art to which this invention pertains.

There has been considerable interest in elucidating those factors which determine affinity and selectivity in binding of small molecules to DNA. (66-72) A quantitative understanding of such factors which determine recognition of DNA sites would be valuable in the rational design of sequence-specific DNA binding molecules for application in chemotherapy and in the development of tools for biotechnology. Much work has focused on the elucidation of non-covalent interactions with DNA by small natural products and their synthetic derivatives. (67-72) These small molecules are stabilized in binding to DNA through a series of weak interactions, such as the $\pi$-stacking interactions associated with intercalation of aromatic heterocyclic groups between the base pairs, and hydrogen bonding and Van der Waals interactions of functionalities bound along the groove of the DNA helix. It would be valuable to understand quantitively the contributions from these different modes to stabilization of the bound complex at a DNA site.

Previous work has focused on the examination of non-covalent interactions with DNA of transition metal complexes of phenanthroline. (66, 73-77) The cationic complexes has been found both to intercalate into DNA and to bind non-covalently in a surface-bound or gove-bound fashion. These interactions with DNA have been characterized largely through spectroscopic and photophysical studies, and determinations of enantiomeric selectivities associated with binding by the metal complexes have been helpful also in establishing models. (73, 74) On the basis of these investigations, intercalation likely occurs preferentially from the major groove of the DNA helix and is favored for the $\Delta$ isomer into a right-handed helix. In the case of the surface-bound interaction, it likely occurs along the minor groove of the helix and it is the $\Lambda$ isomer which is favored in surface-binding to right-handed DNA helices. FIG. 5 illustrates models for these binding interactions.

Based upon these binding interactions, derivatives of tris (phenanthroline) complexes have been developed which recognize selectively different conformations of DNA. By matching shapes and symmetries of the metal complexes to those of DNA conformations, probes for A-and Z-DNA have been designed. (75) Most recently, a diphenylphenanthroline complex of rhodium (III) has been found to induce double-stranded cleavage at cruciform sites upon photoactivation. (76). Although these complexes lack hydrogen bonding donors and acceptors and therefore must be associating with DNA only through a mixture of Van der Waals and intercalctive interactions, a high level of specificity is associated with the recognition of different DNA sites by these complexes.

The present invention involves mixed ligand complexes and complexes having three phenanthrenequinone diiamine ligands. The mixed ligand complexes of ruthenium (II) were explored for their interactions with B-DNA using a variety of biophysical and spectroscopic methods. Mixed ligand complexes of phenanthroline, phenanthrenequinonediimine, and derivatives thereof have been found to be useful for the construction and characterization of DNA-binding molecules. The ruthenium (II) complexes are particularly useful owing to their intense optical absorption and emission, their relative ease of preparation, and their inertness to substitution and racemization. (77-79).

The technique of DNA footprinting has been used extensively to observe the site-specific binding of proteins, peptides, and drugs to DNA (1-4). Using a variety of chemical and enzymatic footprinting agents, it has been possible to determine the relative binding site sizes and locations for hundreds of DNA-binding proteins. Subtle molecular interactions between DNA and transcription factor, repressor, and other constituents of the transcriptional apparatus are being actively explored using DNA footprinting (5).

Given the power of this methodology, extensive efforts to find new, high resolution footprinting reagents are underway. The most popular and the original footprinting reagent is DNase I, a large nuclease which cleaves with some preference for sequences of intermediate groove widths (6). This level of sequence-neutrality is sufficient for determining the binding sites of large DNA binding proteins. However, small peptides or proteins which bind to sequences insensitive to attack by DNase I can be difficult to visualize. Many chemical footprinting reagents such as $Cu(phen)_2^+$ and metalloporphyrins share this inherent problem (7,8). In order to examine DNA binding interactions at higher resolution, many workers have turned to MPE-Fe(II), the first synthetic footprinting reagent and a remarkable tool with respect to its sequence neutrality. An intercalating dye tethered to an $Fe(EDTA)^{2-}$ moiety, MPE-Fe(II) has been useful in elucidating the binding sites and sizes of small natural products as well as proteins (9-12). More recently, the clever application to footprinting of $Fe(EDTA)^{2-}$ itself, without a tethered DNA-binding moiety, has been made (3,13). Both for $Fe(EDTA)^{2-}$ and ME-Fe(II), cleavage results from the diffusion to the DNA helix of hydroxyl radicals, generated in the presence of peroxide and a reducing agent (3,9,13). $FE(EDTA)^{2-}$, which as an anionic species generates the radicals far from the DNA surface, also shows a high level of sequence neutrality, but since the radical generator does not bind to the DNA, high concentrations of reagents are required. Additionally a drawback with respect to both complexes has been their sensitivity to the presence of various common additives, such as glycerol or Mg$^{2+}$, and their requirements for high concentrations of chemical activators.

Some techniques of photofootprinting have also been developed. An advantage of this method is that the activation of the DNA cleavage reaction is controlled by light, eliminating the need for adding other chemicals to the protein solution. These techniques include ultraviolet footprinting (14), photofootprinting in the presence of uranyl salts (15), and that in the presence of psoralen or its analogs (16). Ultraviolet light photofootprinting has been applied in vivo as well as in vitro. This technique requires chemical treatment after the photocleavage reaction, however, and the obtained results are sometimes complicated because of differential enhancements due to DNA-protein crosslinking. The second technique, using uranyl salts, shows excellent sequence neutrality but high concentrations of the uranyl salts are required, which may perturb the protein interactions with the DNA or the DNA structure itself. Psoralen footprinting lacks in sequence-neutrality. Owing to these difficulties, despite the inherent advantages of light activation, these photofootprinting reagents have not been widely applied.

Recently, coordinatively saturated phenanthrenequinone diimine complexes of rhodium (III) have been reported to cleave DNA efficiently upon irradiation with long-wavelength ultraviolet light (17). Photocleavage with Rh(phi)$_2$(bpy)$^{3+}$ yields sharp, sequence-neutral cleavage of linear DNA fragments. The addition of free metal ions, chelators, or oxidizing agents is not necessary in this system because the Rh(phi)$_2$(bpy)$^{3+}$ complex is fully assembled and requires activation only by light. The structure of Rh(phi)$_2$(bpy)$^{3+}$ is schematically illustrated below.

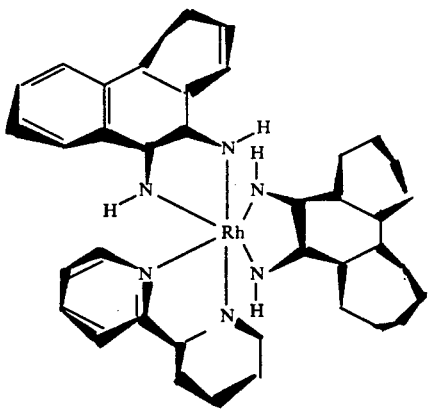

Rh(phi)$_2$(bpy)$^{3+}$ is a high-resolution photofootprinting reagent which successfully maps the precise binding locations and site sizes of distamycin-A and the restriction endonuclease EcoRI. This is the first report of a chemical footprint for EcoRI and the first example of a footprint which reflects the proper site size (18).

Rh(phi)$_2$(bpy)$^{3+}$ is able to detect both EcoRI bound in the major groove of DNA and the small peptide distamycin, bound in the minor groove. Footprinting with Rh(phi)$_2$(bpy)$^{3+}$ is not inhibited by moderate concentrations of salts, EDTA, glycerol, or reducing agents, many of which are sometimes necessary to obtain a native interaction of DNA with protein. The complex is ease to handle, being very stable under ordinary conditions and requiring no complicated reaction conditions. Activation with low energy light from a lamp or transilluminator permits excellent experimental control over Rh(phi)$_2$(bpy)$^{3+}$ footprinting, an absolute requirement for application in vivo.

Extensive data has been accumulated on the luminescence properties of ruthenium (II) polypyridyls, the results of which in sum, suggest that the complexes are extremely useful luminescent labels for DNA. Recently, there has been concern with the use of these complexes as probes for specific sites of binding on the DNA helix. Among the reasons for their use in this work is that each complex can be resolved into stable isomers[34] and that their metal-to-ligand-charge-transfer (MLCT) excited states are easily accessible[35]. It has previously been found that B-form DNA selectively bound the Δ-enantiomers of Ru(phen)$_3^{2+}$ and Ru(dip)$_3^{2+}$ over the Ω-forms[36]. More recently it was demonstrated that Z-form DNA selectively binds the Ω-enantiomers of Ru(phen)$_3^{2+}$ and Ru(dip)$_3^{2+}$[81]. With this in mind, there is considerable interest in the development of new transition metal probes which would be more general in its binding and provide more information about its local DNA environment. Specifically, a complex whose luminescence properties would respond to subtle changes in environment upon binding.

The present invention involves, one such candidate, because of high binding ability to DNA is Ru(bpy)2(dppz)$^{2+}$ (bpy=2,2'-bipyridine, dppz=dipyrido[3,2: a-2',3'-cphenazine)[38] which does not luminesce in aqueous solution. Ru(bpy)$_2$(dppz)$^{2+}$ was found to have appreciable luminescence in ethanol ( $\lambda_{irr}$=482 nm, $\lambda_{max}$=610 nm) and in acetonitrile ( $\lambda_{irr}$=482 nm, $\lambda_{max}$=615 nm) The ancillary bpy ligands assures that intercalation only occurs via the dppz ligand. Furthermore, the two bpy ligands are not expected to provide enantiomeric selectivity for this complex[36]. In addition the LUMO of this complex is described as having a very large electron density on the phenazine nitrogens[39], because this ligand is believed to extensively intercalate this provides an excellent probe of the helix environment. The major nonradiative deactivation pathway probably involves the protonation of the phenazine nitrogens in the excited state, which potentially provides an excellent probe of the interior of the DNA helix upon intercalation.

SUMMARY OF THE INVENTION

This invention concerns a coordination complex or salt thereof which is spectroscopically or photoactively determinable when bound to DNA having the formula

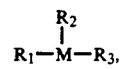

wherein M is a suitable transition metal and each of R$_1$, R$_2$ and R$_3$ is ethylenediamine, bipyridine, phenalnthroline, diazafluorene-9-one, phenanthrenequinonediimine or dipyridophenazine. In the complex, R$_1$, R$_2$ and R$_3$ are bound to M by coordination bonds and R$_1$ and R$_2$ may be the same or different, but if the same are different from R$_3$. In the preferred embodiments, the invention concerns complexes of ruthenium(Ru) or rhodium(Rh) wherein $R_1$ and $R_2$ are the same.

Also, the invention concerns a coordination complex or salt thereof which is spectroscopically or photoactively determinable when bound to DNA having the formula

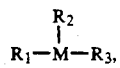

wherein M is a suitable transition metal and each of $R_1$, $R_2$ and $R_3$ is ethylenediamine or a substituted derivative thereof, bipyridine or a substituted derivative thereof, phenanthroline or a substituted derivative thereof, diazafluorene-9-one or a substituted derivative thereof, or phenanthrenequinonediimine or a substituted derivative thereof, dipyridophenazine or a substituted derivative thereof; wherein $R_1$, $R_2$ and $R_3$ are bound to M by coordination bonds; provided that at least one of $R_1$, $R_2$ or $R_3$ is dipyridophenazine or a substituted derivative thereof.

The invention also concerns the complex

wherein M is Ru or Rh and R is 9-10-phenanthrenequinonediimine, 5-nitro-phenanthroline or 3,2-dipyridophenazine or a substituted derivative thereof.

The invention also concerns a method for labeling double stranded DNA with the complex which comprises contacting the DNA with a complex so that it binds to and labels the DNA. In a particular embodiment the complex is used to selectively label a conformation present in the double stranded DNA which comprises contacting the DNA with the complex or an isomer of the complex so that the complex or the isomer binds to the conformation. The invention also also concerns a labeled DNA probe which comprises the complex covalently bound to the DNA probe. The invention further concerns a method of detecting the presence in a sample of a target DNA of interest which comprises contacting the sample containing the target DNA with a complemetrary labeled DNA probe under hybridizing conditions and measuring the resulting luminescence emitted from the labeled DNA probe a change in the luminescence indicating the presence of the target DNA. The invention also concerns a method for detecting the presence of the conformation present in double stranded DNA which comprises selectively labeling the conformation and then detecting the presence of the complex of the isomer of the complex bound to the conformation. The invention also concerns a method for nicking double stranded DNA by effecting breakage of at least one phosphodiester bond along the DNA which comprises contacting the DNA with the coordination complex under conditions such that the complex binds to the DNA to form an adduct and irradiating the adduct so formed with visible light or ultraviolet radiation of an appropriate wavelength which is absorbed by the complex so as to nick the DNA at the site of binding. Also provided is a method for cleaving double stranded DNA which comprises nicking the DNA according to the present invention and treating the nick DNA with an enzyme which is not deactivated in the presence of the complex used for nicking DNA and is capable of cleaving single stranded DNA so as to cleave the DNA at the site of the nick. The invention further concerns a method for photocleaving DNA to produce a footprint of DNA binding sites.

The invention also provides a method for killing a portion of a population of appropriate tumor cells which comprises contacting the tumor cells under suitable conditions with an effective amount of the coordination complex so as to kill the tumor cells. Lastly, the invention concerns a method for treating a subject afflicted with a human immunodeficiency virus which comprises administering to the subject an effective amount inhibit the activity of the virus.

BRIEF DESCRIPTION OF FIGURES

FIG. 6A to 6D: Illustration of several mixed ligand complexes: Ω-Ru(DIP)$_2$phen$^{2+}$ (top left); Δ-Ru(phen)$_3^{2+}$ (top right); Δ-Ru(phen)$_2$phi$^{2+}$ (bottom left); Δ-Ru(bpy)$_2$phen$^{2+}$ (bottom right).

FIG. 12: Excited state resonace Raman spectrum of $Ru(bpy)_2DIP^{2+}$ in the absence (top) and presence (bottom) of calf thymus DNA. The arrows indicated those transitions determined earlier[30] to reflect excited state charge transfer which is localized onto the bypy ligand. These spectral indicate that the presence of DNA the intensity of transitions dominated by charge localization onto bpy is reduced relative to those dominated by charge transfer to the DIP ligand.

(c). Values of (Ic-Ie)/Ic are plotted against base pair number for 5'-and 3-end labeled strands.

Figure 15:
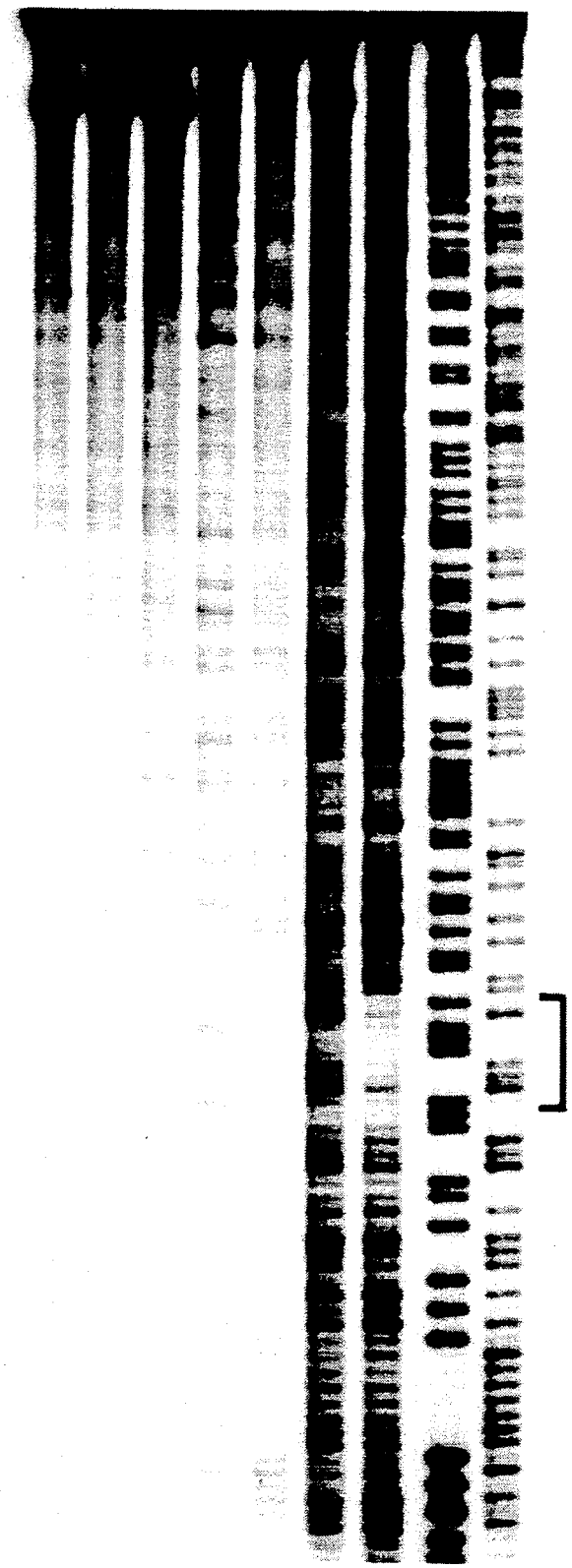

FIG. 15 $Rh(phi)_2(bpy)^{3+}$ footprinting of EcoRI using a transilluminator as light source. Lanes F and G: cleavage by $Rh(phi)_2(bpy)$; in the absence and presence of EcoRI (296 units), respectively, using 20-min irradiation with the box. Lane A: Intact 245 pb DNA fragment, 3'-end-labeled. Lanes B and C: dark controls in the absence and presence of EcoRI, respectively. Lanes D and E: light controls in the absence and presence of EcoRI, respectively. Lanes H and I: Maxam-Gilbert A+G and C+T reactions, respectively. Footprinted region is indicated by a bracket.

Figure 16:
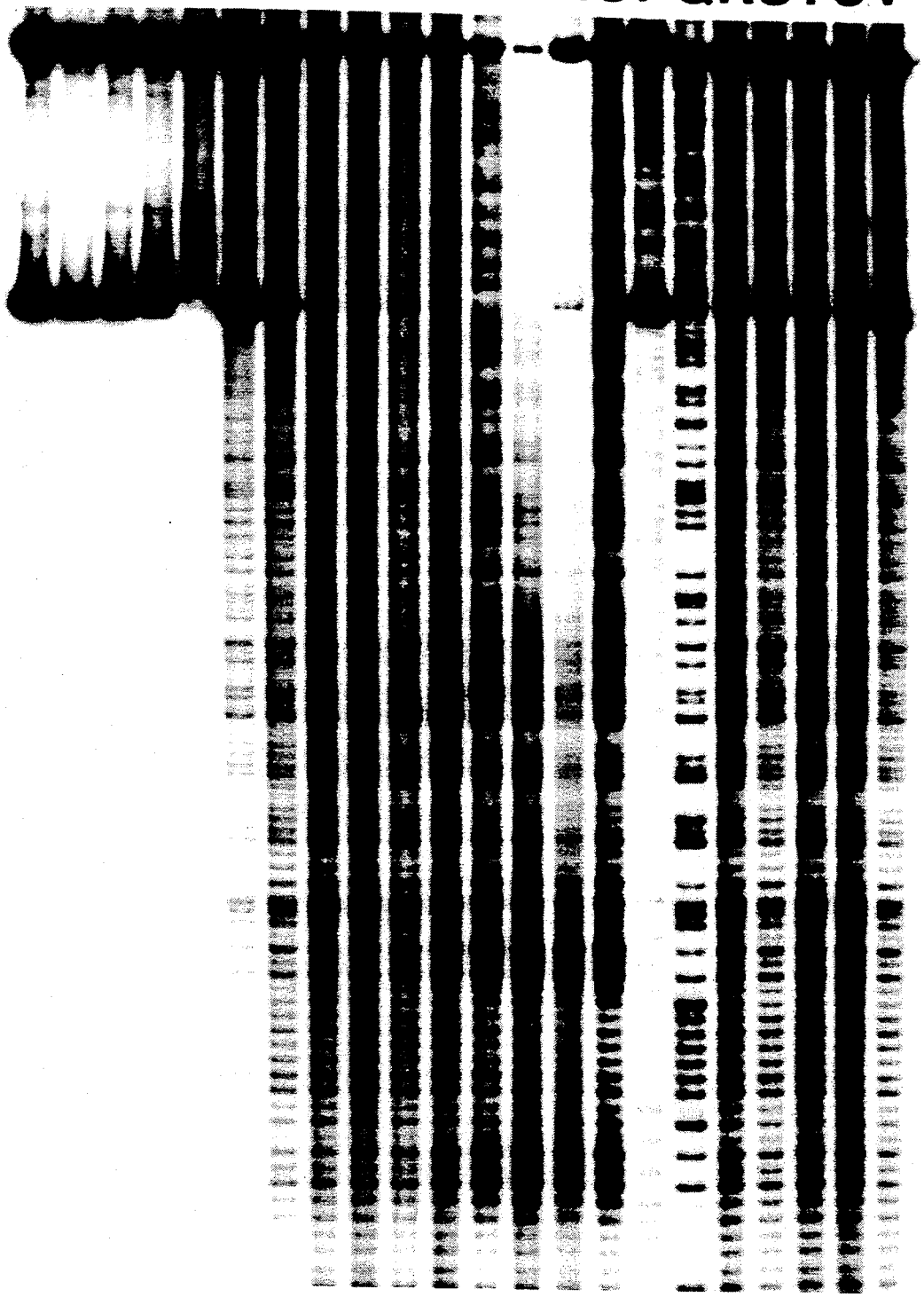

FIG. 16 Autoradiogram of 3'-end-labeled DNA fragment photocleaved in the presence of $Rh(phi)_2(bpy)^{3+}$ under various conditions. Lanes A-E are controls: A: Intact DNA fragment (no irradiation and no metal complex). B and C: dark controls (room temperature for 10 and 50 min, respectively, in the dark) in the presence of 5 and 15 μM Rh-complex, respectively. D and E: light controls (no Rh-complex) with 10- and 50-min irradiation, respectively, with focused maximum intensity ($I_{max}$) of Hg/Xe lamp. Lanes F, G, and H: 15 μM Rh-complex and 1 min, 3 min 20 sec, and 10 min irradiation ($I_{max}$), respectively. Lanes I, J, and K: 10, 5, and 2.5 μM, rhodium complex, respectively, and 10 min irradiation ($I_{max}$). Lanes L, M, and N: 1 μM Rh-complex and 10,25, and 50 min irradiation ($I_{max}$), respectively. Lane 0:0.5 μM and 10 min irradiation ($I_{max}$) Lane R: 5 μM rhodium complex and 10,25, and 50 min irradiation with $I_{max}/5$, respectively, Lane V: 5 μM Rh-complex and 10 min irradiation with $I_{max}/10$. Total DNA concentration was 5 μM base pairs. Lanes P and Q were Maxam-Gilbert A+G and T+C reactions respectively.

Figure 17:

FIG. 17. Effect of metal ions, EDTA, and glycerol on DNA photocleavage by $Rh(phi)_2(bpy)$ Lanes A, B, and C: Intact DNA, dark control, and light control, respectively. Lanes D and E: Maxam-Gilbert A+G and T+C reactions, respectively. Lane F: cleavage by $Rh(phi)_2(bpy)^{3+}$ in the absence of additives. Lanes G, H, and I: in the presence of additional 0.1, 0.5, and 2.5 M NaCl, respectively. J, K, and L: in the presence of 1, 10, and 100 mM MgCl$_2$. M, N, and 0: in the presence of 1, 10, and 100 mM CaCl$_2$,. P, Q, and R: in the presence of 1, 10, and 50 mM EDTA. S, T, and U: in the presence of 0.1, 1, and 10% of glycerol. Fragment was 3'-end-labeled and irradiation time was 5 min with a Hg/Xe lamp under the standard conditions described for $Rh(phi)_2(bpy)^{3+}$ photocleavage.

FIG. 18A and 18B: Sequence of the 245 base pair restriction fragment used in these experiments showing in histogram form the footprinted sites both for distamycin (above) and EcoRI (below) using $Rh(phi)_2(bpy)^{3+}$ The 5'-end-labeled fragment is labeled with $^{32}P$ at the 3'end of the lower strand.

Figure 19A:
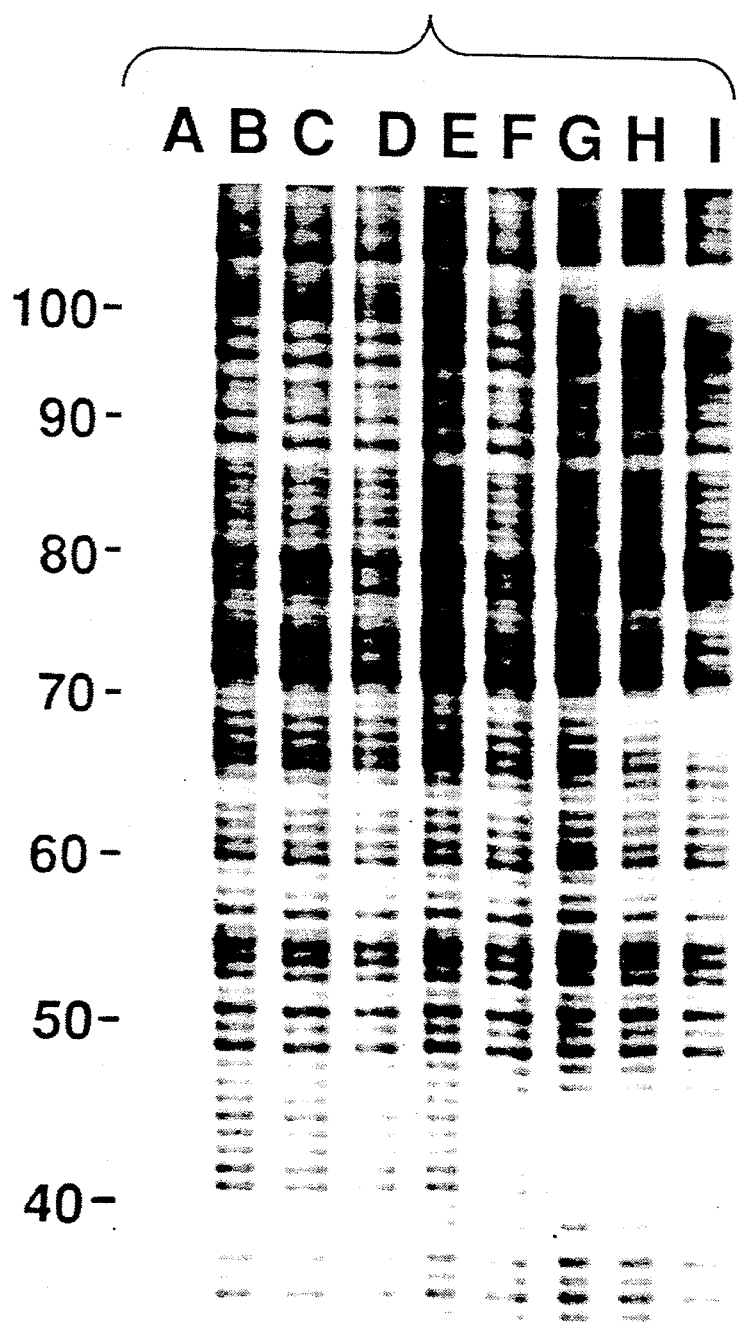
Figure 19B:
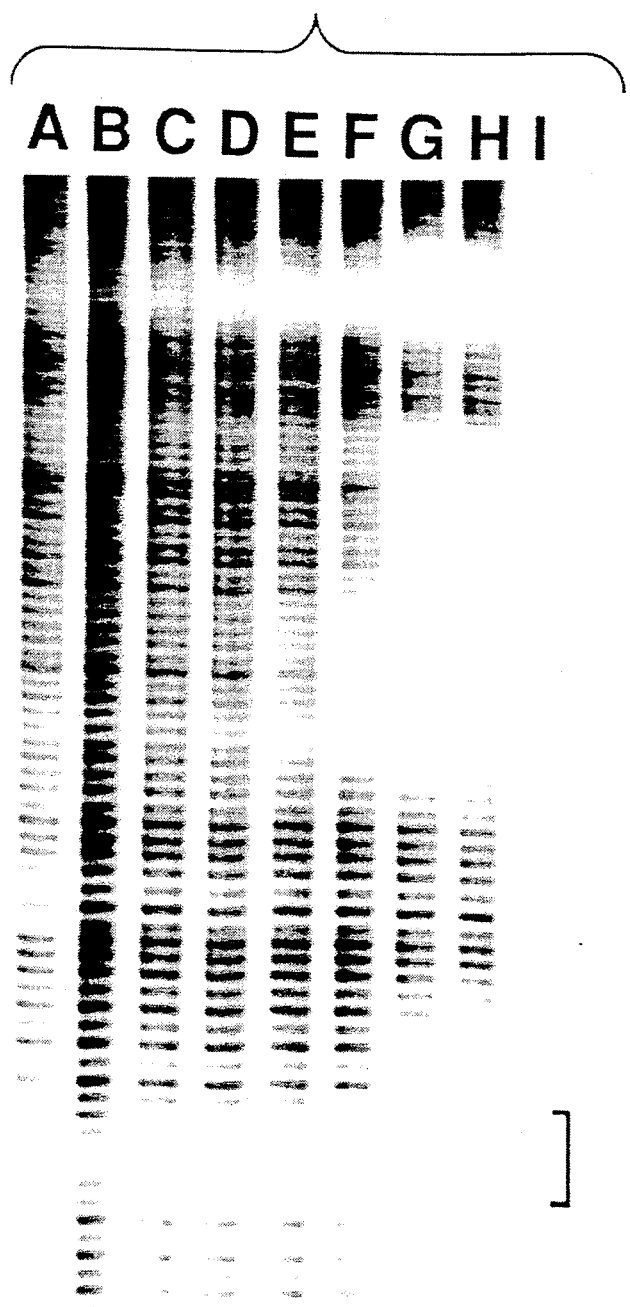
Figure 19C:
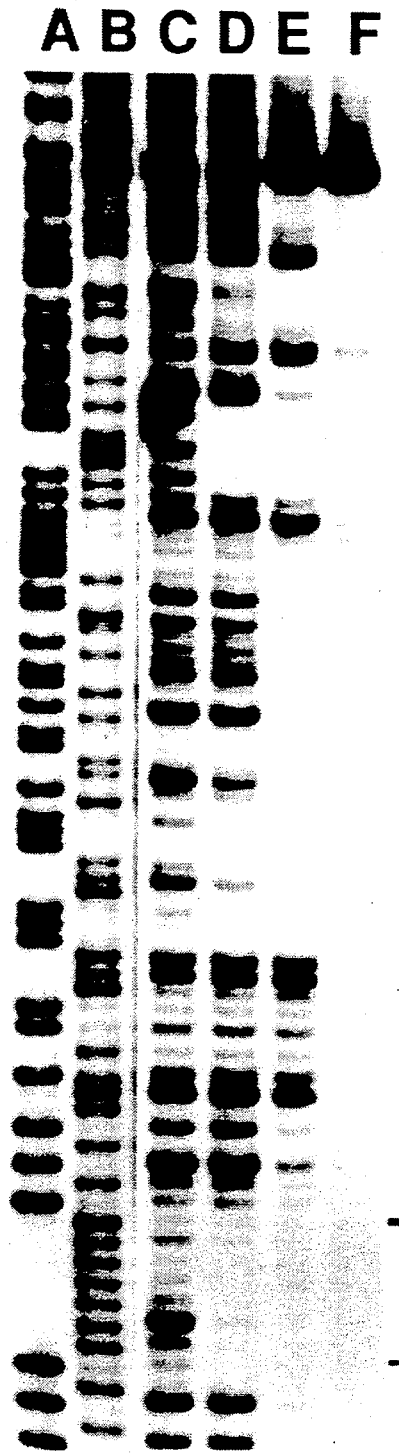
Figure 19D:

FIG. 19A to 19C: Comparison of distamycin footprinting by $Rh(phi)_2(bpy)^{3+}$ (a), MPE-Fe(II) (b), DNase I (c), and $Cu(phen)_2+$ (d). Footprinted regions of the T$_6$ tract are indicated by brackets. 3'-End-labeled fragment, 25 μMbp total DNA, and 12.5 μM metal complexes (Rh, Fe, and Cu) were used. (a) Lane A: Light control. Lane B: In the absence of distamycin. Lanes distamycin, respectively. Irradiation time was 7 min. (b) Lane A: in the absence of distamycin. Lanes B-H: in the presence of 0.125, 0.25, 0.50, 1.25, 2,5, 5,0, and 12,5 μM distamycin, respectively. I: in the absence of MPE. Incubation for DNA cleavage reaction was 5 min at 37° C. (c) Lanes A and B: Maxam-Gilbert A+G and T+C reactions, respectively. Lane C: In the absence of distamycin; D, E, and F: in the presence of 1.25, 5.0, and 25 μM distamycin, respectively. Incubation was 5 min at 37 ° C. in the presence of 0.2 units DNase I. (d) Lanes A and B: Maxam-Gilbert A+G and T+C reactions, respectively. Lane C: In the absence of distamycin. Lanes D, E, and F: in the presence of 1.25, 5.0, and 25 μM distamycin, respectively. Incubation was 13 sec at 37° C.

FIG. 20 Comparison of $Rh(phi)_2(bpy)^{3+}$ footprinting of EcoRI (a) with other footprinting techniques, MPE-Fe(II) (b) and DNase I (c). Footprinted regions are indicated by brackets. 3'-end-labeled fragment, 5 μM bp total DNA, and 5 μM metal (Rh or Fe) were employed. (a) Lane A: Intact DNA fragment. Lanes B and C: Dark control in the absence and presence (200 units) of EcoRI, respectively. Lanes D and E: light control in the absence and presence (200 units) of EcoRI. Lane F: in the absence of IEcoRI. Lanes G-J: in the presence of 50, 100, 200, and 300 units of EcoRI, respectively; Irradiation time was 5 min with a Hg/Xe lamp. Lanes K and L: Maxam-Gilbert A+G and T+C reactions. (b) Lane A: in the absence of EcoRI. Lanes B-E: In the presence of 50, 100, 200, and 300 units of EcoRI, respectively. Lanes F and G: DNA controls in the absence of MPE or Fe (II), respectively. Lanes K and L: Maxam-Gilbert A+G and T+C reactions. Samples were incubated at 37 µC. for 5 min. (c) Lanes A and B: DNA in the absence of EcoRI and DNase 1, Lane C: In the absence of EcoRI and in the presence of 0.2 units DNase I incubated at 37° C. for 2 min. Lanes D and E: In the presence of 64 units EcoRI and in the presence of 0.2 units DNase I incubated at 37° C. for 2 and 10 min, respectively. Lanes F, G, and H: In the presence of 252 units EcoRI and in the presence of 0.2, 0.8, and 1.6 units DNase I, respectively, incubated at 37° C. for 2, 10, and 10 min, respectively. Lanes I and J: Maxam-Gilbert A+G and T+C, reactions respectively.

Figure 21A:
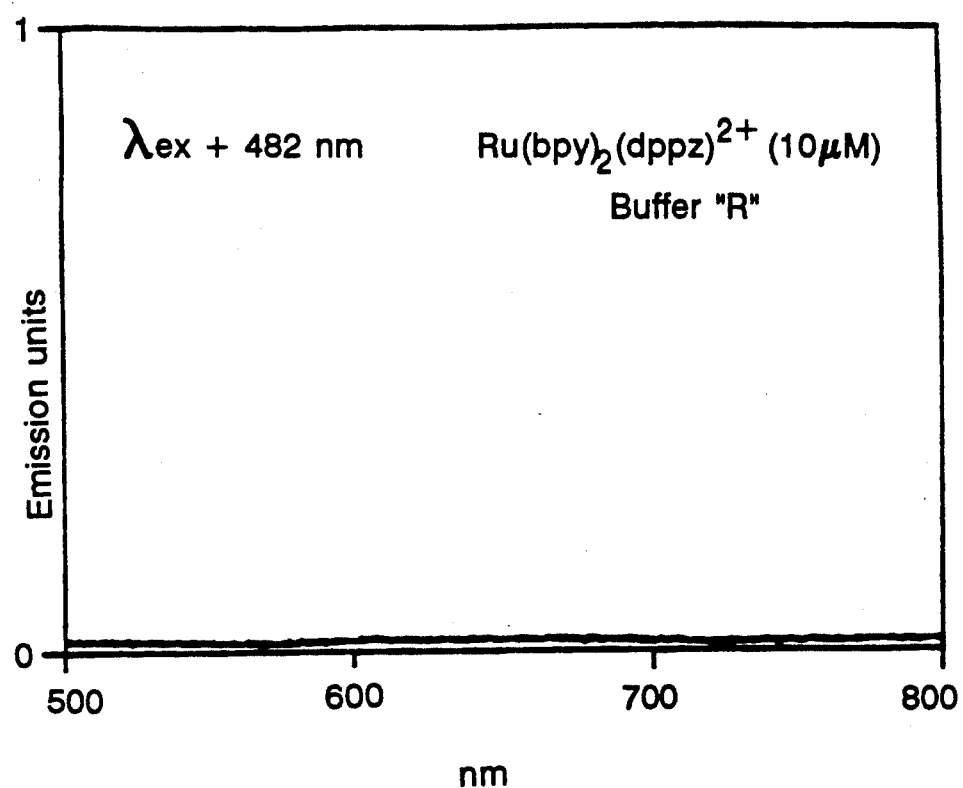
Figure 21B:
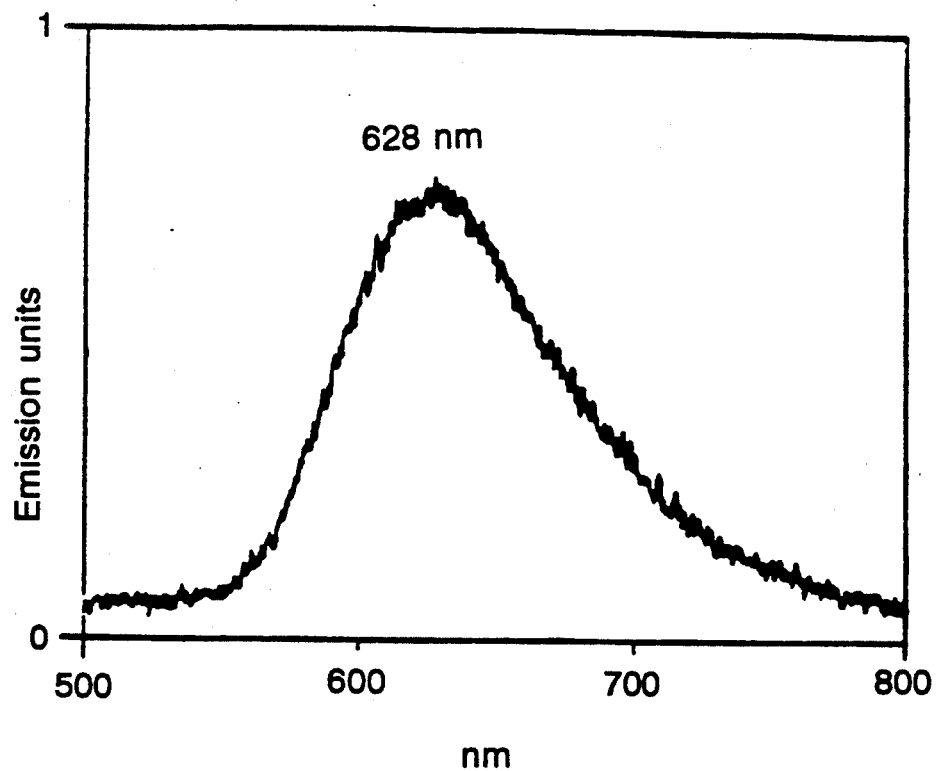
Figure 21C:
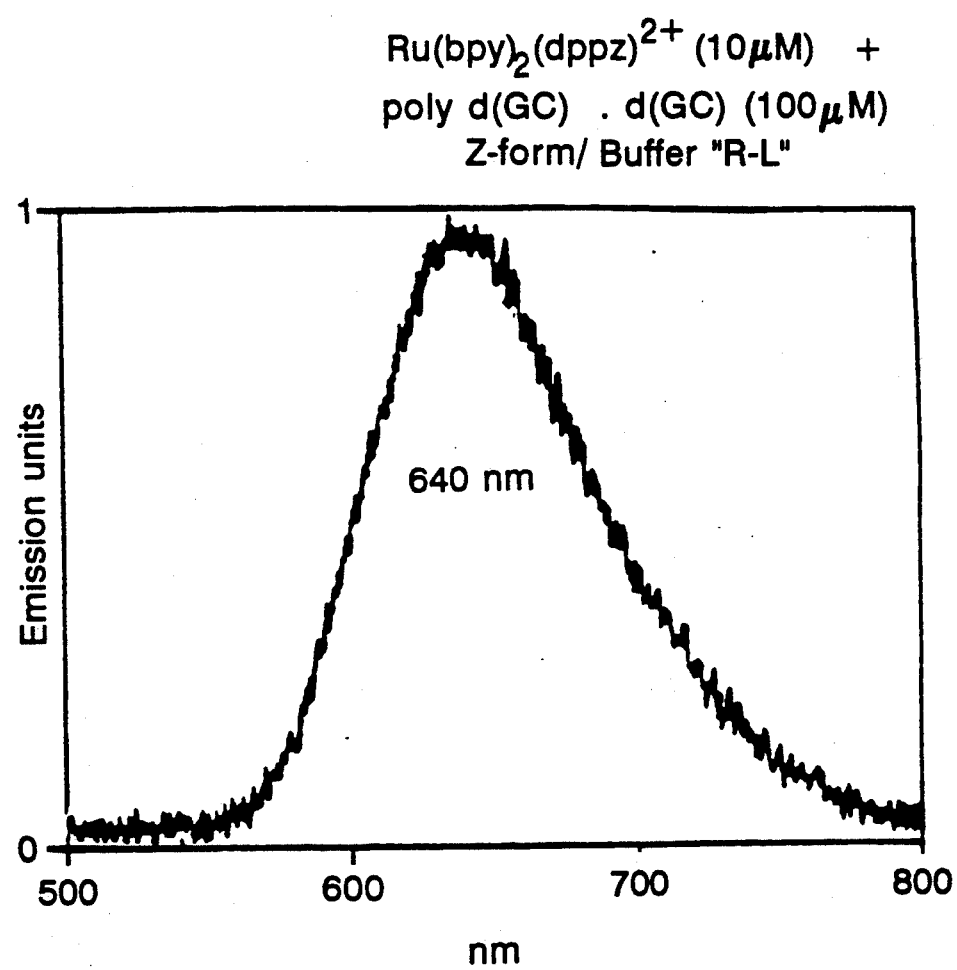

FIG. 21A to 21C: Luminescent Enhancement of Ru(bpy)$_2$(dppz)$^{2+}$ with B and Z-form DNA a. Ru(bpy)$_2$(dppz)$^{2+}$ 10 µM in buffer R=50.0 mM NaCl, 5.0 mM Tris-OH, pH=7.0. b. Ru(bpy)$_2$(dppz)$_2$ 10 µM in buffer R, with poly d(GC) d(GC) 100 µM under conditions providing B-form DNA. c. Ru(bpy)$_2$(dppz)$^{2+}$ 10 µM in buffer R-L=20.0 mM NaCl, 2.0 mM Tris-OH, pH 7.0, Co(NH$_3$)$_6$$^{3+}$4µM., with poly d(GC) d(GC) 100 µM under conditions providing Z-form DNA. All $\lambda_{ex}$=482 nm.

Figure 22:
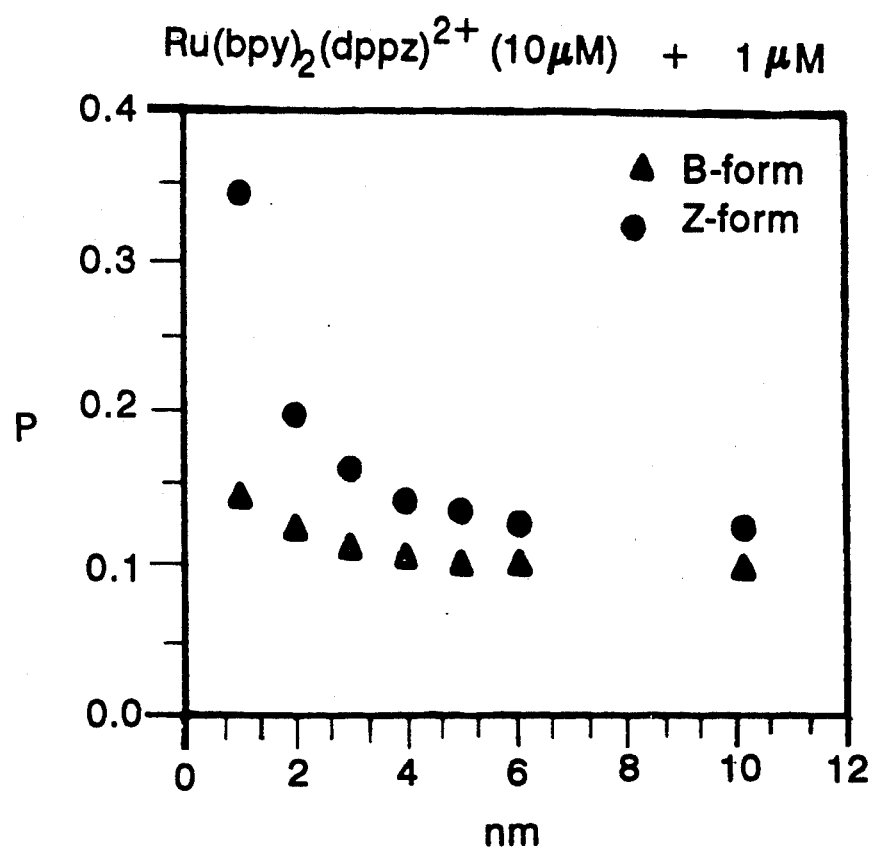
Figure 23:
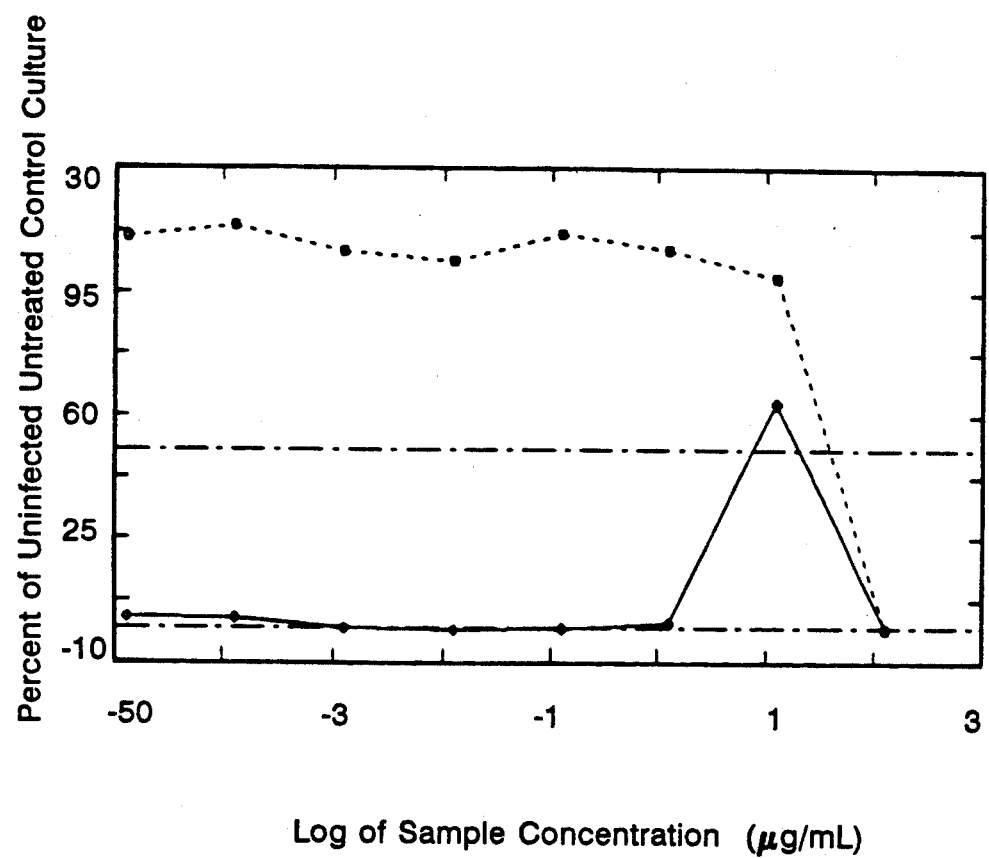
Figure 24:
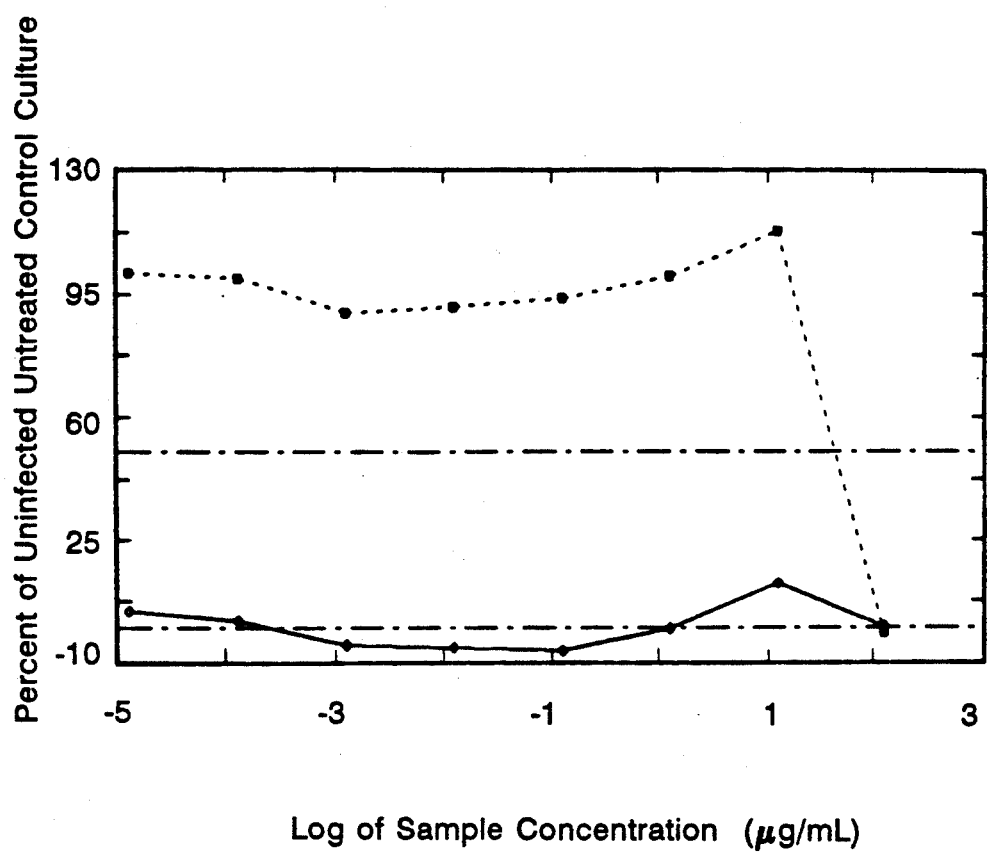
Figure 25:
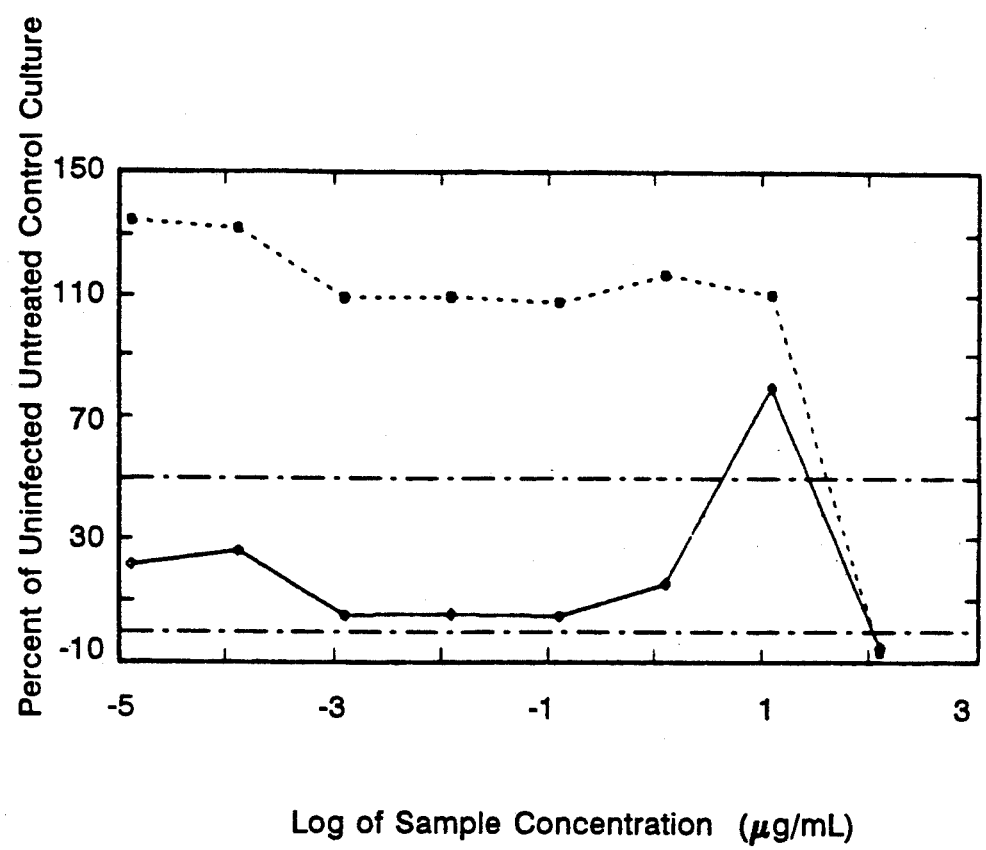
Figure 26:
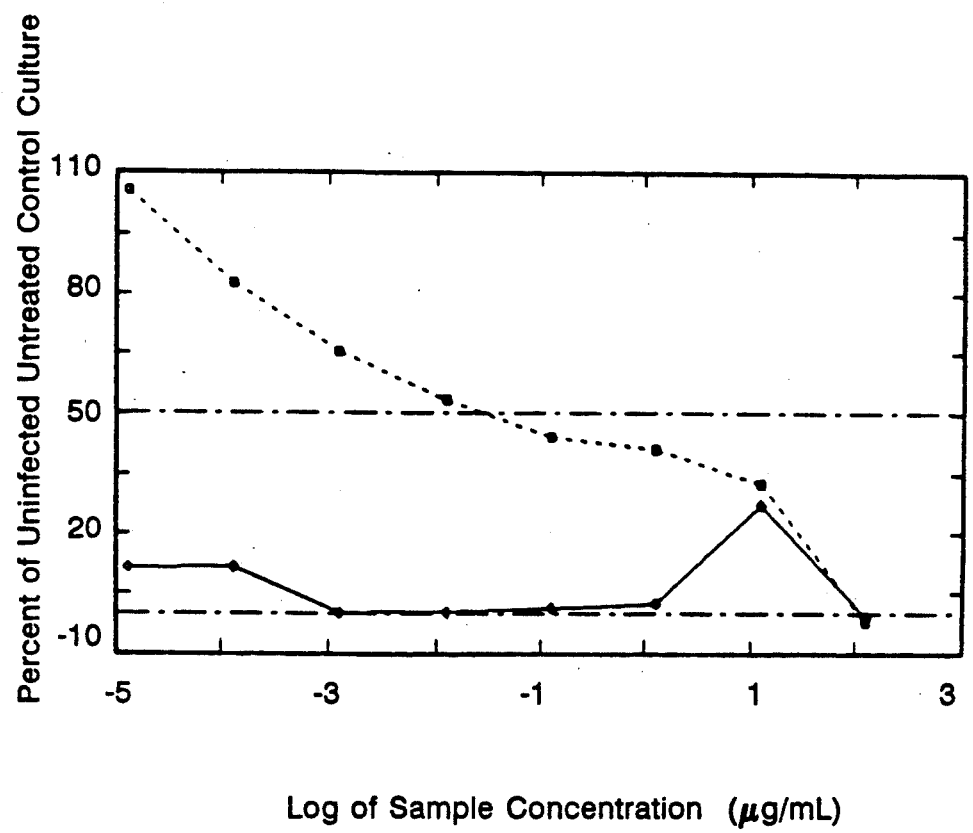
Figure 27:
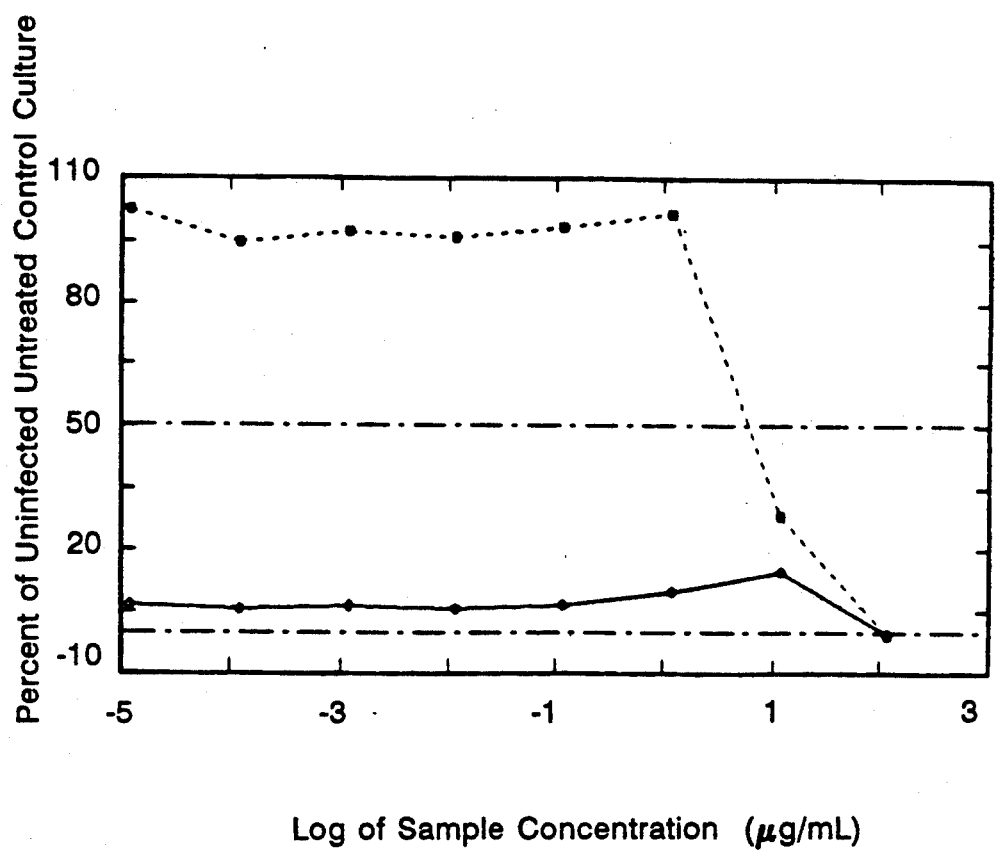
Figure 28:
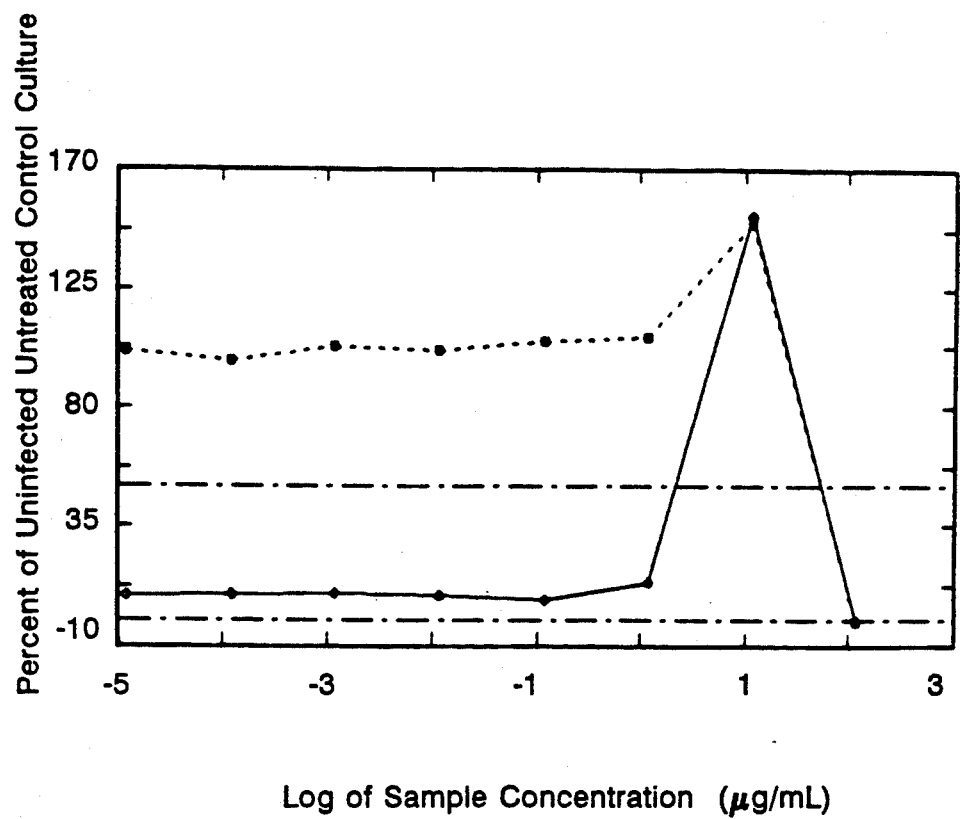
Figure 29:
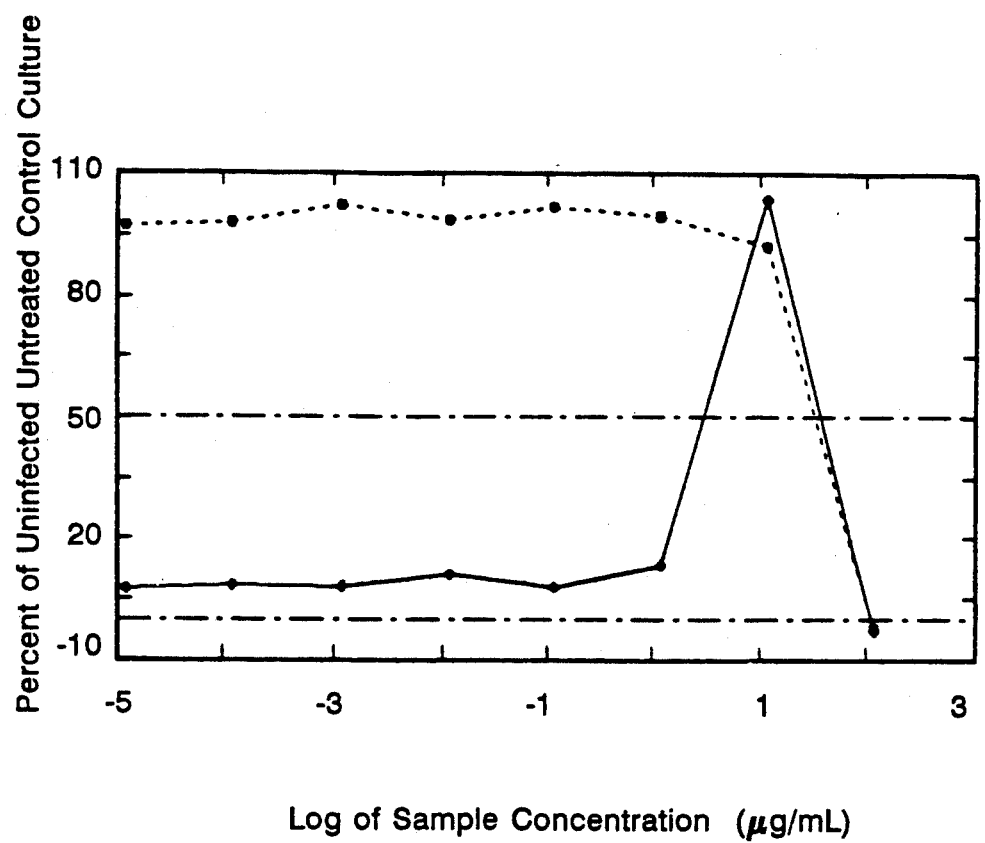
Figure 30:
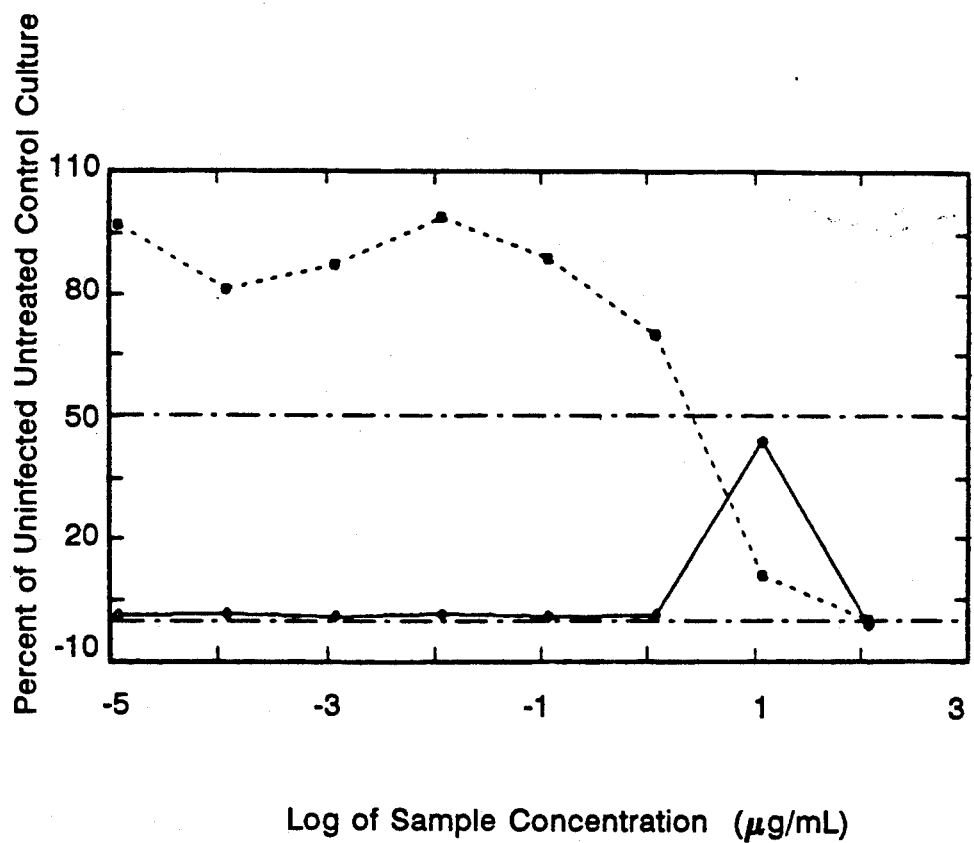
Figure 31:
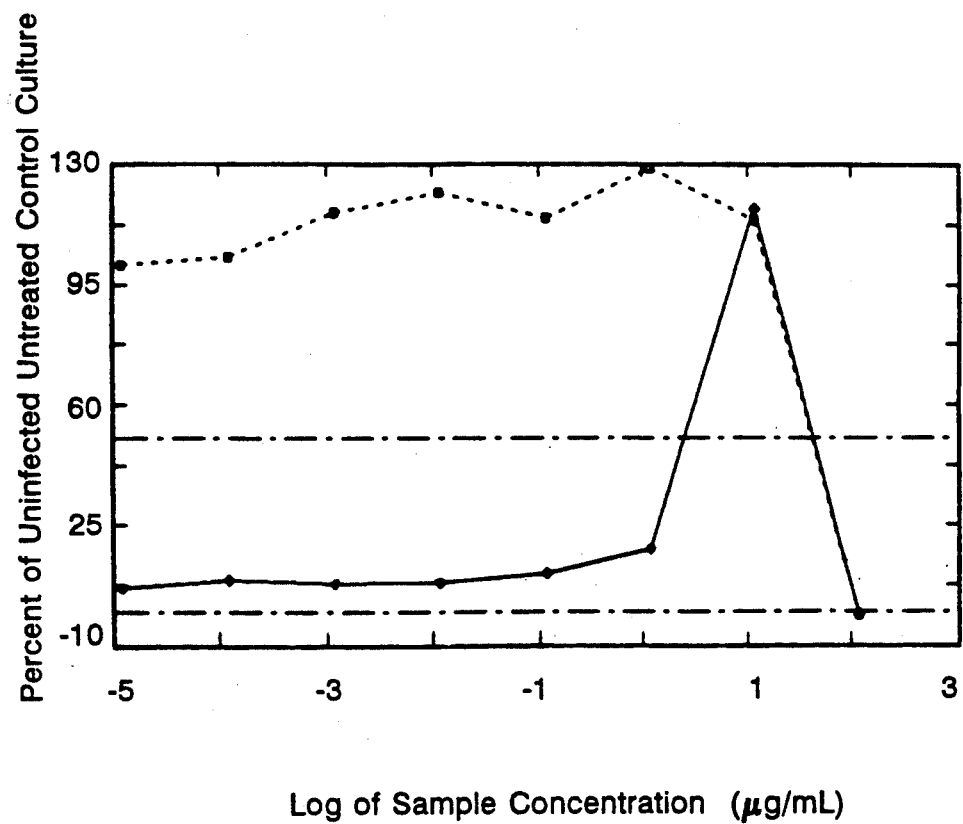
Figure 32:
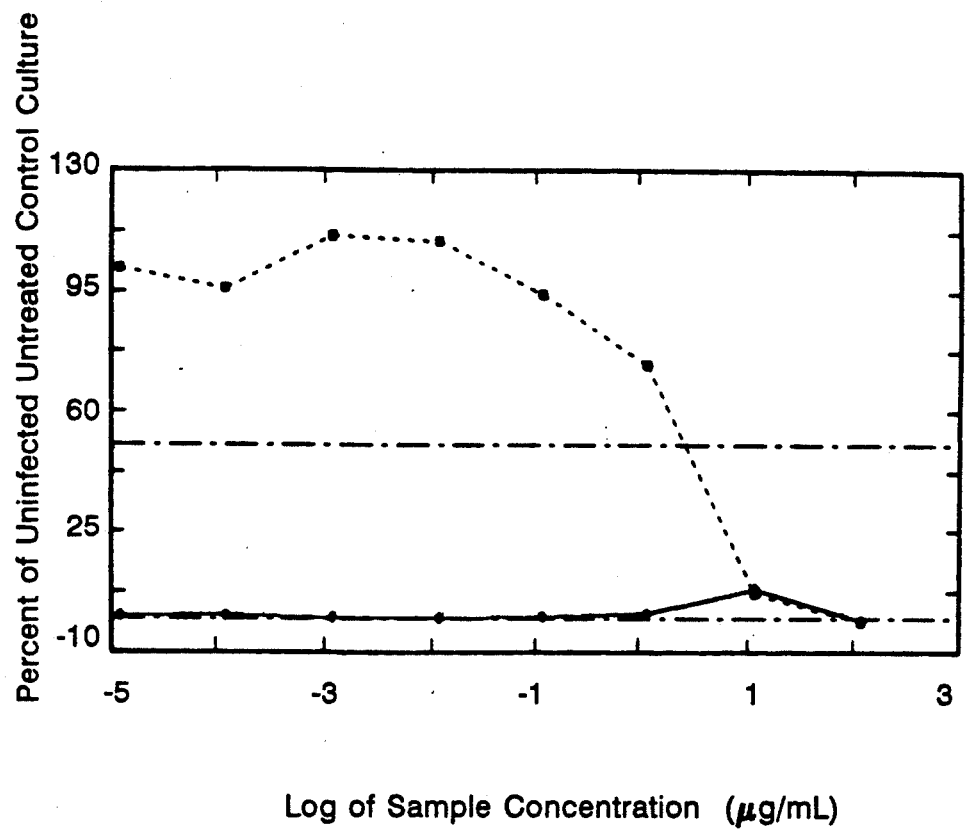
Figure 33:
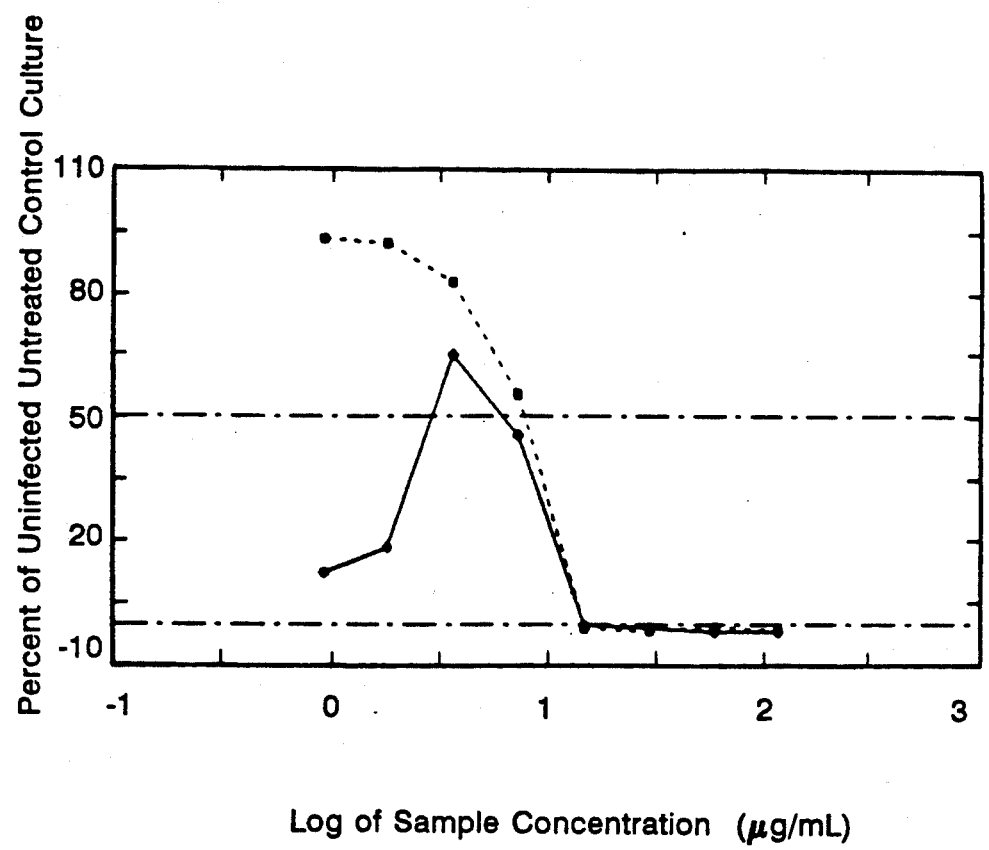

FIG. 22 Steady State Polarization of Ru(bpy)$_2$(dppz)$^{2+}$ with B and Z-form DNA Under the conditions that provide B-form (lower curve) DNA the highest measured polarization is 0.15 with a limiting polarization 0.10. Under the conditions that provide Z-DNA (upper curve) the highest polarization is 0.35 with a limiting polarization of 0.14. Ru(bpy)$_2$(dppz)$^{2+}$ 10 µM, poly d(GC) d(GC) 100 µM, $\lambda_{ex}$=482 nm.

FIGS. 23-33 In vitro anti-HIV drug screening results of Rh(DIP)$_3$. The figures plot percent of uneffected untreated control culture against Log of Sample Concentration (µg/mL) The -.-.- lines are 0% and 50% Reference lines, . . . lines is Viral Cytopathic Effect, —$_{13}$ line is infected Treated culture — line is uneffected treated culture.

DETAIL DESCRIPTION OF THE INVENTION

This invention concerns a coordination complex or salt thereof which is sepectoscopically or photoactively determinable when bound to the DNA having the formula

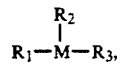

wherein M is a suitable transition metal and each of R$_1$, R$_2$ and R$_3$ is ethylenediamine or a substituted derivative therof, bipyridine or a substituted derivative thereof, phenanthroline or a substituted derivative thereof, diazafluorene-9-one or a substituted derivative thereof, or phenanthrenequinonediimine or a substituted derivative thereof or dipridophenazine or a substituted derivative thereof; wherein R$_1$, R$_2$ and R$_3$ are bound to M by coordination bonds and wherein R$_1$ and R$_2$ are the same or different but if the same are different from R$_3$. Suitable transition metals include ruthenium(Ru), rhodium(Rh), cobalt(Co), iron(Fe), chromium(Cr), copper(Cu), zinc(Zn), cadmium(Cd), or lead(pb). To date, ruthenium, rhodium and cobalt have proven to be the most effective. Preferred groups for R$_1$, R$_2$ and R$_3$ are 2,2'-bipyridine(bpy), 1,10-phenanthroline(phen), 4,5-diazafluorene-9-one(flone), 9,10-phenanthrenequinonediimine(phi), 4,7-diamino-1,10-phenantholine; 3,8-diamino-1,10-phenanthroline; 4,7-diethylenediamine-1, 10-phenanthroline; 3,8-diethylenediamine-1,10-phenanthroline; 4,7-dihydroxyl-1,10-phenanthroline; 3,8-dinitro-1,10-phenanthroline; 4,7-diphenyl-1,10-phenanthroline (DIP); 3,8-diphenyl-1,10-phenanthroline; 4,7-dispermine-1,10-phenanthroline; 3,8-dispermine-1,10-phenanthroline; 5-nitro-phenanthroline (5-NO$_2$phen); 3,4,7,8-tetramethyl-phenanthroline (TMP), 4,4'diphenyl bipyridine; bis 4,4'methyl bipyridylate and bis 4,4'bipyridylamide, 3,2 dipridophenazine (DPPZ).

In the preferred embodiments of the invention the complex has the formula M(phen)$_2$(phi), M(bpy)$_2$(phi), M(phi)$_2$(bpy), M(phi)$_2$(4,4'diphenyl bipyridine), M(bis 4,4'methyl bipyridylate)$_2$(phi), M(bis 4,4'bipyridylamide)$_2$(phi), M(bpy)$_2$(phen), M(phen)$_2$(bpy), M(phen)$_2$(flone), M(bpy)$_2$(DIP), M(phen)$_2$(DIP), M(ethylenediamine)$_2$(phi), M(phi)$_3$, M(5-NO$_2$phen)$_3$ or M(DIP)$_2$(phen) M(bpy)$_2$(dppz), M(phen)$_2$(dppz), M(DIP)$_2$(dppz) or M(dppz)$_2$phen wherein M is Ru, Rh or Co.

Especially preferred are the following complexes: Ru(bpy)$_2$(phen)$^{2+}$, Ru(phen)$_2$(bpy)$^{2+}$, Ru(phen)$_2$(flone)$^{2+}$, Ru(bpy)$_2$(DIP)$^{2+}$, Ru(phen)$_2$(DIP)$^{2+}$, Ru(DIP)$_2$(phen)$^{2+}$, Ru(phi)$_2$(bpy)$^{2+}$, Ru(phen)$_2$(phi)$^{2+}$, Ru(bpy)$_2$(phi)$^{2+}$, Rh(phi)$_2$(bpy)$^{3+}$, Rh(phen)$_2$(phi)$^{3+}$, Rh(phi)$_2$(4,4'diphenyl bipyridine)$^{3+}$, Rh(bis 4,4'methyl-bipridylate)$_2$(phi)$^{3+}$, Rh(bis 4.4'bipyridylamide)$_2$(phi)$^{3+}$, Ru(bpy)$_2$(dppz)$^{2+}$(dppz)$_2$, Ru(dip)$_2$dppz, Ru(phen)$_2$dppzz$^{2+}$, Ru(dppz)(bpy)$^{2+}$, Ru(dppz)$_2$(phen)$^{2+}$.

Also, the invention concern a coordination complex or salt thereof which is spectroscopically or photoactively determinable when bound to DNA having the formula

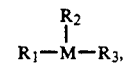

wherein M is a suitable transition metal and each of R$_1$, R$_2$ and R$_3$ is ethylenediamine or a substituted derivative thereof, bipyridine or a substituted derivative thereof, phenanthroline or a substituted derivative thereof, diazafluorene-9-one or a substituted derivative thereof, or phenanthrenequinonediimine or a substituted derivative thereof, dipyridophenazine or a substituted derivative thereof; wherein R$_1$, R$_2$ and R$_3$ are bound to M by coordination bonds; provided that at least one of R$_1$, R$_2$ or R$_3$ is dipyridophenazine or a substituted derivative thereof.

The invention also concerns the complex

wherein M is Ru or Rh and R is 9-10-phenanthrenequinonediimine, 5-nitro-phenanthroline or 3,2-dipyridophenazine or a substituted derivative thereof.

Further, the invention concerns the optically resolved delta and lambda isomers of the complex. It has unexpectedly been found that the complex or the delta or lambda isomer of the complex binds and labels DNA. More specifically, the complex or isomer of the complex binds and labels specific conformations of DNA preferentially, i.e. A-DNA, Z-DNA, B-DNA or cruciforms of DNA. The complexes bind to DNA by intercalation or surface binding by means of hydrogen bonding or weak Van der Waals interactions. The method of labeling DNA or specificically labeling a conformation on DNA is effected by contacting the DNA with the complex of the present invention (or an isomer) so that the complex binds to the DNA, preferably at the conformation, thereby labeling the DNA or conformation. The method of labeling may be used to detect the presence of a conformation present in double stranded DNA by selectively labeling the conformation and then detecting the presence of the bound complex or the isomer of the complex. The complex may be detected by spectroscopic methods or photoactive means.

The invention also concerns a labeled DNA probe which comprises the complex covalently bound to the DNA probe. The invention also concerns a method of detecting the presence in a sample of a target DNA of interest which comprises contacting the sample containing the target DNA with a complementary labeled DNA probe under hybridizing conditions and measuring the resulting luminescence emitted from the labeled DNA probe a change in the luminescence indicating the presence of the target DNA.

By this method, a target DNA sequence is contacted with a complementary labeled DNA probe to bind to the target DNA sequence as is known in the art. The luminescence is measured by conventional methods and a change in luminescence emitted from the labeled DNA probe indicates the labeled DNA probe is bound to the target DNA sequence.

Still another embodiment of this invention is a method for nicking double stranded DNA by effecting single stranded scission, i.e. breakage of at least one phosphodiester bond along the DNA. The method preferable involves contacting the DNA within a cobalt or rhodium containing the DNA with a cobalt or rhodium containing complex of the invention under suitable conditions such that the complex binds to the DNA so as to form a adduct and irradiating the adduct so form with visible light or ultraviolet radiation of an appropriate wavelength so as to nick the DNA at the site of binding. An appropriate visible or ultraviolet wavelength in this and other embodiments of the invention is a wavelength which is absorbed by the complex used. As described hereinafter, the ligand band absorption of a complex of this invention may be determined spectroscopically by conventional methods. It is also contemplated that the method for nicking DNA may be preformed in vivo.

The invention further involves a method of cleaving double stranded DNA which comprises nicking the DNA by the above-mentioned method and treating the nicked DNA so produced with a suitable enzyme capable of cleaving single stranded DNA under conditions effective to cleave the nicked, double stranded DNA at the site of the nick. By this method double stranded scission of the DNA is effected. Suitable enzymes for effecting double stranded cleavage of nicked DNA in this and other embodiments includes those which are not deactivated in the presence of the complex used for DNA nicking, e.g. S1 nuclease. It is further contemplated that this method for cleaving DNA may also be performed in vivo. The invention also involves a method for selectively nicking or selectively cleaving DNA at a specific conformation by using the complex or an isomer of the complex such as delta and lambda enantiomer. Appropriate conformations at which the complex may be used to nick or cleave the DNA include Z-DNA, A-DNA, B-DNA or cruciforms of DNA.

It is also contemplated that the complex may be used for labeling, detecting, nicking, or cleaving other forms of double stranded polynucleotides such as double stranded RNA and double stranded DNA-RNA hybrids.

Further, it is contemplated a method for footprinting a labeled DNA fragment comprising binding the complex to the labled DNA fragment and irradiating the complex so as to cleave the labeled DNA at the site of binding of the complex to the labeled DNA fragment to produce a footprint of the binding site. It is further contemplated that the method for footprinting comprises binding of the complex by intercalation. Also, the binding occurs in major as well as minor grooves.

Lastly, the invention provides a method of killing a portion of a population of appropriate tumor cells. The method involves contacting the tumor cells under suitable conditions with an effective amount of the complex or an isomer of the complex to kill the tumor cells. The method may further comprise irradiating the tumor cells with visible light or ultraviolet radiation of an appropriate wavelength at a suitable time after the tumor cells have been contacted with the complex, thereby permittng the complex to nick the DNA of the tumor cells. The method may be used for the treatment of a subject afflicted with tumor cells so as to cause regression of the tumor cells. Administration of the complex to the subject may be parenteral, oral, or topical.

Lastly, the invention concerns a method for treating a subject afflicted with a human immuno deficiency virus which comprises administering to the subject an amount of Rh (DIP)$_3$ so as to inhibit the activity of the virus.

EXPERIMENTAL DETAILS

I. Synthesis and Characterization of Ru(phi)$_3^{+2}$ and Zn(phi)$^{+2}$:

Ligand Synthesis. 9, 10-Phenanthrenequinone bis((trimethylsilyl)-imine) (silylphi) was synthesized from 9,10-phenanthrenequinone (Aldrich) and sodium bis(trimethylsilyl)amide (Fluka) as described by Tuchtenhagen and Ruhlmann. (55) Important modifications to this synthesis include a reaction temperature of no greater that 65° C. and a final phenanthrenequinone concentration of 0.08M. Under these conditions, orange crystalline silylphi was obtained in 37% yield and stored under nitrogen. The phenanthrenequinone diimine ligand (phi) was generated and chelated in situ by combining the silylated imine ligand with an ethanolic solution of metal chloride by using a modification of Schlosser's method. (56)

[Ru(phi)$_3$]Cl$_2$. A 1.025-g sample of 9, 10-phenanthrenequinone bis((trimethylsilyl)imine (2.9 mmol) dissolved in 75 mL benzene was added to a vigorously stirring suspension of Ru(DMSO)$_4$Cl$_2$ (Alfa Products; 0.355 g, 0.73 mmol) in 25 mL of EtOH and 75 mL of Benzene. All solvents were dried and distilled under nitrogen before use. This mixture was heated at 65° C. for 1 h until a rich purple solution was generated. The reaction vessel was then opened to the air. After the crude reaction mixture was filtered, it was cooled and evaporated to a small volume. Ru(phi)$_3$Cl$_2$ was precipitated with diethyl ether and collected on a frit.

Solid [Ru(phi)$_3$]Cl$_2$ was washed with acetone to remove several blue byproducts (57) and then diethyl ether to remove organic material resulting from in-air decomposition of excess ligand. After several diethyl ether precipitations from ethanol solutions, Ru(phi)$_3$]Cl$_2$ was washed with H$_2$O to give a final yield of 51%. Samples were often further purified by cellulose column chromatography.

The $^1$H NMR spectum of [Ru(phi)$_3$]Cl$_2$ is indicative of a symmetrical, D$_3$metal chelate with resonances at 7.6 (2H, tiplet), 8.22 (1H, doublet, 8.8 (1H, doublet), and 14.2 ppm (1H, singlet imine). This is confirmed by elemental analysis. Anal. Calcd for Ru(phi)$_3$Cl$_2$.H$_2$O: C, 62.38; H, 3,99: N, 10.39; Ru, 12.90. Found C, 62.29: H, 4.21: N, 10.0: Ru, 13.10. Fast atom bombardment (FAB) mass spectroscopy of [Ru(phi)$_3$]Cl$_2$ showed a strong Ru(phi)$_3$$^{2+}$ molecular ion of Mr 719 with the next largest peak being the Ru(phi)$_2$$^{2+}$ fragment at M, 514. Infrared spectroscopy revealed characteristic imine N-H stretches at 3274 and 3167 cm$^{-1}$ and a C=N stretch at 1497 cm$^{-1}$.

Zn(phi)Cl$_2$. The zinc complex was synthesized as described for [Ru(phi);]Cl$_2$. Yellow Zn(phi)Cl$_2$ was filtered directly out of the reaction mixture in quantitative yield and washed with diethyl ether, H$_2$O, and acetone. Anal. Calcd for Zn(phi)Cl$_2$.1/3C$_6$H$_6$: C, 52.15;H, 3.29; N, 7.60; Cl, 19.23. Found: C, 52.14;H, 3.71; N, 7.21; Cl, 18.50. The molecular ion by FAB was the Zn(phi)Cl cation of M$_1$307 as expected for the proposed structure.

The $^1$H of Zn(phi)Cl$_2$ is slighty complicated by the fact that it dissolves only in coordinating solvents such as DMSO or DMF. Upon dissolution, the tetrahedral structure changes to octahedral as two molecules of solvent bind cisoid to the metal center. The resulting species has several isomers and a Cl symmetry that renders each proton nonequivalent. Although imine protons are especially affected by the different steric environment of the isomers, there is an integral of two imine protons for each eight aromatic protons. C—H resonances in DMF: 8.52 (1 H, doublet), 8.36 (1H, doublet), 8.21 (2H, multiplet), 7.74 (1H, triplet), 7.55 (2H, triplet), 7.39 ppm (1H, mult). N—H resonances: 12.35 (1H, s), 12.0 ($\frac{1}{3}$H, s), 11.8 ($^1$/3H, s) 11.6 ppm ($\frac{1}{3}$H, s).

Instrumentation. Ultraviolet-visible absorption experiments were performed by using a Varian-Cary 219 spectrophotometer and $^1$H NMR measurements on a Varian VXR-300 spectrometer. Cyclic voltammetry was condited by using an IBM voltamograph and recorder. Flash photolysis experiments were made witn a YAG laser, monitored with an optical miltichannel analyzer interfaced to a PDP 11/23.

II. [(Rh(Phi)$_2$(bpy)]Cl$_3$

[Rh(Phi)$_2$(bpy)]Cl$_3$ was synthesized as described previously (17) and MPE was provided by Prof. P. B. Dervan. Distamycn A, alkaline phosphatase, bovine serum albumin, and 2,9-dimethyl-1 10-phenanthroline were obtained from Sigma; lyophilized EcoR I, HindIII, PVuII, terminal deoxynucleotidyl transferase and T4 polynucleotide kinase from BRL; DNase I from Boehringer Manheim; dithiothreitol, 3-mercaptopropionic acid, and 1,10-phenanthroline from Aldrich; and α-$^{32}$P-3'-dATP and γ-$^{32}$P-dATP from NEN. Tris-acetate buffer for irradiations with Rh(phi)$_2$(bpy)$^{3+}$ contains the following unless specified otherwise: 50mM tris, 20 mM sodium acetate, 18 mM NaCl, pH 7. Loading buffer for electrophoresis on a denaturing polyacrylamide gel contains 80% formamide, 50 mM tris borate buffer (pH 8), 0.1% xylene cyanol, 0.1% bromophenol blue, 0.1N NaOH, and 1 mM EDTA. Polyacrylamide Gel-Mix 8 from BRL was used for puring denaturing polyacrylamide gels.

Preparation of Labeled DNA fragment

Plasmid pJT18-T6 is obtained by inserting an 18 base pair oligonucleotide (5'-ATATGCAAAAAAG-CATAT-3') into the Sma I site of plasmid pUC 18 and amplifying in E. coli (JM109) cells by culture. The plasmid was isolated according to literature methods (19). The plasmid thus obtained was first digested with restriction enzyme Hind III and purified by ethanol precipitation. To obtain 3'end-labeled fragment, $^{32}$P-α deoxy-ATP and terminal deoxynucleotidyl transferase were reacted with linearized DNA. This was followed by a second digestion with Pvu II, yielding a 245 bp DNA fragment which was prufied on a 5% polyacrylamide gel and isolated by subsequent electrophoretic elution. The DNA fragment was then ethanol precipitated n the presence of sodium acetate and washed with EtOH. After lyophilization, the DNA fragment was dissolved in 1/10 dilution tris-acetate buffer containing 0.1 mM EDTA for use or storage at 4° C. To obtain 5'end-labeled fragment, linearized DNA was treated with alkaline phosphatase and labeled with $^{32}$P-γ ATP in the presence of polynucleotide kinase. Fragment isolation and purification were performed as described for 3'end-labeled fragment.

DNA Cleavage by Rh(phi)2(bpy)3PMA

A typical procedure for carrying out DNA photocleavage with Rh(phi)$_2$(bpy)3+ is as follows: 50 μl of a reaction mixture containing 32P-end labeled DNA fragment (5 μM bp and approx 30,000 cpm, concentration adjusted with calf thymus carrier DNA), and 5 μM [Rh(phi)$_2$(bpy)]Cl$_3$(ε350=23,6000 M$^{-1}$cm$^{-1}$) in tris-acetate buffer is added to a 1.7 ml presiliconized polypropylene tube. Open reaction tubes are fixed such that the reaction mixture is directly in the focal point of a 1000 W Hg/Xe lamp beam focused and filtered with a monochrometer (Oriel model 77250) and a glass filter to eliminate the light below 300 nm. Samples are irradiated at 310 nm for approximately 5 minutes. After irradiation, 1 μl of −3μg/μl calf thymus DNA and 25 μl of 7.5M ammonium acetate are added to the reaction mixture, which is then heated at 90° C. for 5 min and precipitated by addition of 150 μl EtOH. The DNA pellet is rinsed with 70% ethanol and then lyophilized. After addition of 2.5 μl loading buffer, the samples are electrophoresed on an 8% denaturing polyacrylamide gel.

Rh(phi)2(bpy)$^{3+}$ Footprinting of Distamycin and EcoRI

Distamycin-A was dissolved in deionized water and the concentration of stock solution was determined optically, using ε$_{302\ nm}$=3.4×104 M$^{-1}$cm$^{-1}$(20). Final reaction mixtures in trisacetate buffer contained 0.125-25 μM distamycin, 25 μM bp $^{32}$P-end labeled fragment DNA (nucleotide concentration adjusted with calf thymus DNA carrier) and 12.5 μM [Rh(phi)₂(bpy)]Cl₃. After addition of distamycin to DNA, the solution was allowed to stand at room temperature for 10 minutes before addition of the rhodium complex. This was followed by another 15 minute room temperature incubation before irradiation as described above. For EcoRI footprinting, EcoRI was dissolved to a final concentration of 40 units/μl in tris-acetate buffer containing 0.1 mM calcium chloride and left at 0 °C. for 1 hour (one pmole of the endonuclease corresponds to 769 units, by assuming that the turnover number of the enzyme is 4 per hour per dimer (21). The final reaction mixture in tris-acetate buffer contained 60-360 units of EcoRI, 5 μM bp ³²P-end labeled fragment DNA (nucleotide concentration adjusted with pUC18 carrier), 1 mM calcium chloride (necessary to displace traces of $Mg^{2+}$ in the enzyme (18)), and 5 μM $Rh(phi)_3(bpy)^{3+}$. DNA and EcoRI were incubated together for 30 minutes, then again for 15 minutes after the addition of $Rh(phi)_2(bpy)^{3+}$. Following irradiation, the reaction mixture was ethanol precipitated in the presence of ~4 μg DNA, followed by phenol/chloroform extraction, and another ethanol precipitation.

$Rh(phi)_2()bpy)^+$ Footprinting of EcoRI Using a Transilluminator

The reaction mixture was prepared as described above. 50 μl irradiation volumes are then placed in "short tubes" (capless 1.7 ml presiliconized polypropylene tubes cut down to small cups approximately 7 mm high and 100 μl in volume, to minimize the distance between reaction mixtures and the UV-light source), which are placed in a pipette-tip rack and irradiated by inverting a UV transilluminator (Spectroline Model #TR₃₀₂ for visualizing ethidium-stained agarose gels) on top of them. The UV-filter of the transilluminator may be removed to increase light intensity. Samples should be less than 1 cm from the light source and irradiated for 20 min at room temperature. Work-up is the same as described previously.

Footprinting with other reagents

Footprinting reactions for distamycin and EcoRI were conducted using DNA binding ligands at comparable concentrations to those employed for the rhodium complex (described above), but using cleavage methodologies for DNase, I, MPE-Fe(II) and Cu(Phen)₂+ according to the literature (1,2,4,9,22).

Electrophoresis, Autoradiography, Densitometry and Data Processing

DNA pellets from the footprinting reactions were dissolved in 2.5 μl loading buffer and electrophoresed on an 8% denaturing polyacrylamide gel as described (19). Reaction products were coeletrophoresed with Maxam-Gilbert sequencing reactions (23). After removal from plates gels were dried and subjected to autoradiography (Kodak, X-OMAT ™ AR) at room temperature (or −60° C.) without an intensifying screen for 2-20 days. Autoradiographs were scanned on a 2202 Ultra Scan Laser Densitometer (LKB). To obtain the integrated intensity (I) of each peak, the integrated area of the light-control or DNA -control (for other footprinters) was subtracted. The resulting $I_d$ or $I_e$ (corrected integrated intensity in the presence of distamycin or EcoRI, respectively) was then subtracted from $I_c$ (the integrated intensity in the absence of distamycin or EcoRI) and reported as a normalized ratio. The final value of $(I_c-I_d)/I_c$ or $(I_c-I_e)/I_c$ for given band is then equal to 1 for complete footprinting, 0 for total absence of footprinting and a negative value for enhanced cleavage in the presence of distamycin or EcoRI.

III. Ligand and Metal Complex Syntheses

Preparations of $Ru(bpy)_2(dppz)^{2+}$ (10 μM) in buffer R[40] and buffer R-L[41] (pH 7.0) produced species that were nonluminescent solutions (FIG. 21a) ($\lambda_{irr}$=482 nm). However, when $Ru(bpy)_2(dppz)^{2+}$ (10 μM) was mixed with 100 μM, poly d(GC) d(GC) (buffer R-L) the solution was highly luminescent ($\lambda_{irr}$=432 nm) and produced a $\lambda_{max}$=640 nm (FIG. 21c) under conditions that are consistent with forming Z-DNA. Luminescent behavior such as this can be attributed to a highly intercalated species. This must be due to the complex being bound to the Z-form and not due to lower salt conditions (or added $Co(NH_3)_6^{3+}$) as the under the same Z-form producing conditions, calf thymus DNA produces the expected B-form luminescence. Unlike other intercalating species Such as ethidium-Br[42], $Ru(bpy)_2(dppz)^{2+}$ does not cause the Z to B transition as solutions of the complex $Ru(bpy)_2(dppz)^{2+}$ with Z-form DNA are stable over hours as shown by circular dichroism.

To further test the extent of intercalation of this complex a study of the steady state luminescence polarization of the complex bound to each form of DNA was made. These experiments give information on how rigidly the complex is held by the DNA. FIG. 22, curve A shows the effect of adding 1 μM probe (100 μM DNA) the highest luminescence polarization was observed for this solution (0.15). This reflects a situation where the complex is completely bound to the right-handed helix. As the concentration of $Ru(bpy)_2(dppz)^{2+}$ increases, the polarization decreases to limiting value (0.10) at a complex:base pair ratio of 1:10. Further, addition of $Ru(bpy)_2(dppz)_{2+}$ produces the same polarization value, we therefore surmise that the helix becomes saturated and the unbound complex does not contribute to the polarization value.

Figure 1:
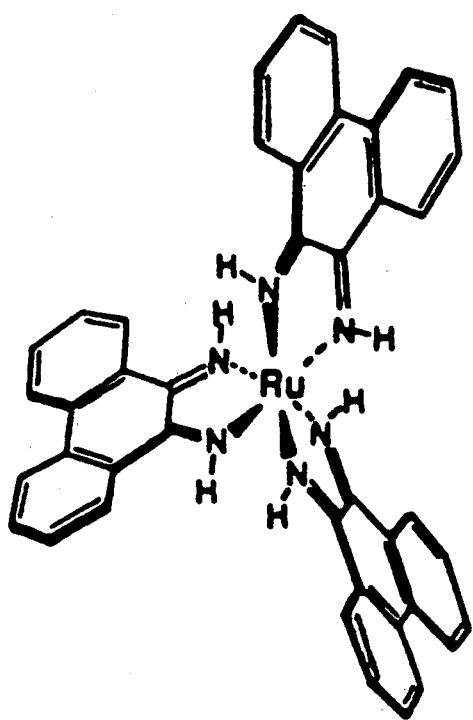
FIG. 1: Ru(phi)$3^{2+}$.

FIG. 1 shows the luminsecent enhancement with B and Z form DNA. The results show the Z-form has a higher emission of 640 nm compared to 628 nm for the B form.

5-Amino-1,10-phenanthroline. A magnetically stirred solution of 5nitro-1, 10-phenanthroline (2,.01 g, 8.93 mmol) and tin(II) chloride dihydrate (6.05 g, 26.81 mmol) was heated to reflux for 3 h in ethanol (100 mL) and then concentrated in vacuo to give a viscous residue. The residue was treated with concentrated NaOH and then extracted with $CHCl_3$ (3×50 mL). The organic layer was separated, washed with water (2×50 mL) and brine (1×50 mL), dried over anhydrous sodium sulfate, and then concentrated in vacuo to afford 1.08 g (62%) of the amine as a tan solid: m.p. 255-258 C; MS(fab):m/e 196 (MH+).

1,10-Phenanthroline-5,6-cuinone. A magnetically stirred mixture of 5-amino-1,10-phenanthroline (2.88 g, 14.75 mmol) in cold $H_2SO_4$ (ca. 20 mL) was treated with concentrated $HNO_3$ (10 mL). The brown colored solution was warmed to 100° C. for 2.5 h, cooled to room temperature, and then poured over cracked ice (ca. 150 g). The acidic solution was neutralized with concentrated NaOH and then extracted with $CHCl_3$ (3×100 mL). The organic phase was washed with water (4×100 mL) and brine (1×100 mL), dried over anhydrous sodium sulfate, and then concentrated in vacuo to give about 1.6 g (52%) of the quinone as a rusty orange powder: m.p. 260° C.; MS (fab): m/e 212 (MH+—); uv-vis (ethanol): $\tau_{max}$ 236, 242, 291, 316, 357 nm.

Dipyridophenazine (DPPZ). A magnetically stirred solution of the quinone (o.10 g, 0.48 mmol) and o-phenylenediamine (0.10 g, 0.92 mmol) was heated to reflux in ethanol (ca 30 mL) for 30 min and then cooled to room temperature. The bright orange solution was concentrated in vacuo, giving an orange solid which was redissolved into $CHCl_3$ (75 mL). The $CHCl_3$ solution was washed with aqueous HCl (pH=5, 3×50 mL), water (5×50 mL), and brine (1×50 mL), and then dried over anhydrous sodium sulfate. The $CHCL_3$ solution was concentrated in vacuo to give 40.6 mg (30%) of DPPZ as an orange solid: m.p. 247–249; MS (fab): m/e 283 (MH+).

[Ru(1,10-phenanthroline)$_2$DPPZ)(Cl$_2$)]: A magnetically stirred solution of Ru(4,7-diphenyl-1,1,10-phenanthroline)$_2$Cl$_2$ (60 mg, 0.072 mmol) and DPPZ ligand (21 mg, 0.074 mmol) was warmed to 50°–65° C. in 90% ethanol/water (ca 75 mL) for about 6 h. The orange solution was cooled, filtered, and then concentrated to dryness in vacuo. The resulting red solid was redissolved into methanol (5 mL) and applied to a short-path (8–10 cm) cellulose chromatography column. The column was eluted first with ethyl acetate and then with 15% methanol/85% ethyl acetate. A red colored fraction was separated and then concentrated in vacuo to give the desired Ru(II) complex as a deep red powder: MS(fab):m/e 1048 (cluster, MH+), 766(cluster, loss of DPPZ), 716 (cluster, loss of DIP).

[Ru(DPPZ)$_3$][Cl$_2$]: To a magnetically stirred solution of Ru(Cl)$_3$3H$_2$O(0.034 g, 0.13 mmol) in water (10 mL) was added slowly a solution of the DPPZ ligand (0.122 g, 0.43 mmol) in DMF (30 mL). The reaction mixture was warmed to 85°–90° C. in the dark, giving an olive green mixture. The mixture was treated with H:PO$_2$ (ca. 2 mL, neutralized with NaOH to pH 6) and then heated to reflux for 2 h. The orange-red solution was filtered, treated with HCl, and then slowly concentrated in vacuo to give the desired complex as a deep red powder: MS(fab): m/e 948 (cluster, as cation), 665 (cluster, loss of DPPZ), 382 (cluster, loss of 2 DPPZ rings); Vis (water): $\tau_{max}$=520 nm.

[Ru(DPPZ)$_2$Cl$_2$]: To a magnetically stirred solution of DPPZ ligand (0.0309 g, 0.110 mmol) in 90% DMF, 10% ethanol and LiCl (0.078 g, 1.1 mmol) 30 mL was added slowly a solution of Ru(Cl)$_3$—3H$_2$O (0.011 g, 0.052 mmol) in ethanol (5 mL). The reaction mixture was warmed to reflux 100°–110° C. for 4 hr in the dark, giving a dark purple mixture. The solvent was then removed by reduced presure to give a dark purple powder. The yield was 75%.

As expected, preparations of Ru(bpy)2(dppz)$^{2+}$ (10 µM) in buffer R([9]) and buffer R-L([10]) (pH=7.0) produced species that were nonluminescent solutions (FIG. 21a) ($\lambda_{irr}$=482 nm). However, when Ru(bpy)$_2$(dppz)$^{2+}$ (10 µM) was mixed with 100 µM, poly d(GC) (buffer R) the solution was highly luminescent ($\lambda_{irr}$=482 nm) produced a max=628 nm (FIG. 21b) under conditions consistent with B-form DNA. From this data we postulate that the complex has fully intercalated into the helix, and as a consequence the hydrogen bonding of the phenazine nitrogens has been interrupted.

An interesting twist to the luminescent properties of Ru(bpy)$_2$(dppz)$^{2+}$ is observed when this complex is bound to the left handed helix Z-form DNA. When Ru(bpy)$_2$(dppz)$^{2+}$ (10 µM) was mixed with 100 µM, poly d(GC).d(GC) (buffer R-L) the solution was highly luminescent ($\lambda_{irr}$=482 nm) and produced a $\lambda_{max}$=640 nm(FIG. 21c) under conditions that are consistent with forming Z-DNA. Luminescent behavior such as this can be attributed to a highly intercalated species. This must be due to the complex being bound to the Z-from nand not due to lower salt conditions (or added Co(NH$_3$)$_6$$^{3+}$) as the under the same Z-form producing conditions, calf thymus DNA produces the expected B-from luminescence. Unlike other intercalating species such as ethidium-Br([11]), Ru(bpy)$_2$(dppz)$^{2+}$ does not cause the Z to B transition as solutions of the complex Ru(bpy)$_2$(dppz)$^{2+}$ with Z-form DNA are stable over hours as shown by circular dichroism.

To further test the extent of intercalation of this complex we studied the steady state luminescence polarization of the complex bound to each form of DNA. These experiments give information on how rigidly the complex is held by the DNA. FIG. 22, curve A showns at 1 µM probe (100 µM DNA) the highest luminescence polarization was observed for this solution (0.15). This reflects a situation where the complex is completely bound to the right-handed helix. As the concentration of Ru(bpy)$_2$(dppz)$^{2+}$ increases, the polarization decreases to a limiting value (0.10) at a complex: base pair rtio of 1:10. Further, addition of Ru(bpy)$_2$(dppz)$^{2+}$ produces the same polarization value, we therefore surmise that the helix becomes saturated and the unbound complex does not contribute to the polarization value.

Similarly, when 1 µM Ru(bpy)$_2$(dppz)$^{2+}$ is titrated into poly d(GC).d(GC) (100 µM) in the Z-form, luminescence polarization is also observed, but in this case the value is 0.35, over double the value found with the analogous solution with B-form. This suggests that the complex, Ru(bpy)$_2$(dppz)$^{2+}$ binds better to the Z-form and is held more rigidly to this left-handed helix. As more complex is added the observed polarization reduces to a limiting value of 0.14, still higher than the analogous sample with B-form, thus further confirming the Z-form is a more rigid structure than the B-form. Lastly, these results suggest that Ru(bpy)$_2$(dppz)$_2$ binds to Z-form with a ratio of 1 metal complex : 10 base pairs.

As described above the structure of the DNA helix is important in suquesting H$_2$O from the molecular switch, Ru(bpy)$_2$(dppz)$^{2+}$. A study of the effect of destroying the helical structure of the DNA after the complex has bound or, in other words, follow the luminescence as the DNA melts was negative. For comparison a study of the temperature dependence of the luminscence in isopropanol. At 25° C. the lifetime of the complex was 209 ns. As the temperature of the solution was increased there was an accompanying decrease in the life of 102 ns (Table 1). This decrease in lifetime was linear with a slope of 2.1 nsdeg and an intercept of 267 ns. This linear behavior is expected and is similarly observed in other systems([33]). Furthermore the apparent quantum yield for luminescence does not change appreciably over this temperature range.

While a linear relationship of the luminescence is observed for Ru(bpy)$_2$(dppz)$^{2+}$ in iso-propanol as a function of temperature this is not the behavior seen when the complex is bound to DNA. When the complex, Ru(bpy)$_2$(dppz)$^{2+}$ is bound to cal-thymus (CT) DNA (100 µM) under low salt conditions at 25 ° C. a biexponential lifetime is observed. A short component which is assigned to a surface interaction, and a long component which is assigned to an intercalated species. As is shown in Table 1, the short component remains relatively unchanged until 70 °C. when there is an abrupt decrease in the lifetime to 45 ns at 85° C. The behavior of the long component also shows this behavior although not as abruptly. Under these conditions the CT DNA melts and the observed lifetimes of the complexes are similar to those lifetimes measured with single stranded DNA. It is also noted that the quantum yield for luminescence decreases as the temperature is increased, this being due to less of the complex bound at the higher temperatures. In fact there is an abrupt decrease in the quantum yield at the melting temperature at this salt concentration. This decrease in quantum yield may be explained thus: when the complex is bound to the double stranded form the quenching ability of $H_2O$ is inhibited while at the melting temperature the single stranded form of DNA cannot protect the complex from quenching of $H_2O$ and therefore the observed luminescence is not as intense.

TABLE 1

| The Luminescent Lifetimes of $Ru(bpy)_2(dppz)^{2+}$* in Various Solvents and in the presence of DNA Solvent | | |
|---|---|---|
| Solvent | Temp in °C. | $\tau$ (ns) |
| w/o DNA | | |
| $H_2O$ | 25 | — |
| Buffer | 25 | — |
| $CH_3OH$ | 25 | 30 |
| Iso-propanol | 25 | 210 |
| Iso-propanol | 35 | 192 |
| Iso-propanol | 45 | 174 |
| Iso-propanol | 55 | 154 |
| Iso-propanol | 65 | 129 |
| Iso-propanol | 75 | 102 |
| W/CT DNA | 100 | |
| $\mu M$ (short) long** | | |
| Buffer | 25 | (75) 259 |
| Buffer | 35 | (73) 232 |
| Buffer | 45 | (73) 232 |
| Buffer | 55 | (68) 204 |
| Buffer | 65 | (68) 189 |
| Buffer | 75 | (54) 144 |
| Buffer | 85 | (45) 118 |

*10 $\mu M$ $Ru(bpy)_2(dppz)^{2-}$
**Two components of the lifetime are observed, the short component is assigned to a surface bound species, while the long component is assigned to an intercalated species.

IV. Anti-HIV Drug Testing the virus reproductive cycle. The assay basically involves the killing of T4 lympnocytes by HIV. Small amounts of HIV are added to cells, and at least two complete cycles of virus reproduction are necessary to obtain the required cell killing. Agents which interact with virions, cells, or protect cells from cytolysis. The system is automated in several ceatures to accomodate large numbers of candidate agents, and is generally designed to detect anti-HIV activity. However, compounds which degenerate, or are rapidly metabolized in the culture conditions may not show activity in this screen. Also, while every attempt has been made to reduce variability, precise values for $EC_{50}$, $IC_{50}$, and Therapeautic Index are not possible. All tests are compared with a positive (AZT-treated) control done at the same time under identical conditions.

The Procedure:
1. R4 lymphocytes (CEM cell line) are exposed to HIV at a virus to cell ratio approximately 0.05, and plated along with noninfected control cells in 96-well microtiter plates.
2. Candidate agent is dissolved in dimethyl sulfoxide (unless otherwose instructed), then diluted 1:200 in cell culture medium. Further dilutions (half-$log_{10}$) are prepared before adding to an equal volume of medium containing either infected or noninfected cells.
3. Cultures are incubated at 37° in a 5% carbon dioxide atmosphere for 6 or 7 days.
4. The tetrazolium salt, XTT, is added to all wells, and cultures are incubated to allow formazan color development by viable cells.
5. Individual wells are analyzed spectrophotometrically to quantitate formazan production, and in addition are viewed microscopically for detection of viable cells and confirmation of protective activity.
6. Drug-treated virus-infected cells are compared with drug-treated noninfected cells and with other appropirate controls (untreated infected and untreated noninfected cells, drug-containing wells without cells, etc.) on the same plate.
7. Data are reviewed in comparison with other tests done at the same time, and a determinatin about activity is made.

Several complexes were tested for use as agents active against (HIV). Results of the complex $Rh(DIP)_3$ are presented in tables 2-12 and FIGS. 23-33. The results indicate the Rh(Dip)3 complex is moderately active in inhibiting the activity of HIV.

TABLE 2

| Summary | | Infected Culture | | Uninfected Culture | |
|---|---|---|---|---|---|
| Index | Concentration | Dose ($\mu g/ml$) | Response(%) | Dose ($\mu g/ml$) | Response(%) |
| IC 50 ($\mu g/ML$) | 3.86 × 10+ | 1.25 × 10− | 2.8 | 1.25 × 10− | 110.1 |
| EC50 ($\mu g/ml$) | 7.67 × 10+ | 1.25 × 10− | 2.6 | 1.25 × 10− | 113.1 |
| T150 (IC/EC) | 5.03 × 10+ | 1.25 × 10− | −2 | 1.25 × 10− | 106.0 |
| | | 1.25 × 10− | −7 | 1.25 × 10− | 103.2 |
| | | 1.25 × 10− | −3 | 1.25 × 10− | 111.0 |
| | | 1.25 × 10+ | 1.1 | 1.25 × 10+ | 106.5 |
| | | 1.25 × 10+ | 63.2 | 1.25 × 10+ | 98.6 |
| | | 1.25 × 10+ | −3 | 1.25 × 10+ | −6 |

The procedure used For testing agents active against (HIV) is designed to detect agents acting at any stage of

TABLE 3

| Summary | | Infected Culture | | Uninfected Culture | |
|---|---|---|---|---|---|
| Index | Concentration | Dose($\mu g/ml$) | Response(%) | Dose ($\mu g/ml$) | Response(%) |
| IC 50 ($\mu g/ML$) | 4.40 × 10+ | 1.25 × 10− | 4.6 | 1.25 × 10− | 100.3 |
| EC50 ($\mu g/ml$) | | 1.25 × 10− | 1.9 | 1.25 × 10− | 98.9 |
| T150 (IC/EC) | | 1.25 × 10− | −5.0 | 1.25 × 10− | 89.3 |

TABLE 3-continued

| Summary | | Infected Culture | | Uninfected Culture | |
|---|---|---|---|---|---|
| Index | Concentration | Dose(μg/ml) | Response(%) | Dose (μg/ml) | Response(%) |
| | | 1.25 × 10− | −5.8 | 1.25 × 10− | 91.0 |
| | | 1.25 × 10− | −6.6 | 1.25 × 10− | 93.4 |
| | | 1.25 × 10+ | −.4 | 1.25 × 10+ | 99.5 |
| | | 1.25 × 10+ | 12.7 | 1.25 × 10+ | 112.3 |
| | | 1.25 × 10+ | .1 | 1.25 × 10+ | −1.6 |

TABLE 4

| Summary | | Infected Culture | | Uninfected Culture | |
|---|---|---|---|---|---|
| Index | Concentration | Dose(μg/ml) | Response(%) | Dose (μg/ml) | Response(%) |
| IC 50 (μg/ML) | 4.06 × 10+ | 1.25 × 10− | 21.7 | 1.25 × 10− | 133.6 |
| EC50 (μg/ml) | 4.36 × 10+ | 1.25 × 10− | 26.1 | 1.25 × 10− | 131.0 |
| T150 (IC/EC) | 9.33 × 10+ | 1.25 × 10− | 5.2 | 1.25 × 10− | 108.6 |
| | | 1.25 × 10− | 5.5 | 1.25 × 10− | 108.9 |
| | | 1.25 × 10− | 4.9 | 1.25 × 10− | 107.0 |
| | | 1.25 × 10+ | 15.4 | 1.25 × 10+ | 116.1 |
| | | 1.25 × 10+ | 79.2 | 1.25 × 10+ | 109.7 |
| | | 1.25 × 10+ | −5.1 | 1.25 × 10+ | −6.8 |

TABLE 5

| Summary | | Infected Culture | | Uninfected Culture | |
|---|---|---|---|---|---|
| Index | Concentration | Dose(μg/ml) | Response(%) | Dose (μg/ml) | Response(%) |
| IC 50 (μg/ML) | 2.74 × 10− | 1.25 × 10− | 11.5 | 1.25 × 10− | 105.1 |
| EC50 (μg/ml) | | 1.25 × 10− | 11.6 | 1.25 × 10− | 82.1 |
| T150 (IC/EC) | | 1.25 × 10− | .1 | 1.25 × 10− | 65.1 |
| | | 1.25 × 10− | .3 | 1.25 × 10− | 53.1 |
| | | 1.25 × 10− | 1.3 | 1.25 × 10− | 44.1 |
| | | 1.25 × 10+ | 2.4 | 1.24 × 10+ | 41.0 |
| | | 1.25 × 10+ | 27.2 | 1.25 × 10+ | 32.4 |
| | | 1.25 × 10+ | −.8 | 1.25 × 10+ | −2.1 |

TABLE 6

| Summary | | Infected Culture | | Uninfected Culture | |
|---|---|---|---|---|---|
| Index | Concentration | Dose(μg/ml) | Response(%) | Dose (μg/ml) | Response(%) |
| IC 50 (μg/ML) | 5.91 × 10+ | 1.17 × 10− | 6.5 | 1.17 × 10− | 101.9 |
| EC50 (μg/ml) | | 1.17 × 10− | 5.6 | 1.17 × 10− | 94.1 |
| T150 (IC/EC) | | 1.17 × 10− | 6.3 | 1.17 × 10− | 96.8 |
| | | 1.17 × 10− | 5.3 | 1.17 × 10− | 95.5 |
| | | 1.17 × 10− | 6.6 | 1.17 × 10− | 97.9 |
| | | 1.17 × 10+ | 9.8 | 1.17 × 10+ | 101.2 |
| | | 1.17 × 10+ | 14.7 | 1.17 × 10+ | 28.1 |
| | | 1.17 × 10+ | −.4 | 1.17 × 10+ | −.8 |

TABLE 7

| Summary | | Infected Culture | | Uninfected Culture | |
|---|---|---|---|---|---|
| Index | Concentration | Dose(μg/ml) | Response(%) | Dose(μg/ml) | Response(%) |
| IC 50 (μg/ML) | 5.41 × 10+ | 1.17 × 10− | 9.1 | 1.17 × 10− | 100.5 |
| EC50 (μg/ml) | 2.15 × 10+ | 1.17 × 10− | 9.4 | 1.17 × 10− | 96.9 |
| T150 (IC/EC) | 2.51 × 10+ | 1.17 × 10− | 9.7 | 1.17 × 10− | 102.2 |
| | | 1.17 × 10− | 9.1 | 1.17 × 10− | 100.6 |
| | | 1.17 × 10− | 7.4 | 1.17 × 10− | 104.2 |
| | | 1.17 × 10+ | 14.0 | 1.17 × 10+ | 1.5.8 |
| | | 1.17 × 10+ | 151.9 | 1.17 × 10+ | 149.3 |
| | | 1.17 × 10+ | −.6 | 1.17 × 10+ | −.7 |

TABLE 8

| Summary | | Infected Culture | | Uninfected Culture | |
|---|---|---|---|---|---|
| Index | Concentration | Dose(μg/ml) | Response(%) | Dose (μg/ml) | Response(%) |
| IC 50 (μg/ML) | 3.28 × 10+ | 1.17 × 10− | 7.5 | 1.17 × 10− | 96.6 |
| EC50 (μg/ml) | 3.01 × 10+ | 1.17 × 10− | 8.4 | 1.17 × 10− | 97.4 |
| T150 (IC/EC) | 1.09 × 10+ | 1.17 × 10− | 8.0 | 1.17 × 10− | 101.8 |
| | | 1.17 × 10− | 11.1 | 1.17 × 10− | 98.1 |
| | | 1.17 × 10− | 7.9 | 1.17 × 10− | 101.3 |
| | | 1.17 × 10+ | 13.4 | 1.17 × 10+ | 99.1 |
| | | 1.17 × 10+ | 103.3 | 1.17 × 10+ | 91.8 |

TABLE 8-continued

| Summary | | Infected Culture | | Uninfected Culture | |
|---|---|---|---|---|---|
| Index | Concentration | Dose(μg/ml) | Response(%) | Dose (μg/ml) | Response(%) |
| | | 1.17 × 10+ | −2.8 | 1.17 × 10+ | −2.1 |

TABLE 9

| Summary | | Infected Culture | | Uninfected Culture | |
|---|---|---|---|---|---|
| Index | Concentration | Dose(μg/ml) | Response(%) | Dose (μg/ml) | Response(%) |
| IC 50 (μg/ML) | 2.55 × 10+ | 1.17 × 10− | 1.5 | 1.17 × 10− | 96.5 |
| EC50 (μg/ml) | | 1.17 × 10− | 1.7 | 1.17 × 10− | 80.8 |
| T150 (IC/EC) | | 1.17 × 10− | 1.1 | 1.17 × 10− | 86.9 |
| | | 1.17 × 10− | 1.6 | 1.17 × 10− | 98.3 |
| | | 1.17 × 10− | 1.0 | 1.17 × 10− | 88.4 |
| | | 1.17 × 10+ | 1.2 | 1.17 × 10+ | 69.7 |
| | | 1.17 × 10+ | 43.8 | 1.17 × 10+ | 11.0 |
| | | 1.17 × 10+ | −1.1 | 1.17 × 10+ | .1 |

TABLE 10

| Summary | | Infected Culture | | Uninfected Culture | |
|---|---|---|---|---|---|
| Index | Concentration | Dose(μg/ml) | Response(%) | Dose(μg/ml) | Response(%) |
| IC 50 (μg/ML) | 4.21 × 10+ | 1.17 × 10− | 6.7 | 1.17 × 10− | 100.2 |
| EC50 (μg/ml) | 2.48 × 10+ | 1.17 × 10− | 9.1 | 1.17 × 10− | 102.4 |
| T150 (IC/EC) | 1.69 × 10+ | 1.17 × 10− | 8.0 | 1.17 × 10− | 115.3 |
| | | 1.17 × 10− | 8.2 | 1.17 × 10− | 121.1 |
| | | 1.17 × 10− | 11.0 | 1.17 × 10− | 113.8 |
| | | 1.17 × 10+ | 18.1 | 1.17 × 10+ | 128.4 |
| | | 1.17 × 10+ | 116.5 | 1.17 × 10+ | 113.2 |
| | | 1.17 × 10+ | −.8 | 1.17 × 10+ | −1.1 |

TABLE 11

| Summary | | Infected Culture | | Uninfected Culture | |
|---|---|---|---|---|---|
| Index | Concentration | Dose(μg/ml) | Response(%) | Dose (μg/ml) | Response(%) |
| IC 50 (μg/ML) | 2.64 × 10+ | 1.17 × 10− | .6 | 1.17 × 10− | 101.1 |
| EC50 (μg/ml) | | 1.17 × 10− | .8 | 1.17 × 10− | 95.3 |
| T150 (IC/EC) | | 1.17 × 10− | .2 | 1.17 × 10− | 110.6 |
| | | 1.17 × 10− | .1 | 1.17 × 10− | 108.9 |
| | | 1.17 × 10− | .5 | 1.17 × 10− | 93.7 |
| | | 1.17 × 10+ | 1.3 | 1.17 × 10+ | 73.3 |
| | | 1.17 × 10+ | 8.4 | 1.17 × 10+ | 7.0 |
| | | 1.17 × 10+ | −.7 | 1.17 × 10+ | −1.0 |

TABLE 12

| Summary | | Infected Culture | | Uninfected Culture | |
|---|---|---|---|---|---|
| Index | Concentration | Dose(μg/ml) | Response(%) | Dose (μg/ml) | Response(%) |
| IC 50 (μg/ml) | 7.79 × 10+ | 9.14 × 10− | 12.4 | 9.14 × 10− | 92.9 |
| EC50 (μg/ml) | 2.93 × 10+ | 1.82 × 10+ | 18.5 | 1.82 × 10+ | 91.8 |
| T150 (IC/EC) | 2.65 × 10+ | 3.65 × 10+ | 64.7 | 3.65 × 10+ | 82.4 |
| | | 7.31 × 10+ | 45.4 | 7.31 × 10+ | 55.2 |
| | | 1.46 × 10+ | −.3 | 1.46 × 10+ | −.9 |
| | | 2.92 × 10+ | −.9 | 2.92 × 10+ | −1.6 |
| | | 5.85 × 10+ | −1.8 | 5.85 × 10+ | −.7 |
| | | 1.17 × 10+ | −1.8 | 1.17 × 10+ | −1.5 |

The Graphic Results Summary Section: FIGS. 23-33 display a plot of Log 10 of the sample's concentration (as μg/mL or molar) against the measured test values expressed as a percentage of uninfected, untreated control values. The solid line connecting the diamond symbols depicts the percentage of surviving HIV-infected cells treated with your sample (at the indicated onccentration) relative to uninfected, untreated cotrols. This line expressed the in-vitro anti-HIV activity of your sample. The dashed line connecting the square symbols depicts the percentage of surviving uninfected cells treated with your sample relative to the same uninfected, untreated controls. This line expresses the in-vitro growth inhibitory properties of your sample. The viral cytophathic effect in this particular experiment is indicated by a dotted reference line. This line shows the extent of destruction of cells by the virus in the absence of treatment and is used as a quality control parameter. Values of this parameter less than 50% are considered acceptable in the current protocol. Reference lines at 0% and 50% are depicted as alternating dots and dashes.

RESULTS AND DISCUSSION

I. Synthesis and Characterization. The complex Ru(phi)$_3^{2+}$ can be synthesized from the silylated phi ligand in greater than 51% yield. Alternate synthetic schemes, involving metal reaction and concomitant oxidation of coordinated diaminophenanthrene, were less reproducible and gave poor yield. [Ru(phi)$_3$]Cl$_2$ is a stable molecule that does not decompose upon exposure to air or by continuous irradiation with visible light. The ligand is not similarly stable but instead rapodly condenses to the dimeric phenanthromimidazole. Hence spectral comparisons between coordinated ruthenium complexes and free ligand cannot be easily accomplished. The zinc complex was therefore synthesized to provide a spectroscopic analogue for the coordinated ligand. Despite reflux with high ligand concentrations, only the mono-phi zinc adduct formed.

Figure 2:
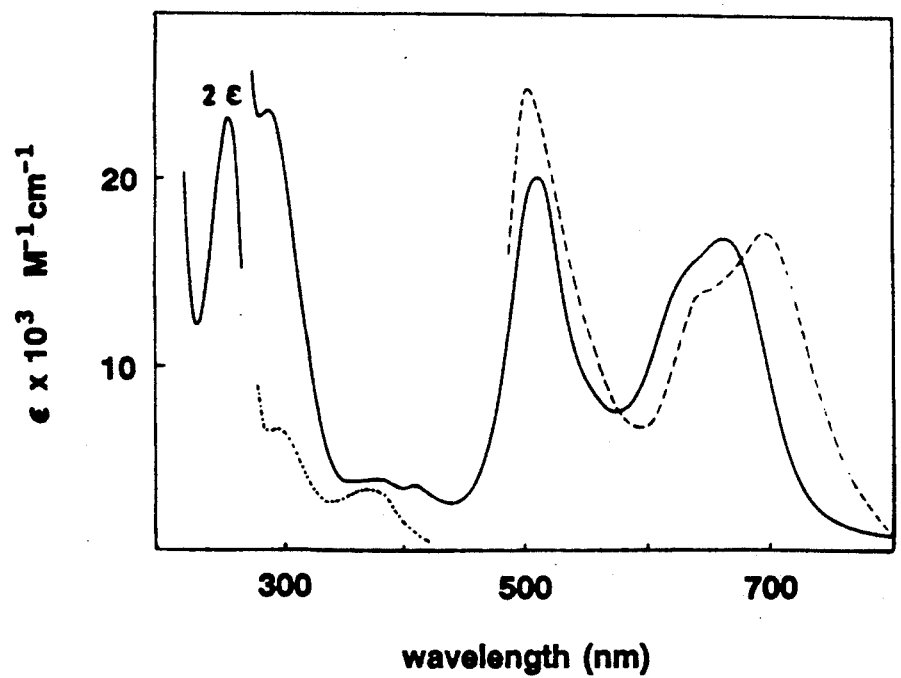
FIG. 2: Absorption spectra of Ru(phi)$3^{2+}$ in ethanol (-) and from, 500 to 800 nm in HMPA (--). Absorption spectrum of Zn(phi)Cl$_2$ in DMF from 275 to 425 nm (..) is not to scale.

Ru(phi)$_3$Cl$_2$ is a vivid purple molecule with a rich absorption spectrum. A representation of its structure is shown in FIG. 1. The electronic spectrum of Ru(phi)$_3$$^{2+}$, along with that of Zn(phi)Cl$_2$, is given in FIG. 2. The ruthenium complex shows three intense transitions in the visible region, at 510 nm ($\epsilon_{max}$=18 200M$^{-1}$ cm$^{-1}$). Assignment of the transitions is aided by comparison to the spectrum of Zn(phi)Cl$_2$, which, by virtue of its d$^{10}$ electron configuration, exhibits only $\pi$-$\pi$* transitions and should approximate the electronic behavior of the air-sensitive phenanthrenequinone diimine ligand. As can be seen in FIG. 2, the zinc complex shares with the ruthenium species transitions at 380 nm ($\epsilon_{Zn}$=2000M$^{-1}$ cm$^{-1}$, $\epsilon_{Ru}$=4000 M$^{-1}$ cm$^{-1}$, $\epsilon_{Ru}$=4000M$^{-1}$ cm$^{-1}$), 300 nm ($\epsilon_{Zn}$=4500 M$^{-1}$ cm$^{-1}$, $\epsilon_{Ru}$=32 22 500 M$^{-1}$ cm$^{-1}$), and 256 nm ($\epsilon_{Zn}$32 50000 M$^{-1}$ cm$^{-1}$, $\epsilon_{Ru}$=45000 M$^{-1}$ cm$^{-1}$). These higher energy [Ru(phi)$_3$]Cl$_2$ transitions may therefore by assigned $\pi$-$\pi$* on the basis of their similarity to those of Zn(phi)Cl$_2$. The broad intense transitions for the ruthenium complex at longer wavelengths (510, 640, and 660 nm) may be assigned in contrast as charge-transfer transitions.

Figure 3:
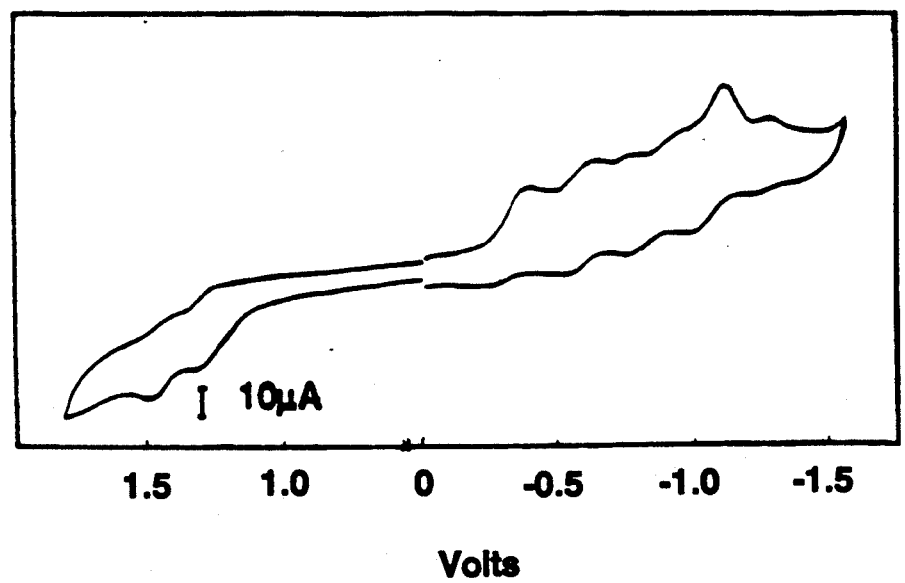
FIG. 3: Cyclic voltammogram of Ru(phi)$_3$(PF$_6$)$_2$ in acetonitrile. All measurements taken at 100 mV/s scan speed, V versus SCE. The featureless oxidative scan between 0 and 0.5V is not shown.

Cyclic voltammetry reveals multiple electrochemical reduction steps and oxidations in the ruthenium complex (FIG. 3). Electrochemical oxidation of [Ru(phi)$_3$](PF$_6$)$_2$ in acetonitrile is irreversible. Oxidation potentials of 1.23 and 1.42 eV versus SCE were observed at a scan speed of 100 mV/s. Of the six reduction potentials observed at −0.38, −0.60, −0.75, −0.95, −1.11, and −1.28 eV, only those at −0.60, −1.11 and −1.28 eV were found to be reversible, A standard of [Ru(phi)$_3$](PF$_6$)$_2$ showed first redox potentials of −1.31 and +1.30V, respectively. As may be expected, the increased $\pi$-acidity of the phi ligand compared to that of bipyridyl or phenanthroline leads to substantially decreased reduction potentials for the Ru(phi)$_3$$^{+2}$ complex.

Possible emision from [Ru(phi)$_3$]Cl$_2$ was monitored at pH 1-11, in various solvents and at 77K. No emission was observed from 350 to 800 nm. The lack of emission is understandable in view of the short lifetime of the excited state and the transient excited-state absorption spectrum ($\lambda_{max}$=440 nm), measured by flash photolysis, revealed a lifetime of $\leq$6 ns, the length of the laser pulse.

Figure 4:
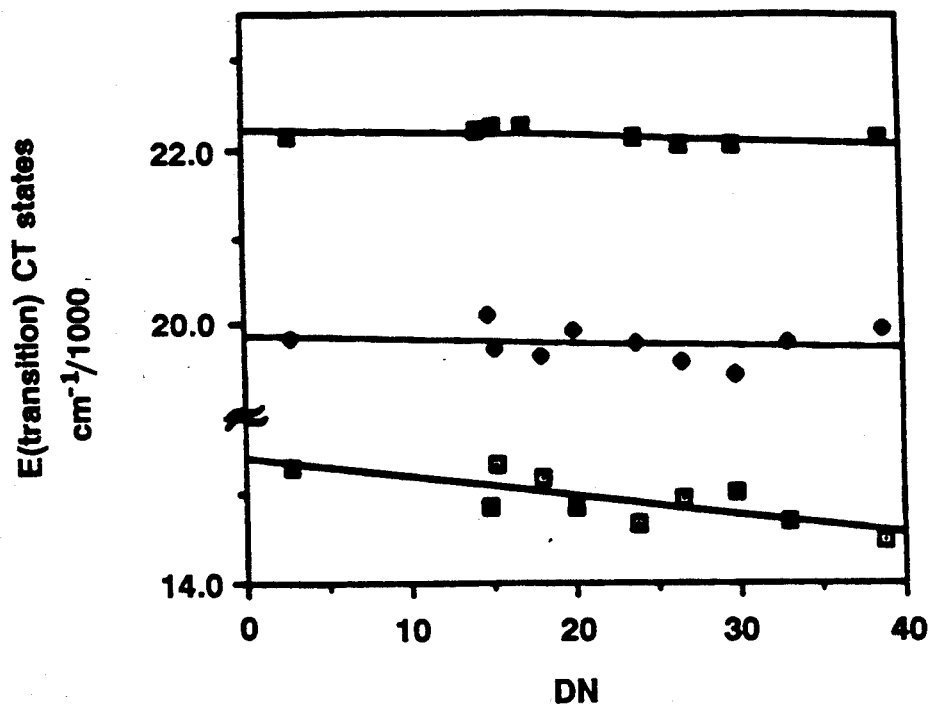
FIG. 4: Plot of hydrogen-bonding solvatochromism as measured by the shift in energy of CT bands with donor number (DN); (■) Ru(bpy)$3^{2+}$, y=22.2-0.004x; (♦) Ru(phi)$_3$Cl$_2$, CT3, y=19.8-0.004x; ( ) Run(phi)3cl2; CT1, y=15.4-0.02x. Measurements were obtained in the following solvent array (DN is parentheses); nitromethane (2.7), dioxane (14,8), propylene carbonate (15.1), water (18.0), THF (20.0), tributyl phosphate (23.7), DMF (26.6), DMSO (29.8), pyridine (33.1), HMPA (38.8).

The excited-state energy of Ru(phi)$_3$$^{+2}$ appears to be highly dependent on the molecular environment. Small changes in pH, salt concentration, or solvent lead to large variations in the $\lambda_{max}$ of the charge-transfer (CT) bands. As can be seen in FIG. 4, this solvent dependence contrasts sharply the little solvatochromism observed for Ru(bpy)$_3$$^{2+}$ (59). Most significantly, the energy of the 660-nm charge-transfer band (CT1 in ethanol) decreases lineraly as the Lewis base character, or donor number (DN), (60) of the solvent increases. CT1 commonly found amoung ruthenium diimine complexes. Curiously, it is only the CT1 absorption and not its companion band at 640 nm (CT2) that displays hydrogen-bonding solvatochromism with Lewis bases. The two seemingly fused bands at low DN seem to move apart in energy as the DN increases, and the CT1 band red shifts to as much as 700 mn in HMPA. The energy of the 510-nm band (CT3) fluctuates with solvent, but like the MLCT bands of Ru(bpy)$_3$$^{2+}$, this fluctuation is not linear with DN. Thus the CT2 and CT3 transitions of Ru(phi)$_3$$^{2+}$ are not sensitive to hydrogen bonding and must be of distinctly different character than the lowest energy CT1 band, which fluctuates between 650 and 700 nm as the stren3th of hydrogen-bonding interactions increases. Such solvatochromic behavior lends itself well to the application of the complex as a photophysical probe, because the energy of bands like CT1 becomes a sensitive indicator of the metal environment and possible hydrogen bonding interactions.

The spectral characteristics of Ru(phi)$_3$$^{2+}$ reveal several novel and unexpected features of the electronic structure of the complex. Perhaps most interesting is the lowest energy charge-transfer transition, CT1, centered at 660 nm in ethanolic solution. This transition is among the lowest energy transitions thus far observed for monomeric ruthenium (II) speices. (61) Blue ruthenium species have been reported previously, (58) but while their structures have remained elusive, all have been formulated as multinuclear species. The low-energy transitions in Ru(phi)$_3$$^{2+}$ may arise in part from the coordination of the highly delocalized phi ligand. Coordinated phenazines and dicyanomethylene-substituted phenanthrolines represent other applications of an extended $\pi$-framework, yet for those the charge-transfer transitions are centered at wavelengths more than 100 nm shorter. (62)

Most curious however is the comparison to the mixed-ligand complex (51) Ru(bpy)$_2$phi$^{2+}$. The mixed species shows charge-transfer transitions at 450 and 525 nm, which may be attributed to localized charge transfer onto the bpy and phi ligands, respectively, in the excited state. Spectra of mixed-ligand polypyridyl complexes of ruthenium (II) have in general been the simple sum of spectra for the tris-chelate complexes, since the metal to ligand charge-transfer is localized in these systems. (63) Also surprising is the short excited-state lifetime of Ru(phi)$_3$$^{2+}$ and the solvent dependence of one of the low-energy transitions.

The distinctive spectral characteristics of Ru(phi)$_3$$^{2+}$ might be understandable on the basis of a delocalized charge transfer onto the three ligands. The sequential lowering to the energy of the transition (150 nm change in wavelength) (64) with increasing substitution of phi ligands suggests such delocalization and stands in sharp contrast to spectral characteristics of the localized bipyridyl system, when the intensity rises but the energy of the charge-transfer band does not shift appreciably with increasing bpy substitution. This delocalization may also explain the intense low-energy transitions observed in other tris(-diimine) complexes. (52, 65) The delocalized framework may, finally, also account for the short excited-state lifetime of the complex, owing to large spin-orbit coupling that would be inherent in a completely delocalized system. Altenatively, the excited state is sufficiently low in energy that it may be rapidly deactivated by coupling to the ground state.

In summary, Ru(phi)$_3$$^{2+}$ displays intense, unusual transitions at low energies. On the basis of a comparison with a zinc analogue, the transitions may be described as charge transfer in character. By comparison with a mixed-ligand complexes of phi, a delocalized charge-transfer transition is suggested. Finally the dependence of the transitions on hydrogen bonding in addition to the rich intensity at long wavelengths renders the complex useful as a biophysical probe.

Figure 6A:
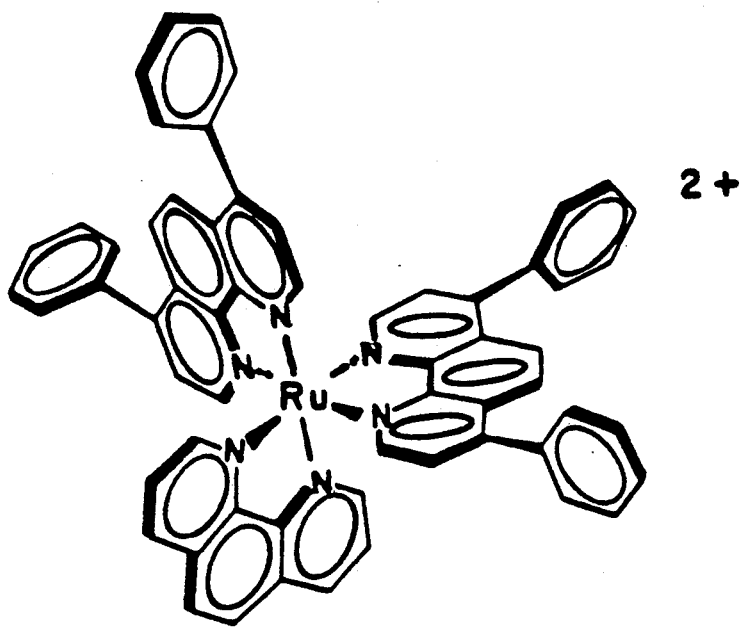
Figure 6B:
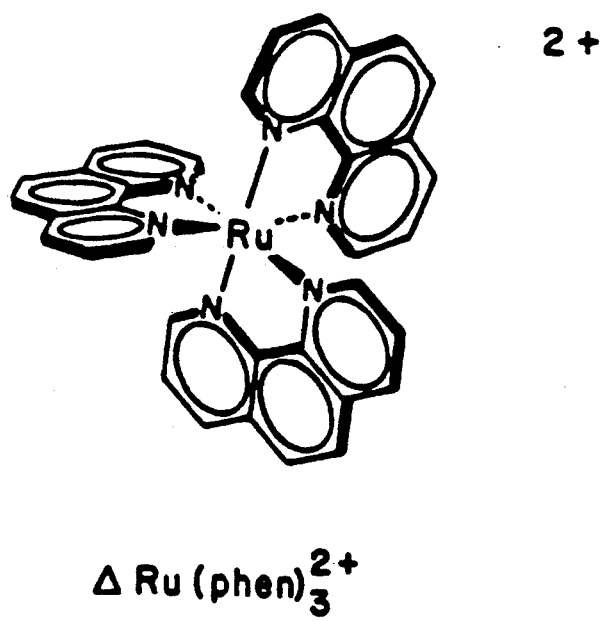
Figure 6D:
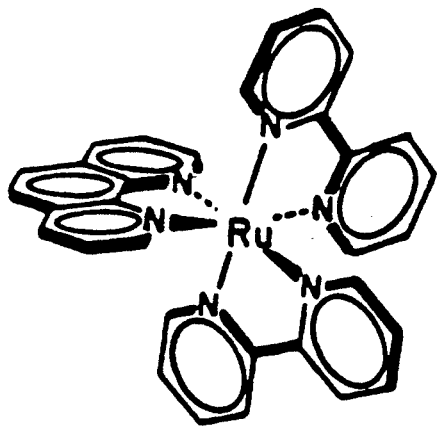
Figure 7A:
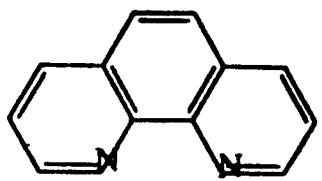
FIG. 7A to 7F: Ligands used for the synthesis of mixed-ligand ruthenium complexes.
Figure 7B:
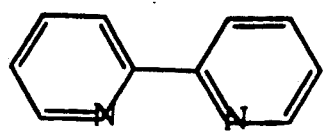
Figure 7C:
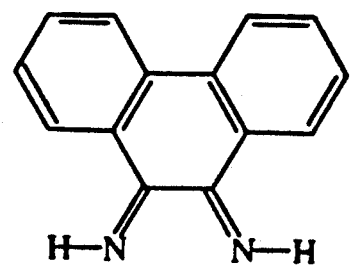
Figure 7D:
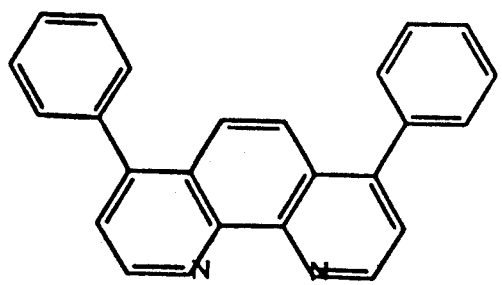
Figure 7E:
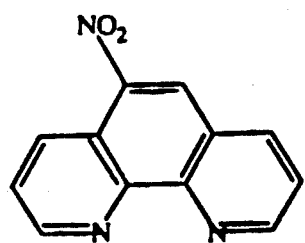
Figure 7F:
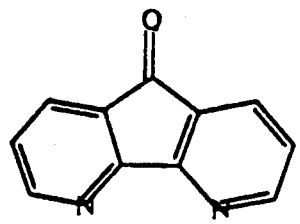

Synthesis and Characterization of Mixed Ligands Complexes:

A subset of the complexes examined is shown schematically in FIG. 6. The complexes examined are coordinatively saturated and rigid in structure. All are dications and therefore the electrostatic component of the binding is a constant across the series (to first approximation given some size variation). By varying ligands and ligand substituents in the complexes in a systematic fashion, as illustrated in series, the contributiors of the different ligand functionalities and sizes to the binding interactions with DNA can be determined. The ligands employed in this study are shown in FIG. 7. The study of the mixed ligand complexes with DNA offers the opportunity to explore systematically how such factors as molecular shape and hydrogen bonding stabilize small molecules on DNA.

Materials: $RuCl_3.3H_2O$ was purchased from Engelhard Co. Ligands (Aldrich) were checked for purity by NMR and recrystallized if necessary.

$Ru(bpy)_2(phen)]Cl_2$, $[Ru(phen)_2(bpy)]Cl_2$: These complexes were synthesized by methods as described previously. (59) $Ru((phen)_2(DIP)]CL_2$: $Ru(phen)_2Cl_2$(1 mmole) was added to 1 equivalent of 4, 7-diphenyl-1, 10-phenanthroline (DIP) and fluxed in 14 ml 75% ethanol/water for 30 minutes. The product was isolated as the $ClO_4$- salt for chromatography on cellulose (10% $CHCl_3$/hexane) and converted to the chloride salt by ion exchange. NMR(DMSO): 8.79 (4dd), 8.4 (4s), 8.24 (2d), 8.22 (2s), 8.16(2d), 8.08 (2d), 7.83 (2dd), 7.78 (2dd), 7.75(2d), 7.63(10m); FABMS ion mass: 794 $[Ru(phen)_2(DIP)]^{2+}$, 614$[Ru(pen)(DIP)]^{2+}$. $[Ru(bpy)_2(DIP)]Cl_2$: Synthesized as described above, using $Ru(bpy);Cl_2$ rather than $Ru(phen)_2Cl_2$ as starting material.

$[Ru(DIP)_2(phen)][Cl]_2$: $Ru(DIP)_2Cl_2$ was refluxed in ethanol with one equivalent of phenanthroline. The product was purified by cellulose chromatography. The $Ru(DIP)_2Cl_2$ starting material, like the other bis(-polypyridyl) complexes, was readily prepared by dissolving 3 mmoles $RuCl_3.3H_2O$, 30 mmoles LiCl and 6 mmoles DIP ligand in 100 ml DMF and refluxing for four hours. The reaction mixture was stripped of solvent and the product precipitated from ethanol/water. Futher purification was as for $[Ru(phen)_2(DIP)]Cl_2$:NMR(DMSO): 8.82(2d) 8.42(2s), 8.34(2d), 8.25(4s), 8.23(2d), 8.18(2d), 7.87(2dd), 7.80(2d), 7,74(2d), 7.69 (20m); FABMS ion mass: 946 $[Ru(DIP)_2(phen)]^{2+}$,766 $[Ru(DIP)_2]^{2+}$, 614 $[Ru(DIP)(phen)]^{2+}$.

$[Ru(5-nitrophenanthroline)_3)]Cl_2$: Synthesized as described by Lin et al. (81)

$[Ru(phen)_2(4,5-diazafuorene-9-one)]Cl_2$: One equivalent of 4,5-diazafluorene-9-one and a suspension of one mmole $Ru(phen)_2Cl_2$ in 30 ml were refluxed in wet ethanol for four hours and recystallized from aceton/heptane. The 4.5-dizafluorene-9-one ligand was synthesized as described by henderson et al. (30) NMR ($CD\mu CN$): 8.71 ppm (2 dd), 8.61 (2.dd), 7.88 (2m), 7.59(4m), 7.39(2m); FABMS ion mass: 644 $[Ru(phen)2(-flone)]^{2+}$.

$[Ru(bpy)_2(phi)]Cl_2$: This complex was prepared as previously reported by Belser et al. (78). NMR (DMSO): 13.67 ppm (2,s N—H), 8.68 (4d), 8.60 (2d), 8.35(2d), 8.05(2t), 8.0 (2t), 7.75 )2d), 7,57(2t), 7,43(8m); FABMS ion mass: 620 $[Ru(bpy)_2(phi)]^{2+}$, 465 [Ru(bpy)(phi)]$^{2+}$, 414 $[Ru(bpy)_2]^{2+}$. Anal. Calcd for $[Ru(bpy)_2(phi)](PF_6)_2$: C:44,90;H: 2.90; N: 9.20; found C: 44.62;H: 3.02;H: 8.9. A crystal structure (data not shwn), determined by x-ray diffraction analysis, confirms the coordination geometry of this species.

$[Ru(phen)_2(phi)]Cl_2$: As with the synthesis of $Ru(bpy)_2(phi)Cl_2$, this compound was prepared by refluxing 0.19 mmoles $Ru(phen)_2Cl_2$, 1.2ml 0.1M NaOh and 0.7 mmoles diaminophenanthrene in 5 ml H2) containing a catalytic amount of zinc dust. After one hour, 3 ml EtOH was added and the resultant purple solution was air oxidized for 16 hours in the prsence of 0.5 ml $NH_4OH$. The final red solution was extracted with diethyl ether to remove organic impurities and precipitated with KCl. NMR (DMSO): 13.81 ppm (2,sN-H), 8.86(2d), 8.75(2d), 8.63 (2d), 8.55(4m), 8.37 (4s), 8.05(1d), 7.95(1d), 7.85 (1d), 7.80 (2d), 7.78(1d), 7.73(2t), 7.57(2t); FABMS ion mass: 667 $[Ru(phen)_2(phi)]^{2+}$, 460 $[Ru\{phen)_2]^{2+}$, 282 $[Ru(phen)]^{2+}$; Anal. Calcd for Ru(phen)_2(phi)Cl_2.KCl. 5H_2O: C:50.50; H:4.02; N:9:30; Found: C:50.11; H:4.04; N:9.84.

$[Ru(phi)_2(bpy)]Cl_2$: obtained by a snythesis identical to that for $[Ru(benzoquinonediimine)_2(bpy)]Cl_2$. (78) 9,10-diaminophenanthrene was used as the lignd substrante instead of diaminobenzene. In addition, solvent for the final air oxidation step of this compound was 50% ethanol/water rather than pure water. Like the other phi-containing compounds, thuis complex was first isolated as the PF6-slat and converted to chkoride by precipitation with KCl or ion exchange on AG MP-1 resin from Bio-Rad. NMR (DMSO): 14, 16 ppm (2s N—H), 12.87 (2s N—H), 8.78 (4t), 8.6(2d), 8.52(4d), 8.20(4m), 7.75(4t), 7.65(6m); FABMS ion mass: 669 $[Ru(phi)_2(bpy)]^{2+}$, 514$[Ru(phi)_2]^{2+}$, 464 $[Ru(phi)(bpy)]^{2+}$, 307 $[Ru(phi)]^{2+}$. Anal. Calcd. for $Ru(phi)_2(bpy)Cl_2.6HO_2)$: C:53.78; H: 4.76; N:9.90. Found: C:53.84; H: 496; N:9.02.

METHODS

Instrumentation: NMR spectra were recorded on a Varian VXR-300MH$_z$ spectormeter. FABS were performed using a VG Analytical 7070EQ Mas Spectrometer (78), and elemental analyses were done by Galbraith Laboratories in Nashville, Tenn. UV-Visible absorbance spectal were recorded on a Varian CARY-219 absorbance spectorphotometer. Extinction coefficients for the compounds were determined versus ruthenium concentrations obtained by atomic absorption spectroscopy with known ruthenium standards. $[Ru(bpy)_3]Cl_2$ solutions were also employed for these determinations as an internal standard. A varian AA-875 atomic absorption spectrophotometer was used for these determinations.

Emission spectra were measured on a Perkin-Elmer LS-5 fluorescence spectrometer. The samples were excited at their corresponding isosbestic points. All the measurements were made at 20° C. in a thermostatted cuvette holder with 3 nm entrance slit and 10 nm exit slit. Ruthenium solutions employed were 7 $\mu M$ in concentration and claf thymus DNA was added to a ration of 40:1 nucleotide/metal; ruthenuim-DNA soltuions were allowed to incubate for 15 minutes before enhanced spectra were recorded. The emission enhancement factors were measured by comparing the intensitites at the emission spectral mixima in the absence ad presence of DNA, under similar conditions.

The limunescence lifetime measurements were done on a PRA SPC (single photon countining) spectrometer with some minor modifications. The samples were excited with a nitrogen filled tnynratron gated flash lamp and the data were collected using a Tracor Northern 1710 multichannel analyser. The data were then transferred to a PDP-11/03 computer and deconvoluted with PRA software. The validity of the convergent biexponential concentrated solution of DNA (5mM DNA-phosphate) in buffer was added to a solution of the metal complex (4 $\mu$M) in buffer and allowed to equilibrate. Lifetimes of the samples were measured 0.5 hr after the metal complexes were mixed with DNA. All measurements were made at 20° C. and under air saturated conditions.

Excited state resonance Raman spectra were run on a home-built Raman spectrometer witn an intensified multichannel detector. (84) The samples were excited by a QuantaRay, Q-switched, Nd-YAG laser (DCR-2, FWHM +6ns, 5mj per pulse at 355 nm). The laser power was high enough to saturate the ecited state population and also to scatter off from the excited state formed during the laser pulse-width. The sample solution was pumped through a nozzle to form a smooth thin jet which was intercepted by the laser. The back scattered light was collected at a small angle to the pump beam and focused onto the entrance slit of the Spex triple-mate spectrograph. The third stage of the spectrograph contaiend at 2400 grooves/mm grating to provide 2 cm$^{-1}$ resolution for the Raman experiments. The entire experiment was run by a home made menu-driven program with customized graphics written in Heminway Basic. The spectra were calibrated using the known spectrum of Ru(bpy)$_3^{2+*}$. (85) To a solution of calf thymus DNA (1 mM) was added Ru(bpy)$_2$-DIP$^{2+}$(40 $\mu$M) and the solution was felt to equilibrate for 0.5 hour. The solution was then circulated as a thin, smooth and slow stream. No degradation in the sample, as determined by optical absorption, was observed after recording of the Raman spectrum under these conditions.

Measurement of Solubilities: Solubilities of the compounds wre measured by preparing saturated solutions of metal complex in buffer (50mM NaCl, 5 mM Tris, pH 7.5) and allowng the suspensions to equilibrate for 24 hours at 25 C. After that time, the solutions were spun down in an Eppendorff microcentrifuge at 15,000 rev/-min for 2 minutes and the supernatant was carefully removed by pipette. After dilution, the ruthenuim concentrattions were measured by UV-visible absorbance.

Equilibrium Dialysis: Equlibrium dialysis of the reacemic metal complexes was perforemd against calf-thymus DNA using procedures described previously. (74) The buffer used was 5 mM Tris, 50 mM NaCl at pH 7.5. Samples were agitated on a shaker bath during equilibration which occurred after three to five days, as determined by control samples containing no DNA. After equilibration, volumes of liquid inside and outside the dialysis bags were determined (approximately 1 and 3 mls, respectively) and circular dichroism of the dialysate was meaxured on a Jasco J-40 spectropolarimeter. Final ruthenium concentration inside and outside the bags were measured by visible absorbance. Data anaylsis was performed on a VAX-780 using non-linear least squares analysis.

Topoisomerase Assay: In a typical experiment, pBR322 DNA dinner (0.47 $\mu$g, BRL) was incubated at 37° C. for 1 h with 2 to 4 units of Topoisomerase I (from calf thymus, BRL) in reaction mixtures containing 5 mM Tris-HCI, pH 7.2, 50 mM NaCl, 1 mM MgCl 2, and from 1 to 100 $\mu$M ruthenium complex (50 ml total volume). Following incubation, the mixtures wre ethanol precipitated (200 ml ethanol at −20° C., centrifuged, and resuspended in 20 ml buffer (no mg$^{2+}$). The samples were then electrophoresed in 1% agarose for 4 to 6 h. Photographic negatives of the agarose gels were scanned on an LKB model 2202 ultroscan laser densitometer. The unwiding angles were determined graphically from plots of −$\tau$, where $\tau$ equals the number of superhelical turns, versus the concentration of bound ruthemium complex, as described by Keller, (86) using the following equation: (87)

$$\tau = 20 r_c(\phi/360) = r_c\phi/18$$

where $\sigma$ is the superhilical density of the plasmid, $r_c$ is the amount of metal complex ions bound per nucleotide when all of the superhelices are removed, and $\phi$ is the unwinding angle. Bond concentrations were determined by interpolation from the Scatchard plots of equilibrium dialysis data.

I. RESULTS

Figure 8B:
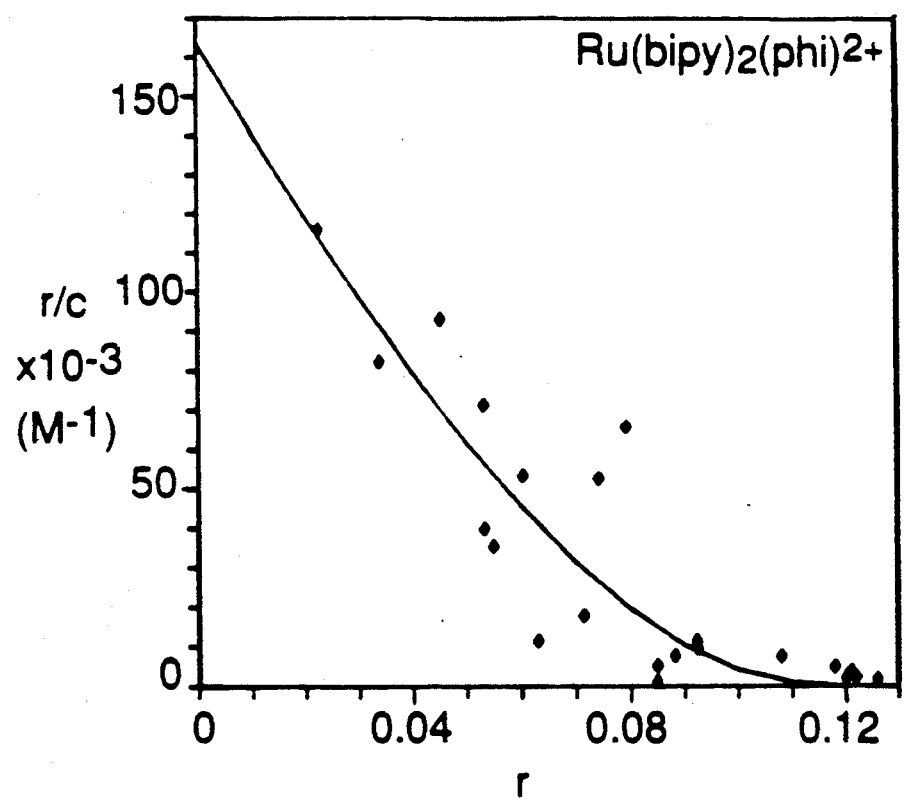
FIG. 8A$_1$ to 8A$_7$, 8B: Representative Scatchard plots of binding isotherms for mixed-ligand complexes of ruthenium (II) with calf thymus DNA in buffer at 22° C., where r is the ration of bound ruthenium to nucleotide concentrations and C is the concentration of free ruthenium. The solid lines are the best fits to the McGhee and von Hippel equation (45) governing noncooperative binding to the helix.

Equilibrium Dialysis: Equilibrium binding constants for the metal complexes with DNA may be determined classically by equilibrium dialysis. Calf thymus DNA was dialyzed against the series of mixed ligand complexes using a broad range of ruthenium concentrations. Data are shown in FIG. 8 for the eight complexes which showed noncooperative binding to the polynucleotide. The results have been plotted according to Scatchard (88), where r is the ratio of bound metal to DNA-phosphate concentration, and $c_f$ is the concentration of free metal complex. The data were fit by non-linear least squares analysis to the McGhee and von Hippel equation (8945) governing random non-cooperative binding to a lattice, $$2r/c_f + k_b(1-2/r)[(1-2/r)/[1-2(/-1)r]]/^{-1}$$

where r is the ratio of bound concentration of ruthenium to the concentration of DNA-phosphate, $c_f$ is the concentration of ruthenium free in soltuion, $K_b$ the intrinsic binding constant, and the integer /, which measures the degree of anti-cooperativeity, is the size of a binding site in base pairs. The curves shown reflect the best fit after variation of two parameters: the intrinsic binding constant, $K_b$, and binding stie size, /. For those complexes were cooperatively was observed, the equation (89) incorporating a cooperativity parameter was used. The values obtained are summarized in Table 13.

TABLE 13

DMA Binding Permeates for mixed ligand complexes of ruthenium(II)

| Complexes | Km × 10) equilibrium dialysis | K(M × 10) by absorption titration | Site size (base pairs) | Unwinding concentration ($\mu$M) | Unwinding Angle (degrees) | Enantio-selectivity |
|---|---|---|---|---|---|---|
| Ru(bpy) Cl | 0.7(.13) | h | 6-12 | 650 | | none |
| Ru(bpy) (phen)Cl | 0.7(.07) | h | 10-14 | 69 | | |
| Ru(phen) (bpy)Cl | 2.4.(.4) | 4.6(1.0) | 5-7 | 11 | 18 | |
| Ru(phen)3Cl2 | 3.1(.1) | 5.5(.99) | 4 | 9 | 19 | |
| Ru(5-No phen) Cl | 1.0(.1) | h | 8-12 | i | | |
| Ru(phen) (flone)Cl | 2.1(.2) | h | 9-12 | i | | none |
| Ru(bpy) (DIP)Cl | 1.7(.3) | h | 12-18 | 170 | | |
| Ru(phen) (DIP)Cl | 2.5(1.0) | 11.2(.99) | cooperative | 9 | | |
| Ru(DIP) (phen)Cl | 10.1(3) | 11.1(.99) | cooperative | j | j | |
| Ru(phi) (bpy)Cl | 17.6(—) | 24.4(.98) | cooperative | 0.6 | j | k |
| Ru(phen) (phi)Cl | 46.(6) 100.(37) | 46.8(.99) | 2-3 | 1.2 | 26 | l |
| Ru(bpy) (phi)Cl | 160.(17) | 48.0(.99) | 4 | 1.1 | 17 | l | a. Standard deviations are given in parentheses.
b. Correlation coefficients between observed and calculated values are given in parentheses. Values for $K_b$ have been calculated as described in the text.
c. For this range of site sizes, less than 1% variation in correlation coefficient and standard deviation in $K_b$ is found. For the lowest site size given, best correlation and the lowest standard in $K_b$ are obtained.
d. Concentration of ruthenium complex needed to unwind 11 of 22 superoids. [DNA] = 47 $\mu$M for assays of phi-containing complexes and 31.5 $\mu$M for all others.
e. Unwinding angles represent the number of degrees by which one molecule of bound complex unwinds the DNA helical duplex. Values are calculated with some certainty only for those complexes where the binding is otherwise well-behaved.
f. Deltas represent an enantiomeric preference for the $\Delta$ isomer in binding to DNA.
g. The lower binding constant and size given result from fitting only those points where r > 0.08. The higher binding constant given results from inclusion of all points. Although the fit with all points included is poorer, it is probably a better overall estimate of binding affinity.
h. At the extremely low levels of binding obtained with these complexes, changes in the absorption spectrum were too small to allow for significant determinations.
i. Measurements were not conducted on this complex.
j. Measurement could not be performed due to the poor solubility of the complex.
k. A small circular dichroism was occasionally observed in the dialysate.
l. Although the dialysate showed a strong circular dichroism, and thus a clear enantiomeric selectivity in binding to DNA exists, the absolute configurations for the phi complexes cannot be inferred from simple comparison to phenanthroline complexes.

For the complexes shown, the intrinsic binding constant is seen to vary over more than two orders of magnitude. The highest binding affinity is seen for complexes which contain the phi ligand. Other variations, though of a smaller magnitude, are apparent as a function of increasing size and hydrophobicity. For example, for the series Ru(bpy)$_3$2+, Ru(bpy)$_2$(phen)$^{2+}$, Ru(bpy)$_2$(DIP)$^{2+}$, and Ru(bpy)$_2$(phi)$^{2+}$, we find $K_b$ values of $0.7 \times 10^3$, $0.7 \times 10^3$, $1.7 \times 10^3$, and $1.6 \times 10^5$ M$^{-1}$, respectively. The data for the all the complexes fit reasonably well to a random non-cooperative model. Site sizes are found to vary between 2 and 12 base pairs, but values obtained fro complexes with low binding affinity ($K < 2 \times 10^3 M^{-1}$) have a high associated uncertainty.

The bulkier and more hydrophobic complexes Ru(phen)$_2$(DIP)$^{2+}$, Ru(DIP)$_2$(phen)$^{2+}$ and Ru(phi)$_2$(bpy)$^{2+}$ all showed curves indicative of cooperative binding. This observation is understandable, since these complexes tend to agfregate in solution. Thus the equlibrium involves not only bound and free monomer complexes but those involving self-stacked dinners (or even larger aggregates). Furthermore, a similar aggregation of the complexes along the DNA strands is likely. Some samples actually showed precipitation, and these were not included. The extensive aggregation of Rr(DIP)$_3$2+ and Ru(phi)$_3$2+ completely precluded their incorporation in these studies.

Equilibrium dialysis experiments additionally offer the opportunity to examine any enantiomeric selectivities associated with binding. After dialysis of the DNA against the racemic mixture, optical activity observed in the dialysate refelects an enrichment in the dialysate in the less favored enantiomer. For most of the complexes, optical activity was found in the dialysate. Values for the extent of enantiomeric selectivity could not be quanitated in the absence of determinations of DE and assignments of absolute configuration. Assuming that the signs of the circular chroism in the ultraviolet ligand bands are the same for the these ligands as that for the parent phenanthroline complex, (90) we have assigned the absolute configuration of these complexes by comparison to spectra for enantiomers of Ru(phen)$_3$2+ and have compared levels of enantioselectivity qualitatively through measurements of circular dichroic intensity per rutheium bound. Based upon these assumptions, we find enantionmeric selectivities for the polyridyl complexes to reflect an enrichment in the isomer in the dialysate and the preferential binding of the isomer to the right-handed DNA. This observation is consistent with the preferential intercalation of isomers found earlier for Ru(phen)$_3$2+ in right-handed B-DNA. (63) We may also compare relative enantioselectivities for different ancillary ligands. For the pairs, Ru(phen)$_2$phi$^{2+}$ versus Ru(bpy)$_2$phi$^{2+}$, for example, the intensity in circular dichroism per ruthenium bound is more than three times greater with phen as the ancilary ligand than with bpy. The same comparison may be seen qualitatively between Ru(phen)$_2$DIP$^{2+}$ and Ru(bpy)$_2$DIP$^{2+}$. The exceptions, where no enantiomeric discrimination is apparent, are Ru(phi)$_2$bpy$^{2+}$, Ru(bpy)$_3$2+, and Ru(phen)$_2$(flone)$^{2+}$. For Ru(phi)$_2$bpy$^{2+}$, aggregation of the complex and its poor solubility made the determinations problematic. In the cases of Ru(bpy)$_3$2+ and Ru(phen)$_2$(flone)$^{2+}$, the low levels of binding and small size of the complex may preclude observation of any selectivity.

Spectroscopic Changes on Binding to DNA: The complexes all possess intense optical absorption owing to their well-characterizedmetal to ligand charge transfer band. Furthermore, for all the complexes, this electronic transition is perturbed on binding to DNA. Table 14 summarizes the spectroscopic properties fo the complexes and some of the changes observed.

TABLE 14

SPECTROSCOPIC PROPERTIES ON BINDING TO DNA

| COMPLEX | Absorption $\lambda_{max}$ (nm) | | | Emission $\lambda_{max}$ (nm) | | | $\epsilon_{free}$ (M-1 cm-1) | Emission Enchantment ($I/I_o$) | Emission Lifetime (nanoseconds) | |
|---|---|---|---|---|---|---|---|---|---|---|
| | free | bound | Δλ | free | bound | Δλ | | | free | bound |
| Ru(bpy)$_3$$^{2+}$ | 450 | 450 | 0 | 615 | 618 | 3 | 14,600 | 1.06 | 420 | |
| Ru(bpy)$_2$(phen)$^{2+}$ | 452 | 452 | 0 | 611 | 602 | −9 | 16,000 | 1.12 | 450 | 430 ± 30(1) |
| | | | | | | | | | | 2100 ± 300(2) |
| Ru(phen)$_2$(bpy)$^{2+}$ | 446 | 448 | 2 | 608 | 604 | −4 | 19,200 | 1.43 | 555 | 530 ± 30(1) |
| | | | | | | | | | | 2100 ± 260(2) |
| Ru(phen)$_3$$^{2+}$ | 443 | 445 | 2 | 591 | 593 | 2 | 20,000 | 1.87 | 530 | 630 ± 70(1) |
| | | | | | | | | | | 2300 ± 620(2) |
| Ru(5-NO2phen)$_3$$^{2+}$ | 450 | 454 | 4 | b | — | | 20,000$^c$ | — | | — |
| Ru(phen)$_2$(flone)$^{2+}$ | 436 | 436 | 0 | b | — | | 18,800 | — | | — |
| Ru(bpy)$_2$(DIP)$^{2+}$ | 454 | 454 | 0 | 615 | 621 | 6 | 18,600 | 1.13 | 700 | 640 ± 40(1) |
| | | | | | | | | | | 4700 ± 600(2) |
| Ru(phen)$_2$(DIP)$^{2+}$ | 427$^a$ | 432 | 5 | 614 | 606 | −8 | 20,550 | 2.06 | 970 | 1160 ± 30(1) |
| | | | | | | | | | | 5290 ± 80(2) |
| Ru(DIP)$_2$(phen)$^{2+}$ | 433 | 439 | 6 | 616 | 621 | +5 | 29,400 | 2.14 | 990 | 116 ± 40(1) |
| | | | | | | | | | | 5100 ± 430(2) |
| Ru(phi)$_2$(bpy)$^{2+}$ | 572 | 582 | 10 | b | | | 75,300 | — | | — |
| Ru(phen)$_2$(phi)$^{2+}$ | 535 | 544 | 9 | b | | | 51,900 | — | | — |
| Ru(bpy)$_2$(phi)$^{2+}$ | 535 | 548 | 13 | b | | | 48,000 | — | | — | a. The double-humped charge transfer bands characteristic of ruthenium polypyridyl complexes are such that the higher energy band of Ru(phen)$_2$(DIP)$^{2+}$ and Ru(DIP)$_2$(phen)$^{2+}$ is the more intense and is therefore defined as the $\lambda_{max}$ of the complex.
b. Nonemissive complexes. Ru(bpy)$_2$(phi)$^{2+}$ was previously reported[13] to luminesce at 620 nm, but in our hands this was found to be due to Ru(bpy)$_3$$^{2+}$ contamination.
c. Extinction coefficient for Ru(5-NO$_2$-phen)$_3$$^{2+}$ was taken from reference 15.
d. (1) and (2) denote first and second components of emission lifetime decay.

For those complexes which luminesce, changes in luminescence on DNA binding are found. Increases in emission are apparent with DNA binding, and depending upon the mixed ligand complex examined, red shifts or blue shifts in the emission spectra are observed (vide infra). As was seen earlier for Ru(phen)$_3$$^{2+}$ and Ru(DIP)$_3$$^{2+}$, (29,30) the decay in emission from the excited ruthenium complex in the presence of DNA is best characterized by a biexponential, with one component having an emmision lifetime characteristic of the free ruthenium species, and one longer lived component. For Ru(phen)$_3$$^{2+}$ and Ru(DIP)$^{2+}$, this long lived component was characterized extensively and found to correspond to emission from the intercalatively bound species, the emission lifetime for the surface bound species was found to be indistinguishable from the free form. We suggest that the two components may be assinged similarly for these mixed ligand complexes. Moreover the similarity in spectroscopic perturbations seen with the mixed ligand compexes on binding to DNA supports the notion that these complexes also bind to DNA in a similar fashion.

The emission spectra and decay traces therefore suggest that the mixed ligand complexes all bind to DNA throught the mixture of two binding modes: intercalation and surface bnding. The emission enhancements provide some gauge of the extent of intercalation as well as binding affinity. After corrections for the differing affinities of phen and DIP mixed ligand complexes, from these data it appears that the intercalative component is actually quite comparable among the series. Quantitation of the surface versus intercalative components could not be made, however.

The binding of intercalative drugs to DNA has also been characterized classically through absorption titrations, following the hypochromism and red shift associated with biding of the colored complex to the helix. (91) FIG. 9 displays a well-behaved titration of Ru(phen)$_2$(phi)$^{2+}$ with calf thymus DNA. Isosbestic points are observed at 558 nm and 598 nm. The spectra show clearly that addition of DNA yields hypochromism and a large red shift in the charge-transfer band of the complex. These spectral characteristics are attributable to a mode of binding which involves a strong stacking interaction between an aromatic chromophore and the base pairs of DNA.

The magnitudes of the red shift and hypochromism are furthermore commonly found to correlate with the strength of the interaction. (91) A comparison of red shifts found with DNA bindng can be seen in Table 14. Complexes containing phi have the longest red shifts (≦13 nm), followed by DIP complexes (≦6nm), phen complexes (2≦nm), and bpy complexes (no red shift). Thus, if red shifts upon binding are taken as a measure of stacking interaction, a trend can be observed in which the optimal shape for intercalation is phi>-DIP>phen>bpy.

Figure 10:
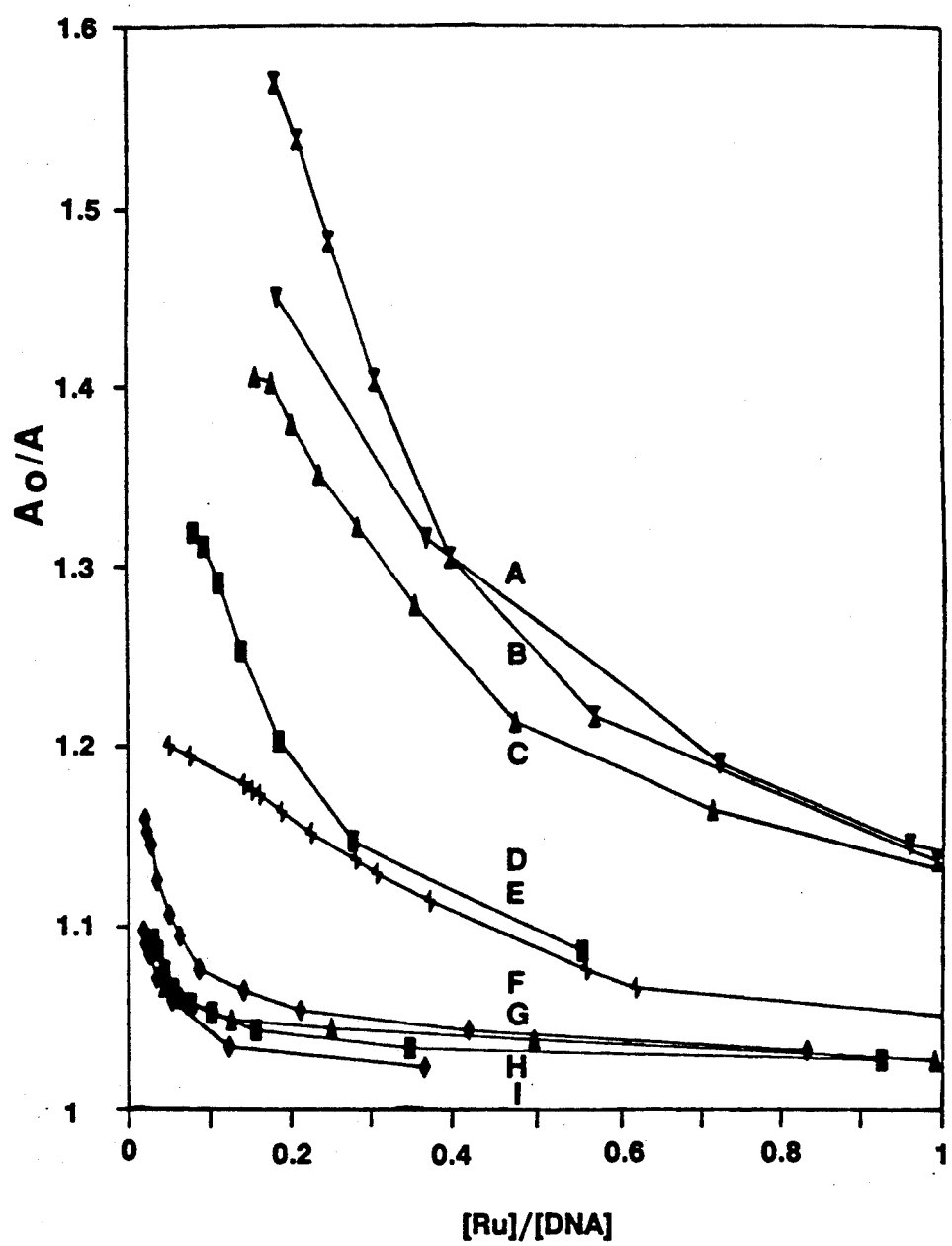
FIG. 10: Hypochromism in the visible charge transfer band as a function of [Ru]/[DNA]. Ao/A represents the ratio of absorbance of free ruthenium (in the absence of DNA) to the absorbance as a function of increasing concentrations of added DNA. A+(Ru(DIP)$_2$(phen)$^{2+}$, B=Ru(phi)$_2$(bpy)$^{2+}$, C=Ru(phen)$_2$(phi)$^{2+}$, D=Ru(bpy)$_2$(phi)$^{2+}$, E=Ru(phen)$_2$((DIP)$^{2+}$, $F=Ru(phen)_3^{2+}$, $G=Ru(5NO_2-phen)_3^{2+}$, $H=Ru(phen)_2(flone)^{2+}$, $I=Ru(phen)_2(bpy)^{2+}$.

The degree of hypochromism generally correlates well also with overall binding strength FIG. 10 shows absorption titration data for the series of complexes as a function of DNA addition. The extent of hypochromicity in the charge transfer band as a function of DNA binding, plotted reciprocally as $A_0/A$ versus [Ru]/[DNA], is found to provide a good measure of relative binding affinity, since the hypochromicity found for the series of complexes per DNA added parallels nicely the binding results by equilibrium dialysis. Ru(bpy)$_2$(phi)$^{2+}$, a soluble complex of high binding strength to DNA, and the more hydrophobic complexes Ru(phen)$_2$(DIP)$^{2+}$, Ru(DIP)$_2$(phen)$_2$ and Ru(phi)$_2$(bpy)$^{2+}$ show the greatest change in absorption with DNA addition. The latter three complexes, however, are only sparingly soluble in the buffer solution and may show increased hypochromism owing to agregation, both in solution and bound to the helix. complexes which bind only weakky to DNA, such as Ru(bpy)$_3$$^{2+}$ and Ru(bpy)$_2$(phen)$^{2+}$, are seen to show litle hypochromic effect.

Determinations of intrinsic binding constant, $K_b$, based upon these absorption (92)

$$[DNA]/(\epsilon_A-\epsilon_F)=[DNA]/(\epsilon_B-\epsilon_F)+1/K_b(\epsilon_B-\epsilon_F)$$

where $\epsilon_A$, $\epsilon_F$ and $\epsilon_B$ correspond to $A_{obs}/[Ru]$, the extinctio coefficient for the free ruthenium complex, and the extinction coefficient for the ruthenium complex in the fully bound form, respectively. In plots of $[DNA]/(\epsilon_A-\epsilon_F)$ versus [DNA], $K_b$ is given by the ratio of the slope to intercept. This half-reciprocal absorption titration method, which has been used successfully to determine the intrinsic $K_b$ of molecules as hydrophobic as benzo[a]pyrene derivatives, (48) was found to provide a useful route to obtain intrinsic binding constants for the broad range of ruthenium complex of differing solubilities. Values for $K_b$, given in Table 13, we obtained for all but those complexes which bound very weakly, the compounds $Ru(bpy)_3^{2+}$, $Ru(bpy)_2(phen)^{2+}$, $Ru(bpy)_2(DIP)^{2+}$, $Ru(5NO_2\text{-phen})_3$, and $Ru(phen)_2(flone)^{2+}$ showed such small changes in their absorption specta upon DNA addition, that the resultant error in $\epsilon_A-\epsilon_F$ was large. For the remainder, as shown in Table 13, good correlation with those values obtained by dialysis was found.

Figure 11:
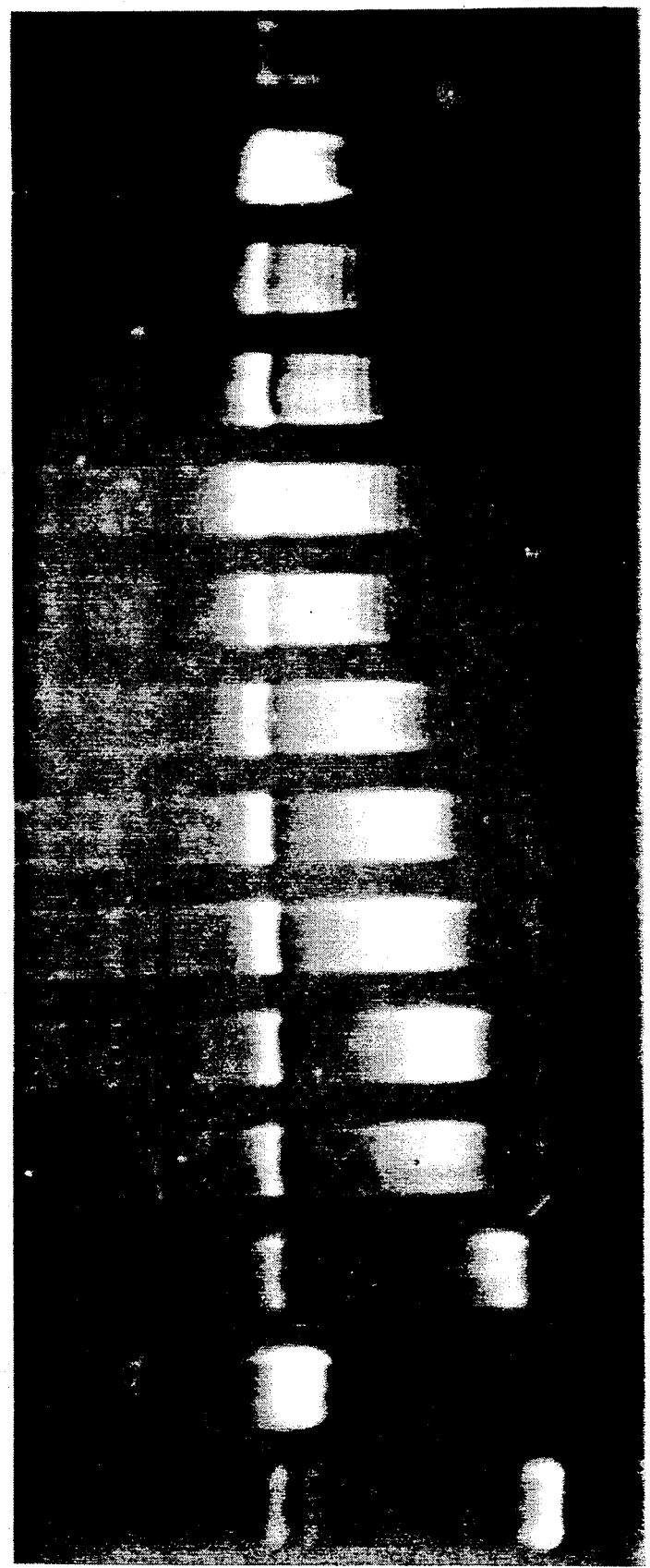
FIG. 11: Unwinding of pBR322 DNA by $Ru(bpy)_2(phi)^{2+}$ after incubation with topisomerase 1 in the presence of increasing concentrations of ruthenium complex as described in the Experimental Section. Lane 1 is DNA contron, Lane 2 is DNA and topoisomerase alone, Lanes 3-14 are DNA, topisomerase, and decreasing Ru concentrations from 5.74 μM to 1.57 μM. I and II denote forms I and II DNA.

Unwinding of Supercolied DNA: The amount of helical unwinding induced by a complex bound to closed circular DNA provides another measure of intercalative, binding. (92,93) Helix unwinding by a non-covalently bound species is determined by observing the change in superhelical density in a plasmid, after relaxation of the plasmid in the presence of bound complex by topoisomerase I and then removal of the complex. The heli unwinding angle is defined as the number of degrees of base pair unwinding per complex bound (see experimental). FIG. 11 shows the change in incubatin with increasing concentrations of $Ru(bpy)_2(phi)^{2+}$ in the presence of topoisomerase. Table 14 includes both the concentration of ruthenium complex added to unwind the plasmid 50% (11 out 22 superoils removed), and, for those complexes which show well behaved binding parameters, the corresponding unwinding angle per complex bound.

Several trends are apparent from these data. First, those complexes with appreciable binding affinity show reasonable values for the unwinding consistent with intercalation. $Ru(phen)_3^{2+}$ and $Ru(phen)_2(phi)^{2+}$ display unwinding angles of 19° (50) and 26°, respectively, and these may be compared to that of 26°, found for ethidium (87), a classical DNA intercalator. For the complexes which bind with lower overall binding strength, unwinding angles could not be reliably determined. The data indicate, however, the inverse correlation between binding constant and concentration of complex required for a constant amount of unwinding. Therefore it is likely that, for this series of weaker binding molecules, the unwinding angle per complex bound is quite similar. It is noteworthy that bound concentrations reflect both intercalation and surface binding and thus if surface binding contributes little to the unwinding, those complexes with a greater percentage in the surface boud from will show reduced apparent unwinding angles. $Ru(bpy)_3^{2+}$ which based upon spectroscopic results, neither intercalates nor surface-binds to the helix, shows little significant unwinding of the helix. The complexes $Ru(DIP)_2)phen)^{2+}$ and $Ru(phi)_2(bpy)^{2+}$ proved to be too insoluble for application of the unwinding assay. For the complexes possessing high binding affinity, a larger certainty inbound concentration and therefore unwinding angle exists. Here some effect fo the ancillary ligand may be seen $Ru()phen)_2(phi)^{2+}$, suggesting that the larger ancillary phen ligands may contribute to unwinding of the helix.

Effects of DNA Binding seen by Excited State Resonance Roman Spectroscopy:

The effects of DNA binding on the electronic structure of the complexes may also be probed by excited state resonance Raman spectroscopy, and this technique has provided some novel evidence in support of intercalative binding. FIG. 12 shows spectra for $Ru(bpy)_2\text{-}DIP^{2+}$ in the absence and presence of DNA. In the spectra of mixed ligand complexes, transitions were assigned earlier to excited states localized either on bpy or DIP. (95) Thus, the presence of an equilibrium between the two localized excited states was established. In particular the transitions centered at 1215 $cm^{-1}$ are dominated by bpy*. This equilibrium can be shifted on binding to DNA. In the presence of DNA, the intensity of the transitions coresponding to bpy* are considerably decreased relative to those for DIP*. Remarkably, though not covalently bound, the association with DNA sufficiently perturbs the excited state elctronic structire of the complex for detection by this technique. We interpret that decrease in bpy* excited state equilibrium toward DIP*. For this mixed ligand complex, only the DIP ligand, rather than bpy, is expected to intercalate into the helix. Perhaps as a result of binding to DNA, the energy of DIP* is lowered more so than is bpy with charge transfer occurring preferentially onto the intercalated DIP ligand.

One may also understand the red and blue shifts in emission assoiocated with binding to DNA by the mixed ligand complexes by considering these shifts in equilibria. For $Ru(bpy)_2DIP^{2+}$, the lower energy excited state involves transfer to the DIP ligand. (95) If DIP is the intercalating ligand, this state is lowered in energy, and, consistent with this idea, a red shift (10 nm) in emission is observed. In the case of $Ru(bpy)_2phen^{2+}$, the lowered energy excited state involves charge transfer onto the bpy ligand. (95) Since the phen ligand is the one which would intercalate and thus be lowered in energy, an overall blue shift of 9 nm is observed. The same arguments may explain the shifts observed for $Ru(phen)_2bpy^{2+}$ and $Ru(DIP)_2phen^{2+}$. For $Ru(phen)_2DIP^{2+}$ the direction of the shift found is unexpected, but this may reflect underlying contributions from surface binding.

II. $Rh(phi)_2(bpy)^{3+}$ Footprinting of Distamycin Results

Figure 13A:
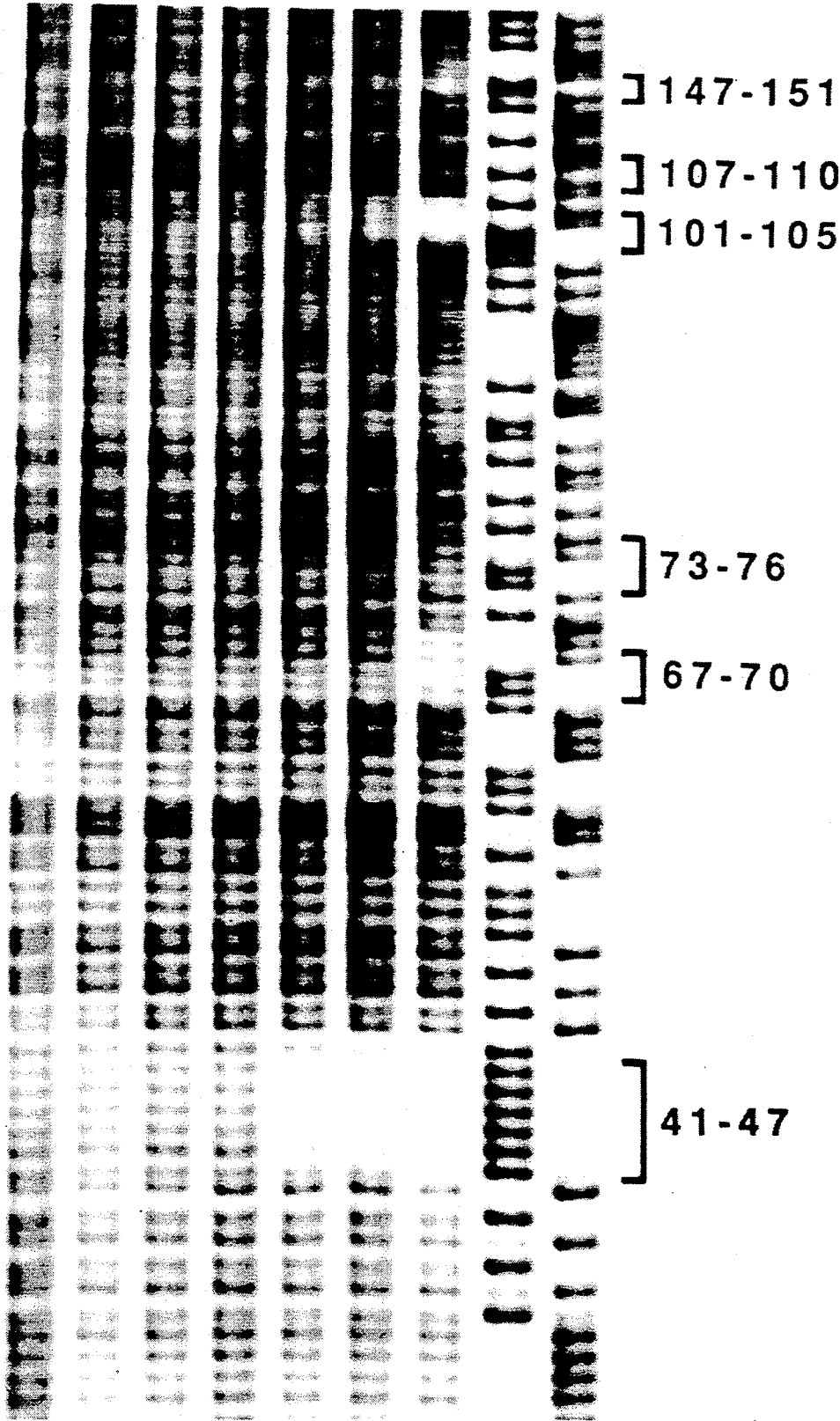
FIG. 13A, 13B$_1$, 13B$_2$, and 13C: (a). $Rh(phi)_2(bpy)^{3+}$ footprinting of distamycin. Lanes A and B: dark and light controls, respectively. Lanes C and D: in the absence of distamycin (C without 90° C. treatment after cleavage reaction); E, F, G, H, and I: in the presence of 0.125, 0.25 1.25, 2.5, and 12,5 μM distamycin, respectively, using 5'-end-labeled fragment and 7 min irradiation with a Hg/Xe lamp. Lanes J and K: Maxam-Gilbert A+G and T+C reactions, respectively. Footprinted regions are marked with brackets and numbers. (b). Densitometer scans of $Rh(phi)_2(bpy)^{3+}$ footprinting in the presence of distamycin (top, data from lane I of FIG. 1a) and in the absence of distamycin (bottom, data from lane D of FIG. 1a). Traces of light control and base pair numbers are given in each scan for reference. (c). Values of (Ic-Id)/Ic for footprinting of distamycin are plotted against base pair numbers for both 5'- and 3'- end-labeled strands. Data were taken from FIG. 1A. The sequence at the footprinted region is inset.
Figure 13C:
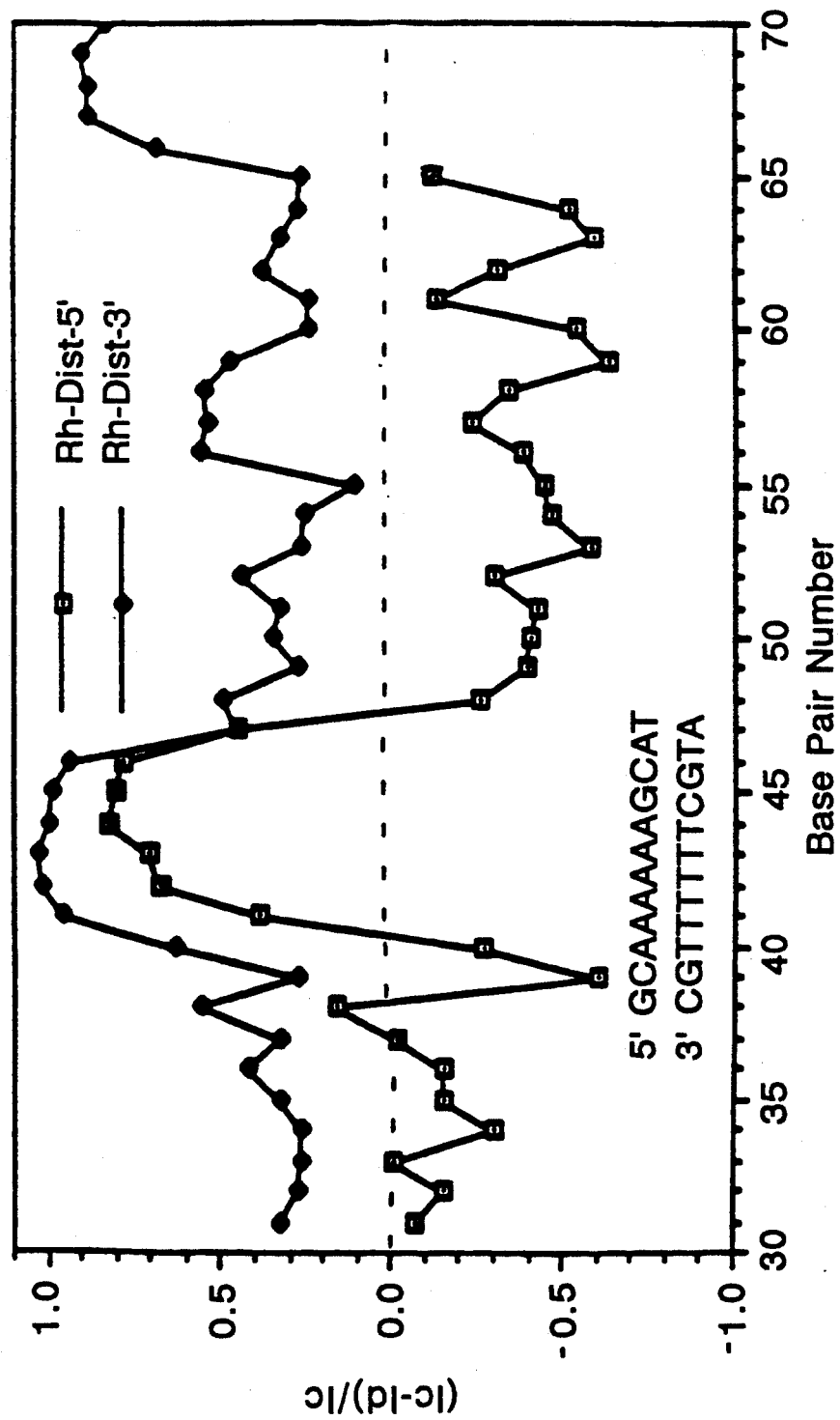
Figure 14A:
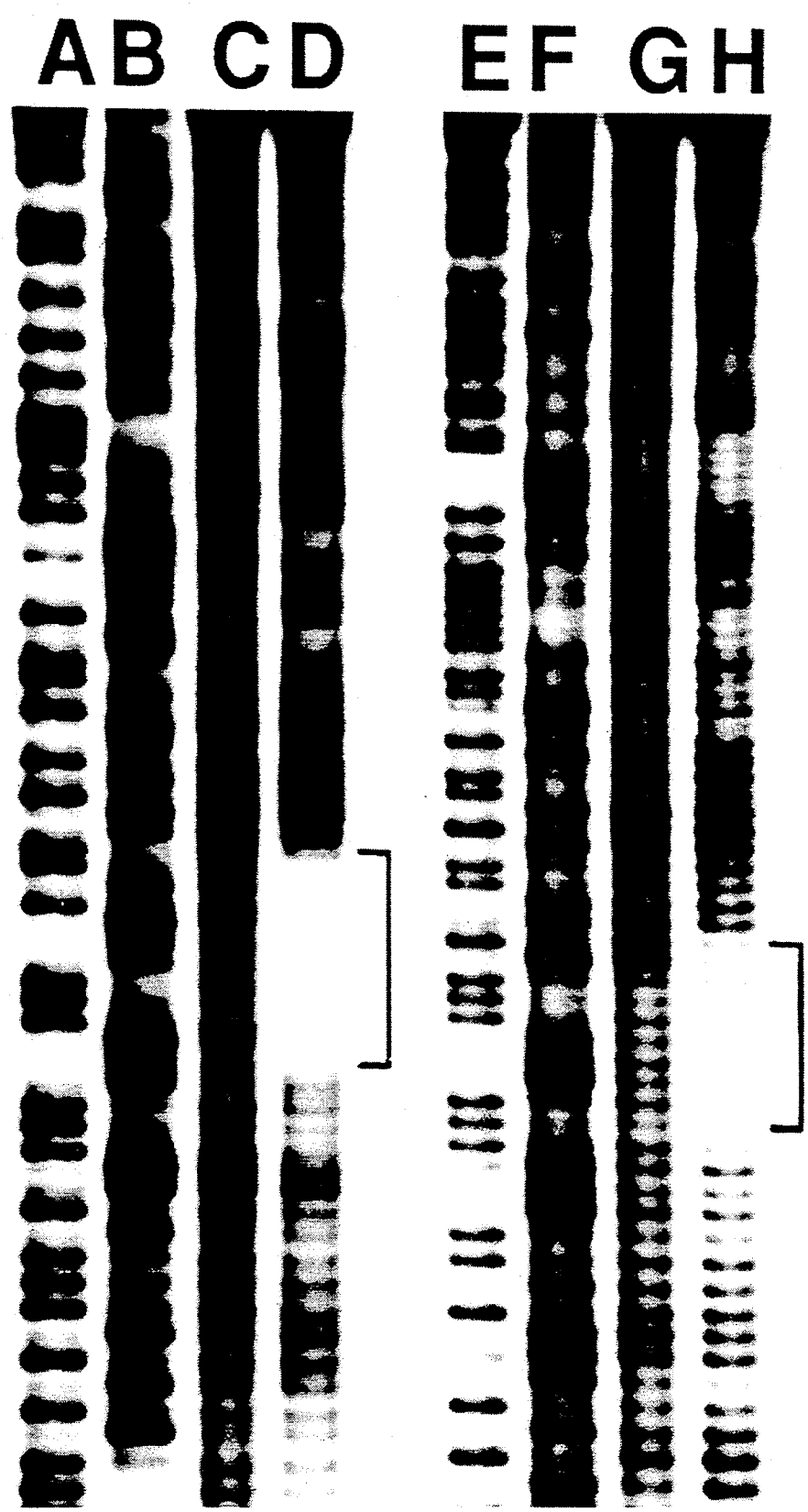
FIG. 14A, 14B, 14B$_2$ and 14C: (a) $Rh(phi)_2(bpy)^{3+}$ footprinting of EcoRI. Lanes A-D on 5'end-labeled fragment and E-H on 3'-end-labeled fragment. Lanes C and G: $Rh(phi)_2(bpy)^{3+}$ cleavage in the absence of distamycin. D and H: cleavage in the presence of EcoRI (60 units for lane D and 240 units for lane H) after 6 min irradiation with a Hg/Xe lamp. Lanes A and E: Maxam-Gilbert A+G reaction. Lanes B and F: T+C reaction. Footprinted regions are indicated by brackets. (b). Densitometer scans of $Rh(phi)_2(bpy)^{3+}$ footprinting of EcoRI on 5' end-labeled fragment in the presence (top) and absence (bottom) of the endonuclease, together with the light control lane. Base pair numbers are also given.
Figure 14C:
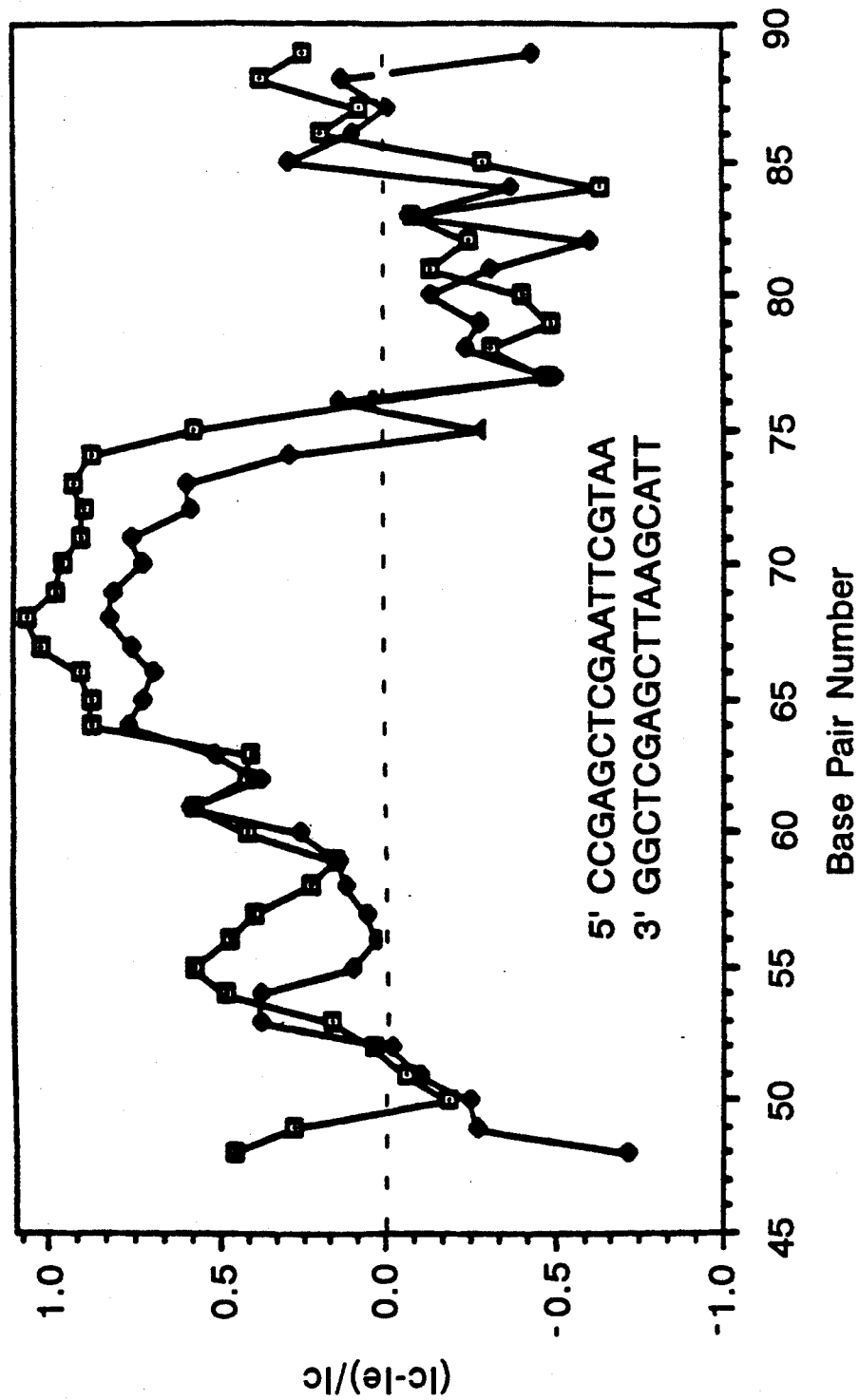

Footprinting of distamycin of a 5'-end-labeled DNA fragment is shown in FIG. 15a. Brackets denote regions where the DNA is protected from $Rh(phi)_2(bpy)^{3+}$ cleavage by distamycin. A clear, sharp footprint is seen at the strong $A_6$ binding site (41-47 bp) for distamycin and also at weaker distamycin binding sites AATT (67-70, 119-12), TAAT (73-76), AAATT (101-105), and TTAT (107-110). On the 3'-end-labeled fragment, corresponding results are obtained. At a higher concentration of distamycin (25 $\mu M$, drug/base pair ration = 1) and a lower concentration of the rhodium complex (6.5 $\mu l$ M, metal/base pair ration =0.26), a weak ATAT site and sites containing three AT base pairs can also be footprinted. FIG. 15 b shows densitometer traces of $Rh(phi)_2(bpy)^{3+}$ cleavage in the presence and absence of distamycin. Densitometer data wee also manipulated as described in Materials and Methods to yield FIG. 13c, a representation of high resolution footprintng at the A site by $Rh(phi)_2(bpy)^{3+}$ on both strands. For the 5'-end-labeled fragment, 5 bases (42–46) are strongly protected from cleavage and 2 bases (41 and 47) are weakly protected. For the 3'-end-labeled fragment, 6(41–46) and 1 (40) positions are strongly and weakly protected from cleavage, respectively. The protected region shows a single nucleotide shift to the 3'side, which is to be distinguished from the 2-3 pair 3'- shifts for footprinting of distamycin by MPE-Fe(II) or Cu(phen)$_{2+}$.

Rh(phi)$_2$(bpy)$^3$ + Footprinting of EcoRI

FIG. 16a shows the footprintng of EcoRI by Rh(phi)$_2$(bpy)$^{3+}$ on 5'-(lanes A–D) and 3'(lanes E–F) end-labeled fragments. A sharp footprint of the protein is clearly evident. Light bands within the footprint on the 3'labeled strand can be observed but they are apparent also in the light control (not shown). Densitometer scans are shown in FIG. 16b for cleavage by Rh(phi)$_2$(bpy)$^{3+}$ in the presence and absence of ECoRI, and FIG. 16c shows the values of $(I_c - I_e)/I_c$ for each band on both 3' and 5'-end-labeled strands. It is apparent from FIG. 16c that the footprinted region about the EcoRI site is 12 bases (64–75) in length on the 5'-end -labeled strands and 10 bases (64–73) on the 3'end-labeled strand. These footprinted regions are much smaller than those obtained with DNase I (17–18 base pairs) (18) and are in good agreement with the x-ray co-crystallographic data, where the protein is seen to be in contact with the DNA over 10 base pairs (24). A distinct asymmetry in cleavage either to the 3'-or 5' side is not evident here with the rhodium complex.

Footprinting experiments were also conducted with Rh(phi)$_2$(bpy)$^{3+}$ with the transilluminator is shown in FIG. 17. Despite slightly greater DNA light damage using this alternative light source, the footprinted region again spans 10 base pairs (64–73), which is in excellent agreement with results obtained using the Hg/Xe lamp. It is noteworthy that some hyperactivity by the rhodium complex is evident within the binding site in the absence of protein, and this reactivity, though reduced, is still present to some extent in the presence of protein (position 66). Nonetheless, densitometer scanning and subtraction of light controls yields footprints of equally high resolution to those obtained with a high power lamp.

Establishment of Optimal Conditions for Cleavage by Rh(phi)$_2$(bpy)3+

In order to establish the effect of different reaction conditions on the sequence-neutrality and intensity of Rh(phi)2(bpy)3+ cleavage, a series of experiments to characterize the cleavage were also conducted. The effect of varying the metal/base pair ratio is shown in FIG. 18 (lanes H-L and O), together with the effect of irradiation time (lanes F-H and L-N) and irradiation power (lanes J and R-V). As the Rh/DNA ratio decreases, cleavage by the complex shows increasing sequence selectivity. Although no clear consensus sequence is evident, sequences such as 5'-TATG-3'(51-48- and 37-34 bp) as well as, more generally, alternating purine-pyrimidine sequences are cleaved more strongly relative to background at low concentrations of Rh(phi)2(bpy)3+. DNA cleavage by the complex at such alternating sequences is still efficient at rhodium concentrations as low as 50 mM. Cleavage at pyrimidine bases is slightly more efficient than at purine bases. At metal/base pair ratios of >0.5, however, the cleavage reaction is almost completely sequence neutral, and certainly random enough for purposes of footprinting.

Unlike the effect of varying the metal/base pair ratio, differences in irradiation time or power do not cause change in cleavage specificity of the metal complex. As can be seen from FIG. 18, changes in irradiation time or power are roughly proportional to the extent of cleavage. Varying the wavelength of irradiation also causes only little change n cleavage pattern. Shorter wavelength light (300–320nm) is much more efficient for activating Rhphi)$_2$(bpy)$^{3+}$ than is longer-wavelength light (340-365 nm). It is impractical to use light below 310 nm, however, because photodamage in the absence of the rhodium complex occurs, which introduces background noise.

The effect of different buffers on the cleavage reaction was also examined at pH7 (data now shown). No changes in specificity or intensity of the cleavage reaction are observed in any of the following buffers at pH7: (1) 50 mM sodium cacodylate(—HCl), (2) 50 mM potassium phosphate, (3) 50 nM Tris(—HCl), and (4) 50 mM Tris(—HCl), 20 mM sodium acetate, and 18 mM sodium chloride. When the reaction is carried out at pH 6 (50 mM sodium cacodylate buffer) or pH 8 (50 mM Tris-(—HCl)buffer), there are few detectable differences in the Rh(phi)$_2$(bpy)$^{3+}$ cleavage pattern. Sequence-neutrality of the photocleavage reaction is also unaffected by the temperature of incubation varied from 0° C. to 37° C.

Figure 5A:
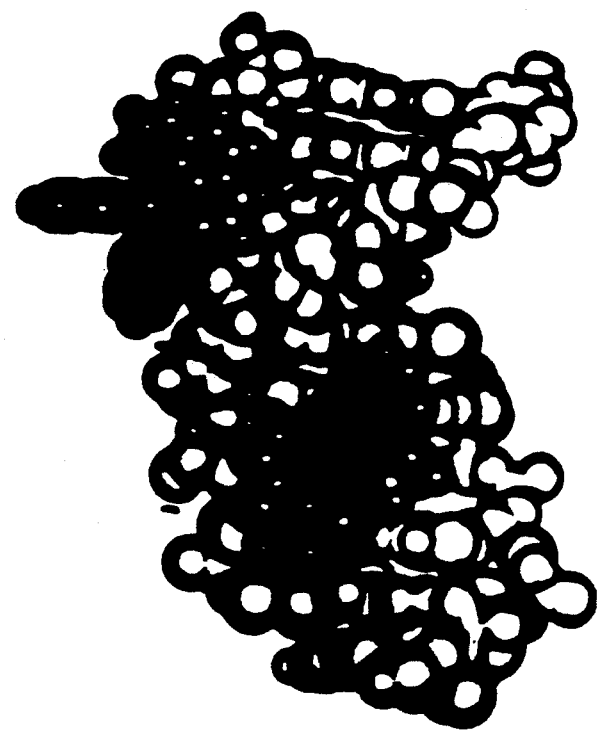
FIG. 5A and 5B: Models for the two non-covalent binding interactions of the octahedral metal complexes with DNA. Shown are Δ-Ru(phen)$_3$2+ (bottom) intercalated into the major groove and Ω-Ru(phen)$_3^{2+}$ (top) surface-bound against the minor groove of the DNA helix. FIG. B displays the same models after a 90° rotation about the helical axis. Graphics were performed on an Evans and Sutherland PS390 terminal using the Macromodel program.
Figure 5B:
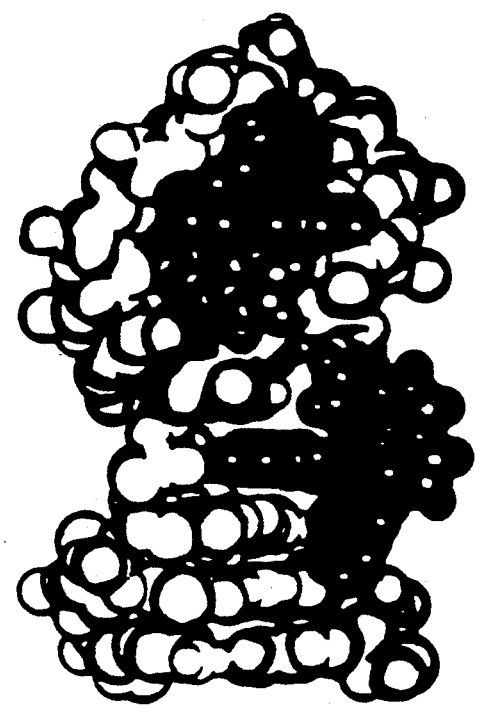

Effect of Commonly Used Biochemical Reagents on Cleavage by Rh(phi)$_2$(bpy)$^{3+}$ The effect of various salts (NaCl, MgCl$_2$, CaCl$_2$) on the photocleavage reaction is shown in FIG. 19 (lanes F–O). The photocleavage reaction is not inhibited in 100 mM NaCl, 10 mM MgCl$_2$, or 10 mM CaCl$_2$, salt concentrations necessary for in vivo applications and sometimes required with particular DNA-binding proteins. At higher concentrations of these salts, specific bands become apparent and these are identical to those observed at low Rh(phi)$_2$(bpy)$^{3+}$ concentration, consistent with a decrease in binding affinity at very high salt concentrations. Cleavage is not altered in the presence of 1 mM EDTA, although some GC selectivity is apparent in the presence of 10–1000 mM EDTA (FIGS. 5 lanes P–R). Dithiothreitol at concentrations of 1 mM or higher causes only slight changes in relative band intensities while another reducing agent, 3-mercaptopropionic acid, has no effect up to 10 mM (data not shown). Bovine serum albumin (60 µl/ml) or 10% glycerol (FIG. 20 lanes S–U) has no affect on photocleavage by Rh(phi)$_2$(bpy)$^{3+}$.

Discussion

The result of these varied experiments on the series of mixed ligand complexes of ruthenium(II), when taken together, provide a detailed picture of factors affecting noncovalent binding of the complexes to the helix. The complexes, excepting Ru(bpy)$_3^2$, all appear to intercalate and surface-binding into DNA. This conclusion is based upon the effects of hypochromism, the increases in emission intensitites and excited state lifetimes, the helical unwinding, and the excited state resonance Rman experiment. (96) The chiral discrimination found in binding these complexes to DNA lends further support to the intercalative binding model and more specifically to the notion that the binding of this family of rigid complexes with respect to the helix is likely to be quite similar. (97) In this series of mixed ligand complexes, we have varied geometry, hydrophobicity, size, dipole moments, and hydrogen bonding ability, and we may therefore examiner how each of these factors contribute to DNA binding.

Intercalation and Surface Binding: For the mixed ligand complexes, the tendencies of each of the ligands to intercalate may be compared. For the series $RuX_2bpy^{2+}$, $RuX_2phen^{2+}$, $RuX_2phen^{2+}$, $RuX_2DIP^{2+}$, $RuX_2phi^{2+}$, whee the ancillary, non-intercalated ligands, X, are kept constant, the binding constants increase in the series $bpy << phen \leq DIP << phi$. This variation likely reflects the differing ability of the ligands to stack and overlap well with the base pairs. The phi ligand is flat, large in surface area, and has a geometry which permits substantial overlap with the base pairs (rather than one where the majority of the $\pi$ orbital framework would lie in the center of the helix, between the DNA bases). Hence the phi ligand is well suited for intercalation, and for mixed ligand complexes it would be the phi ligand which would be expected preferentially to intercalate. The DIP ligand, similar in expanse to that of phi, is not expected to be flat, with phenyl groups instead twisted out of the phenanthroline plane, (98) and this lack of planarity diminishes the favorability of the ligand for intercalation. Nonetheless, the data are consistent with intercalation by this ligand. The DIP ligand, moreover, may be favored over phen for intercalation into the helix. Binding data from absorption titrations for $Ru(phen)_3^{2+}$ and $Ru(phen)_2DIP^{2+}$ show increased binding affinity upon substitution with DIP, and both emission enhancements and red shifts in absorption are greater for analoguous DIP versus phen complexes. That this affinity derives from intercalation rather than from added hydrophobic surface binding is not definitively established, however, and therefore the relative intercalative abiltiy of DIP versus phen complexes if difficult to assess. The phen ligand can, nonetheless, also intercalate into the helix, though the ancillary ligands preclude substantial overlap with the base pairs. Inspection of models shows that, owing to the overhanging hydrogen atoms (2 and 3 positions) from the ancillary ligands, only the outer third of the phenanthroline ligand (5 and 6 positions) is available for stacking. Thus only a partial insertion of the ligand is likely. For bpy, this stacking region is absent. On this basis, it is reasonable to understand why the bpy ligand shows only an electrostatic association with DNA, and no detectable intercalation.

Effects of Ancillary Ligands: The primary effect of the ancillary ligand is in altering the extent of enantioselectivity. As was found earlier (29) in comparisons of $Ru(phen)_3^{2+}$ and $Ru(DIP)_3^{2+}$, increased asteric bulk of the ancillary ligand increases the enantioselectivity for intercalation of the isomer into right-handed DNA. Given intercalation into the helix by one ligand, we can also compare how different ancillary ligands add to or detract from the overall binding affinity. One bulky hydrophobic ligand which can intercalate adds to the stability of the bound complex, but the second bulky ligand, which would necessarily occupy the ancillary position, prerpendicular to the groove, adds no further stability. $Ru(DIP)_2phen^{2+}$ shows binding similar to that of $Ru(phen_2DIP^{2+}$, and $Ru(phi)_2bpy^{2+}$, actually displays decreased affinity for DNA relative to $Ru(bpy)_2ph^{2+}$. For these ancillary ligands, steric interactions may interfere with how deeply the intercalated ligand may stack into the helix. Additionally, the increased hydrophobicity of the complexes leads to sef-stacking in solution, and this effect may reduce the net binding affinity. (91) Interestingly, symmetric substitutions provide a different picture. In comparing $Ru(bpy)_2phen^{2+}$ with $Ru(phen)_3^{2+}$, or $Ru(bpy)_2DIP^{2+}$ with $Ru(phen)_2DIP^{2+}$, one finds increased DNA binding affinity with increasing hydrophobicity of the ancillary ligands. (100) This observation may in part reflect a greater tendency of phen for surface binding. However the orientations of the intercalated complexes will certainly affect their abiltiy to exclude water from the hydrophobic surfaces of the ancillary ligands, and this may be particularly important in stabilizing symmetric binding molecules.

Hydrogen Bonding: The series of complexes studied also afford the opportunity to examine whether substitutions of ligands which contain potentially hydrogen bonding groups stabilize the complexes bound to DNA. Both the red shift in absorption titrations and the finding of enantioselective binding of the [] isomer suggest that $Ru(5-NO_2-phen)_3^{2+}$ may bind to DNA intercalatively. One might have expected that with the larger heterocyclic surface of 5-NOz-phen, the ligand might even have been favored for intercalation. Inspection of models suggests that if intercalated, or indeed even if surface bound, the nitro-groups on the ancillary ligands could be aligned appropriately for hydrogen bonding to base positions. The complex, however, bind only poorly to DNA. In fact the binding constant is comparable to that of $Ru(bpy)_3^{2+}$ and thus the major source of stabilization is likely to be electrostatic. A similar conclusion may be drawn based upon a comparison of binding constant of $Ru(phen)_2bpy^{2+}$ and $Ru(phen)_2flone^{2+}$. For the diazafluoreneone ligand, the oxygen atom is oriented perpendicular to the main axis of phenanthroline and thus the orientation of the hydrogen bonding acceptor relative to that of either groove containing hydrogen bonding donors differs from that in $Ru(5-NO_2-phen)_3^{2+}$. Yet, again no increased stabilization is detected Instead the binding affinity for $Ru(phen)_2flone^{2+}$ is indistinguishable from that for $Ru(phen)_2bpy^{2+}$. It appears, then, that the substitution of potential hydrogen bonding acceptors onto the phenanthroline ligands provides no additional source of stabilization. The same observation applies to our single example of a hydrogen bonding donor on an ancillary ligand, $Ru(phi)_2bpy^{2+}$. For this complex, equilibrium binding constants are in the range of those for $Ru(phen)_2phi^{2+}$.

Thus, although specific hydrogen interactions along the DNA helix are possible, there is apparently no net increase bonding stabilization relative to that where the DNA and complex are independently solvated. In binding to DNA, some new hydrogen bonds between DNA and complex may be made, but these are at the expense of hydrogen bonds for each with solvent.

Overall Factors Contributing to Stabilization: If one compares the various factors that contribute to stabilizing the metal complexes on the DNA helix, it appears that the most significant factor is that of molecular shape. Those complexes which fit most closely against the DNA helical structure, those in which Van der Waals interactions between complex and DNA maximized, display highest binding affinity. The phi ligand, for example, is constructed to provide substantial overlap of its aromatic surface with that of the DNA base pairs, and binding constants for those complexes with phi is intercalated ligand show more than two orders of magnitude increase in binding affinity. The phi ligand is not well suited as an ancillary substitution by DIP rather than by phi. This notion is further exemplified in the differences between symmetrically and non-symmetrically arranged ancillary ligands, or even more simply in comparisons of binding modes and affinities for them versus bpy complexes.

Table 15 summarizes two characteristics of the complexes which may be useful to consider: their solubility in buffer and their water accessible surface areas. (101) Some correlations between these parameters and the intrinsic binding constants of the complexes may be made, and also some deviations are apparent. Certainly the hydrophobicity of a complex appears to be an important criterion in determining binding affinity. Those complexes with more surface area for interactions with DNA and for which interactions with DNA rather than with water are favored display higher overall intrinsic binding constants. Hydrogen bonding functionalities do not appear to be critical to overall binding stability. Indeed, $Ru(5-NO_2-phen)_3^{2+}$ and $Ru(phen)^{2+}_2$. flone show binding affinities much lower than would be expected based upon their solvent accessible surfaces. Since binding to DNA limits hydrogen bonding interactions of the free complex with water, the overall free energy change in binding to DNA is reduced by this factor. In contrast, the free energy change in binding to DNA is increased for hydrophobic complexes because of the entropy gain associated with release of water solvating the hydrophobic ligands. Binding affinities for the DIP complexes are, however, not as high as would be expected based upon calculations of accessible surface area, and this is likely because the ligand is not planar. Hydrophobicity is an important factor, but the shape of the complex, the disposition of ligands relative to the helix and how the ligands fit against the DNA surface, appears to be critical for both intercalative and surface-bound interactions.

TABLE 15

Characteristic of Complexes

| Complex | Solubilities in Buffer$^a$ (mM) | Water-Accessible Surface Area$^b$ ($A^2$) |
|---|---|---|
| $Ru(bpy)_3^{2+}$ | 94 (4.4) | 687.3 |
| $Ru(bpy)_2(phen)^{2+}$ | 200 (24.) | 702.6 |
| $Ru(phen)_2(bpy)^{2+}$ | 133. (1.8) | 719.6 |
| $Ru(phen)_3^{2+}$ | 159. (5.3) | 736.7 |
| $Ru(5-NO_2phen)_3^{2+}$ | 28.2 (.27) | 862.6 |
| $Ru(phen)_2(flone)^{2+}$ | 60. (2.2) | 738.9 |
| $Ru(bpy)_2(DIP)^{2+}$ | 73. (2.5) | 916.4 |
| $Ru(phen)_2(DIP)^{2+}$ | 9. (1.2) | 950.2 |
| $Ru(DIP)_2(phen)^{2+}$ | 0.18 (.01) | 1166.7 |
| $Ru(bpy)_2(phi)^{2+}$ | 15. (2.0) | 768.3 |
| $Ru(phen)_2(phi)^{2+}$ | 0.17 (.01) | 809.4 |
| $Ru(phi)_2(bpy)^{2+}$ | 0.018 (.001) | 854.0 |

$^a$Measured from saturated solutions in 5 mM Tris, 50 mM NaCl, pH 7.5 after 24 hrs., 25° C. Solubilities are given for the chloride salts. Standard deviations are given in parentheses.
$^b$See reference 36.

Shape and hydrophobicity are likely to be important factors governing also the ability of other small molecules to bind to DNA, as well. It must be noted, however, that these studies do not directly provide insight into those factors which may govern differential DNA site-selectivity. Site-specific DNA cleavage studies using analogous mixed ligand complexes of rhodium (III) are in progress to address that issue.

Utility of Translocation Metal Complexes: Coordination chemistry could play a unique role in the development of new compounds which bind site-specifically to biopolymers. Given the structural flexibility and variable dimensionality of transition metal complexes, one may design and readily prepare a different repertoire of shapes for interaction with DNA than those obtained through organic synthesis alone. Mixed ligand complexes of ruthenium(II) are particularly well suited to these systematic investigations of recognition. The octahedral transition metal ion provides the core, in fact a chiral center, for a rigid well defined structure of coordinated ligands. The ligands may be varied in a synthetically convenient fashion to produce a family of substitutionally inert DNA bonding molecules, with a range of ligand functionalities. The intense coloration and rich excited state properties of the complexes provide a sensitive spectroscopic handle to monitor binding interactions. These and similar complexes may therefore be useful also in studies of recognition of other biopolymers.

FIG. 18 summarizes the footprinting results using $Rh(phi)_2(bpy)^{3+}$ at both the distamycin and EcoRI binding sites on the restriction fragment examined. It is apparent that $Rh(phi)_2(bpy)^{3+}$ produces well defined, highly resolved footprints of both a small peptide binding in the minor groove and a large DNA-binding protein. The binding sites delineated by the rhodium footprints both for distamycn and EcoRI are in excellent agreement with the crystallographic data for these DNA-binding molecules in cocrystals with olignucleotides (24,25). The crystal structures indicate that distamycin and EcoRI having binding site sizes of six and ten, respectively. The footprints obtained with $Rh(phi)_2(bpy)^{3+}$ therefore are among the most precise observed thus far using footprinting methodology. Importantly the resolution is maintained even when $Rh(phi)_2(bpy)^{3+}$ is photoactivated using a simple trans-illuminator, making this technique accessible to almost any molecular biology laboratory.

There are several features of the photocleavage reaction promoted by $Rh(phi)_2(bpy)^{3+}$ which contribute to the resolution and clarity of its footprints. The first important characteristic for any successful footprintng reagent is the sequence neutrality in its cleavage. $Rh(phi)_2(bpy)^{3+}$ cleaves DNA quit uniformly; some sequence selectivity is apparent with the reagent only at nanomolar concentrations. Since cleavage is obtained at all nucleotides, single-nucleotide footprinting resolution is possible. Two interrelated features likely to be important in achieving the sharpness of the rhodium footprint are the rigidity of the complex and its apparent lack of a diffusing species to mediate the cleavage reaction. Mechanistic studies of phi complexes of rhodium(III) suggest that cleavage occurs as a result of a direct hydrogen abstraction from the sugar by a ligand radical generated by photolysis. Cleavage reactions with $(Rh(phen)_2phi^{3+}$, a close analogue which shows some sequence selectivity, furthermore reveals single nucleotide cuts rather than a distribution of cuts at each binding site as is common with reagents that cleave DNA in reactions mediated by hydroxyl radicals (26) or single oxygen (27). The sharpness in footprint with $Rh(phi)_2(bpy)^{3+}$ may then result from the fact that the rigid rhodium complex can occupy and cleave directly at all sites that are not obstructed by the DNA binding agent and cannot cleave directly or indirectly within the obstructed region since the reagent does not cleave through a diffusible intermediate and lacks a floppy appendage which itself contains the cleaving functionality. The footprint with $Rh(phi)_2(bpy)^{3+}$ is, then, inherently "all or none", producing a high contrast image. The pattern of cleavage obtained would contrast that found with Fe(EDTA)$^{2-}$, for example, which is mediated by hydroxyl radicals. With Fe(EYta)$^{2-}$ information has ben obtained regarding subtle structural details associated with how domains within a DNA-binding protein associate with the helix rather than the edges of the protein binding site. Rh(phi)$_2$(bpy)$^{3+}$ is not likely to be useful for such experiments. Instead the complex is extremely sensitive in sharply delineating the boundaries of a protein binding site with high contrast.

Another important aspect contributing to the versatility of Rh(phi)$_2$(bpy)$^{3+}$ as a footprintng reagent is the fact that the complex appears to bind to helix by intercalation. Although a crystal structure is lacking on the phi complexes bound to oligonucleotides, helix unwinding results on a series of ruthenium complexes containing the phi ligand (28) as well as on Rh(phi)$_2$(bpy)$^{3+}$ itself (29) indicate helix unwinding angles that are comparable to ethidium. Intercalative binding by a footprinting reagent increases the range of applicability for the reagent, since intercalators can sense binding molecules in both the major and minor grooves. An intercalative interaction requires local helical unwinding and proteins bound to the one face of a helix clamp it shut against intercalation from the other side. Groove binding agents, in contrast, can sense only those molecules which bind in the same groove, unless binding to the other groove causes an appreciable structural alteration. Hydroxyl radical cleavage generated by Fe(EDTA)$^{2-}$, which does not bind to the helix itself, apparently reacts preferentially with minor groove protons, leading to a substantial weighing in footprints to those structural perturbations which occur in the minor groove. Since an intercalator can sense binding molecule in either groove, it becomes of secondary importance whether the intercalator itself binds from either the minor or major groove. Based upon analogy to other phi complexes of rhodium (III) as well as upon results with other metallointercalating agents, it is possible that this footprinting reagent is also unique in binding from the major groove (17,30). It should be noted in this context that the distamycin footprint with Rh(phi)$_2$(bpy)$^{3+}$ shows a single nucleotide shift to the 3' side in the protection pattern and no pattern asymmetry is clearly apparent in the EcoRI footprint. For the distamycin binding site, other footprinting reagents which appear to bind from the minor groove have shown 3'-shifts with a larger magnitude (2-3 nucleotides) (9,31).

Figure 9:
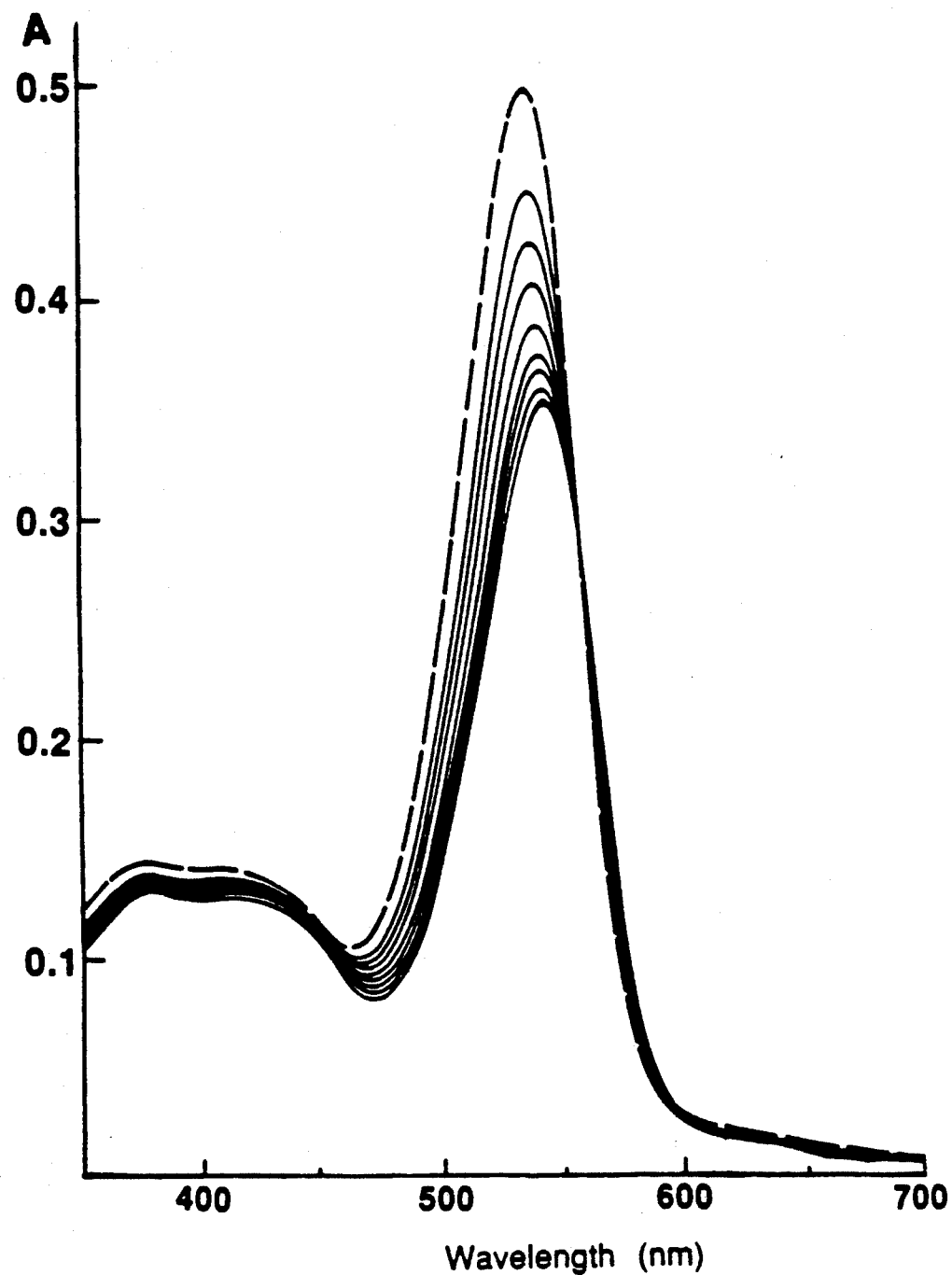
FIG. 9: Visible absorption spectra of Ru(phen)$_2$(phi)$^{2+}$ (10μM) in the absence (---) and presence (-----) of increasing amounts of DNA (0.56 nucleotides/metal per scan).

Comparisons in footprinting of distamycin are made in FIG. 9 between Rh(phi)$_2$(bpy)$^{3+}$ and other popular footprinting reagents, MPE-Fe(II), DNase I and Cu(phen)$_2$+. Comparative footprinting of EcoRI is shown in FIG. 10, although Cu(phen)$^{2+}$ could not be included as it failed to footprint the protein in our hands (and also in the literature (22)). This result is not surprising given that the copper complex likely binds without intercalating in the minor groove. DNase I footprints yield an exaggerated ligand site size, with distamycin and EcoRI, due to both the sequence selectivity and large size of the enzyme. Cu(phen)$_2$+ is a small reagent which could conceivable footprint distamycin to high resolution. However, as is apparent in FIG. 7d, Cu(phen)$_2$+ lacks the necessary sequence neutrality.

The footprinting reagent most similar to Rh(phi)$_2$(bpy)$^{3+}$ in resolution and sequence-neutrality is MPE-Fe(II). As shown in FIGS. 9b and 10b, clear footprints of distamycin and EcoRI are obtained with this reagent. The sequence neutrality in reactions with MPE-Fe(II) may be somewhat higher than that with the rhodium complex. The footprinting pattern with MPE-Fe(II) is also of comparable resolution to that found with Rh(phi)$_2$(bpy)$^{3+}$ but may not be as sharp as is seen with the rhodium complex, likely because the reaction is mediated by a diffusible species. Another notable difference between Rh(phi)$_2$(bpy)$^{3+}$ and MPE-Fe(II) is that the latter shows a greater propensity to detect weak distamycin binding sites at comparable concentrations. This is probably a result of the lower binding constant of MPE-Fe(II) to DNA[1.5 × 10$^5$M$^{-1}$ for MPE-Ni(II)](9). One can derive the binding constant for Rh(phi)$_2$(bpy)$^{3+}$ to the distamycin binding site by using a kinetic treatment such as that applied to ligand binding in the presence of a competitive inhibitor (32), and such an analysis yields an apparent Rh(phi)$_2$(bpy)$^{3+}$ binding constant to the A$_6$ site of 10$^6$-10$^7$ M$^{-1}$. This calculation is also consistent with the observation that DNA (5 $\mu$M bp) can be efficiently cleaved by Rh(phi)$_2$(bpy)$^{3+}$ at concentrations of 50 nM. Taken together, the binding data indicate that Rh(phi)$_2$(bpy)$^{3+}$ has a higher association constant than MPE-Fe(II) to B-DNA.

Besides the quality of its footprints, an important practical advantage in using Rh(phi)$_2$(bpy)$^{3+}$ for footprinting is simply is ease and range of handling. The complex is stable indefinitely in the solid state or stored as a frozen aqueous solution. It is not inhibited by moderate concentrations of divalent cations, EDTA, reducing agents, or glycerol. No complicated procedures or highly reactive species are required for the cleavage reaction, and clear footprinting may be obtained over a wide range of ligand and Rh(phi)$_2$(bpy)$^{3+}$ concentrations. These characteristics contrast Rh(phi)$_2$(bph)$^{3+}$ with reagents that require chemical activation such as Cu(phen)$_2$ and MPE-Fe(II).

In summary, photoactivated cleavage with Rh(phi)$^{2+}$(bpy)$^{3+}$ permits high sensitivity, clear resolution, wide applicability and excellent control in footprinting experiments of DNA-binding molecules. Since Rh(phi)$_2$(bpy)$^{3+}$ can be used with common UV light sources, the requirement for photolysis should be an advantage rather than an inconvenience. Perhaps most importantly, photofootprinting reagents such as Rh(phi)$_2$(bpy)$^{3+}$ may lend themselves especially well to footprinting DNA-bound proteins within living cells.

It appears then that luminescence is observed only when the ruthenium complex is intercalated in (or perhaps otherwise protected by) the nucleic acid structure. Similarly when Ru(bpy)$_2$(dppz)$^{2+}$ (10 $\mu$M) was mixed with 100 $\mu$M poly r(AU).r(AU) (buffer R) no luminescence ($\lambda_{irr}$=482 nm) was observed under conditions. This result is consistent with the absence of intercalation we found of ruthenium complexes with A-form RNA[43]. This demonstrates that the complex is very specific in the helical DNA it will bind. The relative luminescence of ruthenium complexes in the presence of various helical DNA's under varying conditions is shown in Table 16.

In conclusion a new luminescent probe for the various structures of DNA has been developed. It has been observed that aRu(bpy)$_2$(dppz)$^{2+}$ binds to both B and Z-form DNA that this complex displays different luminescence in the absence of DNA. The polarization experiments describe that the complex not only intercalates into the Z-form but is also held more rigidly by Z-form than by the analogous B-form. In both forms of DNA the complex is bound in a ration of 1:10 metal complex:base pairs.

One interesting application is the binding of this complex to DNA that has been electrophoresed in a agarose gel. In side-by-side studies, $Ru(bpy)_2(dppz)^{2+}$ and ethidium were found to stain DNA imbedded in the agarose gels through luminescence upon illumination from below. This complex has an advantage over the conventional ethidium-bromide stain in that there is no background luminescence from the complex bound to agarose, therefore, destaining is not required ever[44].

$Ru(phen)_2(dppz)^{2+}$, and $Ru(dip)_2(dppz)^{2+}$ seem have similar behavior as described above. In preliminary studies these complexes have been shown to luminesce only in the presence of DNA but not in the presence of $H_2O$ (or Buffer) alone[44]. We are presently tethering this complexes, $Ru(bpy)_2(dppz)^{2+}$, $Ru(dppz)_2phen^{2+}$, and $Ru(phen)_2(dppz)^{2+}$ to oligonucleotides to develop non-radioactive luminescent DNA probes for both heterogeneous and homogeneous assay systems. The probes, constructed in this way should luminesce only upon finding its target sequence.

TABLE 16

The Relative Luminescence of $Ru(bpy)_3(dppz)^{2+}$*
in Various Solvents and in the presence of DNA

| Solvent | DNA | Temp | Rel. Lumi. |
|---|---|---|---|
| $H_2O$ | — | 25 | — |
| Buffer** | — | 25 | — |
| $CH_3OH$ | — | 250 | 0.23 |
| iso-propanol | — | 25 | 1.00 |
| iso-propanol | — | 75 | 0.81 |
| Buffer** | CT DNA | 25 | 0.61 |
| Buffer** | CT DNA | 35 | 0.06 |
| Buffer** | CT DNA | 45 | 0.59 |
| Buffer** | CT DNA | 55 | 0.55 |
| Buffer** | CT DNA | 70 | 0.47 |
| Buffer** | CT DNA | 90 | 0.23 |
| Buffer | CT DNA | 25 | 0.55 |
| Buffer | CT DNA | 75 | 0.53 |
| Buffer | poly d(GC) · d(GC) | 25 | 0.72 |
| Buffer | poly d(AT) · d(AT) | 25 | 0.68 |
| Buffer | poly r(AU) · r(AU) | 25 | 0.01 |

*$Ru(bpy)_2(dppz)^{2+}$ 10 μM
Buffer** 0.5 mM NaCl, 0.05 mM Tris-OH, ph = 7.0
Buffer 50.0 mM NaCl, 5.0 mM Tris-OH, pH = 7.0

REFERENCES

1. Galas, D. J. and Schmitz, A. (1978) Nucl. Acids Res. 5, 3157-3170.
2. Dervan, P. B. (1986) Science 232, 464-471.
3. Tullius, T. D. (1987) Trends Biochem. Sci. 12, 297-300.
4. Sigman, D. S. (1986) Accts. Chem. Res. 19, 180-186.
5. Van Dyke, M. W., Roeder, R. G. and Sawadogo, M. (1988) Science 241, 1335-1338. Kownin, P., Bateman, E. and Paule, M. R. (1987) Cell 50, 693-699.
6. Drew, H. R. and Travers, A. A. (1984) Cell 37, 491-502. Suggs, J. W. and Wagner, R. W. (1986) Nucl. Acids Res. 14, 3703-3716. Suck, D., Lahm, A. and Oefner, C. (1988) Nature 332, 464-468.
7. Jessee, B., Gargiulo, G., Razvi, F. and Worcel, A. (1982) Nucl. Acids Res. 10, 5823-5834. Veal, J. M. and Rill, R. L. (1989) Biochemistry 28, 3243-3250. Veal, J. M. and Rill, R. L. (1988) Biochemistry 27, 1822-1827. Kobashi, K. (1968) Biochim. Biophys. Acta 158, 239-245. Yoon, C., Kuwabara, M. D., Law, R., Wall, R. and Sigman, D. S. (1988) J. Biol. Chem. 263, 8458-8463.
8. Ward, B., Skorobogaty, A. and Dabrowiak, J. C. (1986) Biochemistry 25, 6875-6883. Ward, B., Skorobogaty, A. and Dabrowiak, J. C. (1986) Biochemistry 25, 7827-7833. Dabrowiak, J. C., Ward, B. and Goodisman, J. (1989) Biochemistry 28, 3314-3322. Ward, B., Rehfuss, R., Goodisman, J. and Darbowiak, J. C. (1988) Biochemistry 27, 1198-1205.
9. Van Dyke, M. W.,Hertzberg, R. P. and Dervan, P. B. (1982) Proc. Natl. Acad. Sci. USA 79, 5470-5474. Hertzberg, R. R. and Dervan, P. B. (1982) J. Am. Chem. Soc. 104, 313-315. Hertzberg, R. P. and Dervan, P. B. (1984) Biochemistry 23, 3934-3945.
10. Van Dyke, M. W. and Dervan, P. B. (1983) Nucl. Acids Res. 11, 5555-5567.
11. Hurley, L. H., Lee, C. -S., McGovren, J. P., Warpehoski, M. A., Mitchell, M. A., Kelly, R. C. and Aristoff, P. A. (1988) Biochemistry 27, 3886-3892.
12. Cartwright, I. L. and Elgin, S. C. R. (1986) Mol. Cell. Biol. 6, 779-791. Gunderson, S. I., Chapman, K. A. and Burgess, R. R. (1987) Biochemistry 26, 1539-1546. Pruijn, G. J. M., van Miltenburg, R. T., Claessens, J. A. J. 3102.
13. Tullius, T. D., Dombrowski, B. A., Churchill, M. E. A. and Kam, L. (1987) Methods in Enzymology 155, 537-558. Tullius, T. D. and Dombroski, B. A. (1986) Proc. Natl. Acad. Sci. USA 83, 5469-5473.
14. Becker, M. M., and Wang, J. C. (1984) Nature 309, 682-687. Becker, M. M., Lesser, D., Kurpiewski, M., Baranger, A. and Jen-Jacobson, L. (1988) Proc. Natl. Acad. Sci USA 85,6247-6251. Selleck, S. B. and Majors J. (1988) Proc. Natl. Acad. Sci. USA 85, 5399-5403. Wang, Z., and Becker, M. M. (1988) Proc. Natl. Acad. Sci. USA 85, 654-658.
15. Nielsen, P. E., Jeppesen, C. and Buchardt, O. (1988) FEBS Lett. 235, 122-124. Jeppesen, C. and Nielsen, P. E. (1989) Nucl. Acids Res. 17, 4947.
16. Jeppesen, C., Buchardt, O., Henriksen, U., and Nielsen, P. E. (1988) FEBS Lett. 229, 73-76.
17. Pyle, A. M., Long, E. C. and Barton, J. K. (1989) J. Am. Chem. Soc. 111, 4520-4522.
18. Fox, K. R. (1988) Biochem. Biophys. Res. comm. 155, 779-785.
19. Maniatis, T., Fritsch, E. F. and Sambrook, J. (1982) Molecular Cloning, a Laboratory Manual, Cold Spring Harbor Laboratory, Cold Spring Harbor, N.Y.
20. Luck, G., Zimmer, C., Reinert, K. -E., and Arcamone, F. (1977) Nucl. Acids Res. 4, 2655-2670.
21. Modrich, P., and Zabel, D. (1976) J. Biol. Chem. 251, 5866-5874.
22. Fox, K. R. and Waring, M. J. (1984) Nucl. Acids Res. 12, 9271-9285. Spassky, A, and Sigman, D.S. (1985) Biochemistry 24, 8050-8056. Kuwabara, M., Yoon, C., Goyne, T., Thederahn, T., and Sigman, D. S. (1986) Biochemistry 25, 7401-7408.
23. Maxam, A. and Gilbert, W. (1980) Methods in Enzymology 65, 499-560.
24. Coll, M., Frederick, C. A., Wang, A. H. -J., Rich, A. (1987) Proc. Natl. Acad. Sci. USA 84,8385-8389. Kopka, M. L., Yoon, C., Goodsell, D., Pjura, P. and Dickerson, R. E. (1985) J. Mol. Biol. 183, 553-563.
25. Frederick, C. A., Grable, J., Melia, M., Samudzi, C., Jen-Jacobson, L., Wang, B. -C., Greene, P., Boyer, H. W. Rosenberg, J. M. (1984) Nature 309, 327-331. McClarin, J. A., Frederick, C. A., Wang, B. -C., Greene, P., Boyer, H. W., Grable J., and Rosenberg, J. M. (1986) Science 234, 1526-1541.
26. Sluka, J. P. Horvath, S. J., Bruist, M. F., Simon M. I. and Dervan, P. B. (1987) Science 238, 1129-1132.

27. Mei, H. -Y. and Barton, J. K. (1988) Proc. Natl. Acad. Sci. USA 85, 1339–1343.
28. Pyle, A. M., Rehmann, J. P., Meshoyrer, R., Kumar, C. V., Turro, N. J. and Barton, J. K. (1989) J. Am. Chem. Soc. 111, 3051–3058.
29. Pyle, A. M. (1989) Ph.D Dissertation, Columbia University.
30. It appears that, in general, metallointercalatio reagents associate from the major groove of the DNA helix. For an example, see: Wang, A.H. -J., Nathans, J., van der Marel, B., van Boom, J. H., Rich, A. (1978) Nature 276, 471–474.
31. Protugal, J., & Waring, M. J. (1987) FEBS Lett. 225, 195–200. Van Dyke, M. W., Hertzberg, R. P. and Dervan, P. B. (1982) Proc. Natl. Acad. Sci. USA 79, 5470–5474. Harshman, K. D. and Dervan, P. B. (1985) Nucl. Acids Res. 13, 4825–4835.
32. Given that the $K_b$ of distamycin to the $T_6$ footprinting site is $-10^{7-8} M^{-1}$ (Zimmer, C. and Waehnert, U. (1986) Prog. Biophys. Molec. Biol. 47, 31–112) and given the concentrations of the rhodium complex distamycin used in the experiment, one can apply a binding model similar to that of enzyme kinetics employed in the presence of a kinetic inhibitor (Segal, I. H. (1975) Enzyme Kinetics: Behavior and Analysis of Rapid Equilibrium and Steady State Enzyme Systems, Wiley Interscience, New York.)
33. Juris, A.; Balzani, V.; Barigelletti, F.; Campagna, S. Belser, P.; and Von Zelewsky A. Coord. Chem. Revs. 84, 1988, 85.
34. Gillard, R. D.; Hill, R. E. E. J. Chem Soc., Dalton Trans. 1974, 1217.
35. Demas, J. N.; Crosby, G. A. J. Amr. Chem. Soc. 93. 1971, 2841.
36. Kumar, C. V.; Barton, J. K.; Turro, N. J. J. Amer. Chem. Soc. 107, 1985, 5518.
37. Friedman, A. E. Kumar, C. V.; Turro, N. J.; Barton, J. K. Manuscript in preparation.
38. We thank J. -C. Chambron for the gift of Ru(bpy)2(dppz)2+
39. Chambron, J. -C.; Sauvage, J. -P.; Amouyal, E.; Koffi, P. Neuv. J. De Chimie. 9. 1985, 527.
40. Buffer R+50.0 mM NaCl, 5.0 mM Tris-OH, pH +7.0
41. Buffer R-L+20.0 mM NaCl, 2.0 mM Tris-OH pH=7.0, 4 µM Co(NH3)63+.
42. Pohl, F. M.; Jovin, T. M.; Baehr, W.; Holbrook, J. J., 1972, Proc.Natl. Acad. Sci. USA, 69, 3805-9.
43. Mei, H. -Y.; Barton, J. K., 1988, Proc. Natl. Acad. Sci. USA, 85, 1339–43.
44. Friedman, A. E.; Jaycox, G. D.; Barton, J. K. Manuscript in preparation.
45. Sutin, N; Creutz, C., Pure Appl. Chem., 1980, 52, 2717.
46. Kalyasundaram, K., Coord. Chem. Rev., 1982, 46, 159.
47. Meyer, T. J., Pure Appl. Chem., 1986, 58,1193.
48. Ghosh, P. K; Bard, A. J., J. Phys. Chem., 1984, 88, 5519. Krenske, D..; Abto, S.; Van Damme, H.; Cruz, M.; Fripiat, J. J., J. Phys. Chem., 198), 84, 2447.
49. Kumar, C. V.; Barton, J. K.; Turro, N. J., J. Am. Soc., 1985, 107, 5518. Barton, J. K., Science (Washington, D.C.) 1986, 233, 727.
50. Juris A.; Barigelletti, F.; Balzani, V.; Belser, P.; von Zelewsky, A., Isr. J. Chem. 1982, 22, 87.
51. Belser, P.; von Zelewsky, A.; Zahnder, M., Inorg. Chem., 1981, 20, 3098.
52. Warren, L. Inorg. Chem., 1977, 16, 2814.
53. Tome Dieck, H.; Reick, I., Angew. Chem., int. Ed. Engl. 1970, 9, 793.
54. Schlosser, v. K. Z., Chem., 1970, 10, 439.
55. Tuchtenhagen, G.; Ruhlmann, K., Justus Liebigs Ann. Chem., 1968, 711, 174.
56. Schlosser, v. K. Z., Anorg. Allg. Chem., 1972, 387, 91.
57. Blue ruthenium species are produced in great quantity if the reaction is allowed to reflux too long or if concentrated solutions of Ru(phi)3$^{2+}$ are allowed to stand for long periods of time. Chromatography has shown these species to be variable and high in molecular weight. Deep blue ruthenium species have been observed previously and formulated either as clusters or ligand-bridged multinuclear species.[14]
58. Rose, D.; Wilkinson, G., J. Chem. Soc. A, 1970, 1791.
59. Curtis, J.; Sullivan, B. P. Meyer, T. J., Inorg. Chem., 1983, 22, 224.
60. Gutman, V., The Donor-Acceptor Approach to Molecular Interactions, Plenum: New York, 1978.
61. The additional intense band at 5.10 nm leads to the purple coloration in the complex. A comparable pair of low-energy transitions are found .n the benzoquinone dimine derivative.
62. Ackerman, M. N.; Interrante, L. V., Inorg. Chem., 1984, 23, 3904.
63. Mabrouk, P. A.; Wrighton, M. S., Inorg. Chem., 1986, 25, 526. Dumar, C. V.; Gould, I. S.; Barton, J. K.; Turro, N. J., submitted for publication.
64. It is interesting that the transition centered at 510 nm in Ru(phi)3$^{2+}$ is not at all apparent in mixed-ligand complexes containing the phi ligand. Instead, the 525-nm transition in Ru(bpy)2(phi)$^{2+}$ species. The visible spectrum of Ru(bpy) (phi)2$^{2+}$ (data not shown) shows visible transitions centered at 472 and 572 nm, consistent with some degree of delocalization.
65. A similar delocalization may explain the intense visible transition in the ruthenium cage complex recently prepared by Sargeson, et al. (personal communication).
66. Barton, J. K., Science 1986, 233, 727.
67. Dervan, P. B., Science 1986, 232, 464; Wade, W. S.; Dervan, P. B. J. Am. Chem. Soc. 198. 109, 1574.
68. Berman, H. M.; Young, P. R. Ann. Rev. Biophys. Bioeng. 1981 10, 87.
69. Waring, M. J.; Fox, K. R.; Grigg, G.;. Biochem. J. 1987 143, 847; Burchardt, G.; Waehnert, U.; Luck, G.; Zimmer, C. Stud. Biophys. 1986 114, 225; Kissinger, K. Krowicki, K., Dabrowiak, J. C., Lowr, J. W. Biochemistry 1987 26, 5590.
70. Quigley, G. J.; Ughetto, G.; van der Marel, G.; van Boom, J. H.; Wang, A. H. -J.; Rich, A. Science 1986 232, 1255; Kopka, M. L.; Yoon, C.; Goodsell, D.; Pjura, P.; Dickerson, R. E. Proc. Natl. Acad. Sci. U.S.A. 1985 82, 1376; Pjura, P. W.; Grezeskowiak, K. Dickerson, R. E. J. Mol. biol. 1987 197, 257.
71. Wilson, W. D.; Wang, Y -H.; Kusuma, S.; Chandrasekaran, S.; Yang, N. C.; Boykin, D. W. J. Am. Chem. Soc. 1985, 107, 4989–4995.
72. Breslauer, K. J., Remata, D. P.: Chcu, W. Y.: Ferrante, R.; Curry, J.; Zaunczkowski, D.; Snyder, J. G.; Marky, L. A. Proc. Natl. Acad. Sci. U.S.A. 1987 84, 8922; Ibanez, V.; Geacintov, N. E.; Gagliano, A. G.; Brondimarte, S.; Harvey, R. G. J. Am. Chem. Soc. 1980, 102, 5661.

73. Kumar, C. V.; Barton, J. K.; Turro, N. J. J. Am. Chem. Soc. 1985, 107, 5518.
74. Barton, J. K.; Goldberg, J. M.; Kumar, C. V.; Turro, N. J. J. Am. Chem. Soc. 1986, 108, 2081 J. Rehmann, Ph.D. Dissertation, Columbia University.
75. Mei, H. -Y.; Barton J. K.; Raphael A. L. Proc. Natl. Acad. Sci. U.S.A. 1985, 82, 6460.
76. Kirshenbaum, M. R.; Tribolet, R.; Barton, J. K. Nucl. Acids Res. 1988, 16, 7943.
77. Meyer, T. J. Pure and Appl. Chem. 1986 58, 1193; Sutin, N. and Creutz, C. Pure Appl. Chem. 1980 52, 2717.
78. Belser, P.; von Zelewsky, A. Zehnder, M. Inorg. Chem. 1981 20, 3098.
79. Pyle, A. M.; Barton, J. K. Inorg. Chem. 1987 26, 3820.
80. Krause, R. A. Inorg. Chem. Acta 1977 22, 209.
81. Lin, C. -T.; Botcher, W.; Chou, M.; Creutz, C.; Sutin, N. J. Am. Chem. Soc. 1976 98, 6536.
82. Henderson, L. J.; Fronczek, F. R.; Cherry, W. R. J. Am. Chem. Soc. 1984 106, 5876.
83. Mass spectral data are reported as mass/ion values, rather than mass/charge ratios.
84. Kumar, C. V.; Barton, J. K.; Turro, N. J. Inorg. Chem. 1987 26, 1455.
85. Dallinger, R. F.; Woodruff, W. H. J. Am. Chem. Soc. 1979 101 4391; Bradley, P. G.; Kress, N.; Hornberger, B. A.; Dallinger, R.; Woodruff, W. H. J. Am. Chem. Soc. 1981 103 7441. Smothers, W. K.; Weighton, M. S. J. Am. Chem. Soc. 1983 105, 1067.
86. Keller, W. Proc. Natl. Acad. Sci. U.S.A. 1975 72, 4876.
87. Wang, J. C. J. Mol. Biol. 1974 89, 783.
88. Scatchard, G. Ann. NY. Acad. Sci. 1949 51, 660.
89. McGheem J. D.; von Hippel, P. H. J. Mol. Biol. 1974 86, 469.
90. Mason, S. F.; Peart, B. J. Chem. Soc. Dalton Trans. 1973, 949.
91. Bloomfield, V. A.; Crothers, D. M.; Trinoco, Jr., I. Physical Chemistry of Nucleic Acids, Harper and Row, New York 1974, p. 432.
92. Wolfe, A.; Chimer, G. H.; Meehan, T. Biochem. 1987 26, 6392.
93. Waring, M. J. J. Mol. Biol. 1970 54, 247.
94. The unwinding angle for Ru(phen)$_3^{2+}$ has been measured by others as well and compares favorably with our determination. See Kelly, J. M.; Tossi, A. B.; McConell, D. J.; OhVigin, C. Nucl. Acids. Res. 1985 13, 6017.
95. Kumar, C. V.; Barton, J. K.; Gould, I. R.; Turro, N. J.; Van Hooten, J. Inorg. Chem. 1988, 27, 648.
96. These results taken together provide strong evidence in support of intercalation, but only a crystal structure of the complex bound to the oligonucleotide may be considered definitive.
97. Although much can be inferred about the binding mode of the complex from these spectroscopic results, no conclusions may be drawn concerning similarities in where the complexes bind on the helix, either with respect to sequence to groove location.
98. Goldstein, B. M.; Barton, J. K.; Berman, H. M. Inorg. Chem. 1986 25, 842.
99. The fact that a lower concentration of Ru(phi)2-bpy$^{2+}$ is needed for 50% helix unwinding compared to Ru(bpy)2phi$^{2+}$ may be consistent with this idea.
100. Consistent with this idea, both Ru(DIP)$_3^{2+}$ appear to bind DNA more avidly than their mi<ed ligand analogs, though their poor solubility makes the quantitative comparison difficult.
101. The calculations of solvent accessible surface area were performed using water as the probe molecule (radius of 1.58 A) using the program Macromodel, written by W. C. Still, Columbia University.
102. A. M. Pyle and J. K. Barton, unpublished results.

What is claimed is:

1. A coordination complex or salt thereof which is spectroscopically or photoactively determinable when bound to DNA having the formula $$R_1-M-R_3,$$
$$\overset{R_2}{|}$$

wherein M is Ru, Rh, Co, Fe, Cr, Cu, Zn, Cd, or Pb, and each of $R_1$, $R_2$, and $R_3$ is ethylenediamine, bipyridine, 2,2'-bipyridine (bpy), 4,4'diphenyl bipyridine, bis 4,4' methyl bipyridylate, bis 4,4' bipyridylamide, phenanthroline, 1,10-phenanthroline (phen), 4,7-diamino-1,10-phenanthroline, 3,8-diamino-1,10-phenanthroline, 4,7-diethylenediamine-1,10-phenanthroline, 3,8-diethylenediamine-1,10-phenanthroline, 4,7-dihydroxyl-1,10-phenanthroline, 3,8-dihydroxyl-1,10-phenanthroline, 4,7-dinitro-1,10-phenanthroline, 3,8-dinitro-1,10-phenanthroline, 4,7-diphenyl-1,10-phenanthroline (DIP), 3,8-diphenyl-1,10-phenanthroline, 4,7-dispermine-1,10-phenanthroline, 3,8-dispermine-1,10-phenanthroline, 5-nitrophenanthroline (5-NO$_2$phen), 3,4,7,8-tetramethyl-phenanthroline (TMP), diazafluorene-9-one, 4,5-diazafluorene-9-one (flone), phenanthrenequinonediimine, 9,10-phenanthrenequinonediimine (phi), dipyridophenanzine, or 3,2-dipyridophenazine (dppz); wherein $R_1$, $R_2$, and $R_3$ are bound to M by coordination bonds and wherein $R_1$ and $R_2$ may be the same or different, but if the same are different from $R_3$; with the proviso that the complex does not have the formula M(byp)$_2$(dppz).

2. A complex of claim 1, wherein M is Ru, Rh, or Co.
3. A complex of claim 1, wherein $R_1$ and $R_2$ are the same.
4. A complex of claim 3 having the formula M(phen)$_2$(phi), M(byp)$_2$(phi), M(phi)$_2$(bpy), M(phi)$_2$(4,4'diphenylbipyridine), M(bis 4,4'methyl bipyridylate)$_2$(phi), M(bis 4,4'bipyridylamide)$_2$(phi), M(bpy)$_2$(phen), M(phen)$_2$(bpy), M(phen)$_2$(flone), M(bpy)$_2$(DIP), M(phen)$_2$(DIP), M(DIP)$_2$(phen), M(phen)$_2$(dppz), M(DIP)$_2$(dppz), or M(dppz)$_2$(phen).
5. A complex of claim 4, wherein M is Ru, Rh, or Co.
6. A complex of claim 5, wherein M is Ru.
7. A complex of claim 5, wherein M is Rh.
8. A coordination complex or salt thereof which is spectroscopically or photoactively determinable when bound to DNA having the formula $$R_1-M-R_3,$$
$$\overset{R_2}{|}$$

wherein M is Ru, Rh, Co, Fe, Cr, Cu, Zn, Cd, or Pd, and each of $R_1$, $R_2$, and $R_3$ is ethylenediamine, bipyridine, 2,2'-bipyridine (bpy), 4,4'diphenyl bipyridine, bis 4,4'methyl bipyridylate, bis 4,4'bipyridylamide, phenanthroline, 1,10-phenanthroline (phen), 4,7-diamino-1,10-phenanthroline, 3,8-diamino-1,10-phenanthroline, 4,7-diethylenediamine-1,10-phenanthroline, 3,8-diethylenediamine-1,10-phenanthroline, 4,7-dihydroxyl- 1,10-phenanthroline, 3,8-dihydroxyl-1,10-phenanthroline, 4,7-dinitro-1,10-phenanthroline, 3,8-dinitro-1,10-phenanthroline, 4,7-diphenyl-1,10phenanthroline (DIP), 3,8-diphenyl-1,10-phenanthroline, 4,7-dispermine-1,10-phenanthroline, 3,8-dispermine-1,10-phenanthroline, 5-nitrophenanthroline (5-NO$_2$phen), 3,4,7,8-tetramethylphenanthroline (TMP), diazafluorene-9-one, 4,5-diazafluorene-9-one (flone), phenanthrenequinonediimine, 9,10-phenanthrenequinonediimine (phi), dipyridophenazine, or 3,2-dipyridophenazine (dppz); wherein $R_1$, $R_2$, and $R_3$ are bound to M by coordination bonds, provided that at least one of $R_1$, $R_2$, or $R_3$ is dipyridophenazine, of 3,2-dipyridophenazine (dppz); with the proviso that the complex does not have the formula M(byp)$_2$(dppz).

9. A complex of claim 8, wherein M is Ru.

10. A complex of claim 9 having the formula Ru(phen)$_2$(dppz)$^{2+}$.

11. A complex of claim 9 having the formula Ru(DIP)$_2$(dppz)$^{2+}$.

12. A complex of claim 9 having the formula Ru(dppz)$_2$(phen)$^{2+}$.

13. A complex of claim 9 having the formula Ru(dppz)$_2$(bpy)$^{2+}$.

14. A coordination complex or salt thereof which is spectroscopically or photoactively determinable when bound to DNA having the formula

wherein M is Ru or Rh and R is 9–10-phenanthrenequionediimine, 5-nitrophenanthroline, or 3,2-dipyridophenazine.

15. The optically resolved delta isomer of the complex of claim 14.

16. The optically resolved lambda isomer of the complex of claim 14.

17. A pharamceutical composition which comprises an amount of the complex Rh(DIP)$_3$ effective to inhibit the activity of human immunodeficiency virus and a pharmaceutically acceptable carrier.

18. A method of inhibiting the growth of HIV in HIV-infected cells which comprises contacting the cells with an amount of an Rh(DIP)$_3$ complex effective to inhibit the growth of HIV.

* * * * *